US008974793B2

(12) United States Patent
West et al.

(10) Patent No.: US 8,974,793 B2
(45) Date of Patent: Mar. 10, 2015

(54) METHODS AND SYSTEMS FOR INDUCING IMMUNOLOGIC TOLERANCE TO NON-SELF ANTIGENS

(75) Inventors: Lori Jeanne West, Edmonton (CA); Todd Lambert Lowary, Edmonton (CA); Jillian Mary Buriak, Edmonton (CA); Brian Daly, Edmonton (IE); Mylvaganam Jeyakanthan, Alberta (CA); Peter John Meloncelli, Edmonton (CA); Vincent Arthur Wright, Edmonton (CA); Anne Margaret Cooper, Edmonton (CA)

(73) Assignee: The Governors Of The University Of Alberta, Edmonton, Alberta (CA)

( * ) Notice: Subject to any disclaimer, the term of this patent is extended or adjusted under 35 U.S.C. 154(b) by 103 days.

(21) Appl. No.: 13/139,387

(22) PCT Filed: Dec. 11, 2009

(86) PCT No.: PCT/CA2009/001814
§ 371 (c)(1),
(2), (4) Date: Sep. 29, 2011

(87) PCT Pub. No.: WO2010/066049
PCT Pub. Date: Jun. 17, 2010

(65) Prior Publication Data
US 2012/0021056 A1    Jan. 26, 2012

Related U.S. Application Data

(60) Provisional application No. 61/121,784, filed on Dec. 11, 2008.

(51) Int. Cl.
| A61K 39/00 | (2006.01) |
| A61L 31/16 | (2006.01) |
| A61K 47/48 | (2006.01) |
| A61K 49/04 | (2006.01) |
| B82Y 5/00 | (2011.01) |

(52) U.S. Cl.
CPC ............... *A61L 31/16* (2013.01); *A61K 39/001* (2013.01); *A61K 47/48215* (2013.01); *A61K 47/48861* (2013.01); *A61K 49/0423* (2013.01); *B82Y 5/00* (2013.01); *A61K 2039/55555* (2013.01); *A61K 2039/6093* (2013.01); *A61K 2039/627* (2013.01); *A61L 2300/438* (2013.01); *A61L 2300/80* (2013.01)
USPC .................... 424/184.1; 424/193.1; 536/1.11; 623/1.42

(58) Field of Classification Search
None
See application file for complete search history.

(56) References Cited

U.S. PATENT DOCUMENTS

| 5,698,679 A * | 12/1997 | Nemazee .................. 530/387.3 |
| 5,977,079 A | 11/1999 | Good et al. |
| 7,279,561 B1 * | 10/2007 | Molnar-Kimber et al. .................. 530/388.9 |
| 7,355,017 B2 * | 4/2008 | Lofling et al. ............. 530/391.1 |
| 2002/0065546 A1 * | 5/2002 | Machan et al. ............. 623/1.13 |
| 2003/0129215 A1 * | 7/2003 | Mollison et al. ............. 424/426 |
| 2004/0234511 A1 | 11/2004 | Galili et al. |
| 2006/0154890 A1 * | 7/2006 | Bratzler et al. ................. 514/44 |
| 2009/0169578 A1 * | 7/2009 | Pascual et al. ............. 424/192.1 |

FOREIGN PATENT DOCUMENTS

| WO | 98/33387 | 8/1998 |
| WO | WO 9833387 A1 * | 8/1998 |
| WO | 03/024500 | 3/2003 |
| WO | WO 03024500 A1 * | 3/2003 |

OTHER PUBLICATIONS

Kang et al., Thin Solid Films, vol. 515, Issue 12, Apr. 23, 2007, pp. 5184-5187.*
Janeway et al., Immunobiology, 3rd edition, 1997, Garland Publications, p. 2:2.*
Li et al., Zhongguo Fei Ai Za Zhi. Oct. 2012;15(10):561-8. doi: 10.3779/j.issn.1009-3419.2012.10.01.*
Borenstein et al., Induction of Xenogeneic Neonatal Tolerance to Transgenic Human Leukocyte Antigen Class I Grafts, Transplantation, 78, pp. 844-852, 2004.
Ogawa et al., Induction of Immune Tolerance to a Transplantation Carbohydrate Antigen by Gene Therapy with Autologous Lymphocytes Transduced with Adenovirus Containing the Corresponding Glycosyltransferase Gene, Gene Therapy, 11, pp. 292-301, 2004.

(Continued)

*Primary Examiner* — Michael Szperka
(74) *Attorney, Agent, or Firm* — Morgan, Lewis & Bockius LLP

(57) ABSTRACT

Described herein are methods and systems that can be used to induce immunologic tolerance to non-self antigens. The methods and systems comprise introducing a tolerogen comprising at least one immunogenic non-self antigen coupled to a carrier, wherein the immunogenic antigen can be a foreign or endogenous antigen or fragments thereof. The non-self antigen can be selected from the group consisting of carbohydrate antigens, full-length antigenic proteins, and fragments and combinations thereof, while the carrier can be selected from nanoparticles and stents. Tolerogen compositions are also provided and can be used to induce immunologic tolerance to non-self antigens. These methods, systems and compositions are particularly advantageous since they can be used to allow for the extension of the window of safety for immunologically-incompatible transplantations to patients who are growing past the age of infancy.

56 Claims, 32 Drawing Sheets

(56) References Cited

OTHER PUBLICATIONS

West, Targeting Antibody-Mediated Rejection in the Setting of ABO-Incompatible Infant Heart Transplantation: Graft Accommodation vs. B Cell Tolerance, Current Drug Targets—Cardiovascular & Haematological Disorders, 5, pp. 223-232, 2005.

West, B-cell Tolerance Following ABO-Incompatible Infant Heart Transplantation, Transplantation, 81, pp. 301-307, 2006.

Grumet et al., Soluble Form of an HLA-B7 Class I Antigen Specifically Suppresses Humoral Alloimmunization, Human Immunology, 40, pp. 228-234, 1994.

Fan et al., Donor-specific B-cell Tolerance After ABO-Incompatible Infant Heart Transplantation, Nature Medicine, 10, pp. 1227-1233, 2004.

International Search Report and Written Opinion for PCT/CA2009/001814 dated Mar. 17, 2010.

Galili, Xenotransplantation and ABO Incompatible Transplantation: The Similarities They Share, Transfusion and Apheresis Science 35, pp. 45-58, 2006.

Ogawa, Induction of B Cell Tolerance to Incompatible ABO Blood Group Antigens in Transplantation, Xenotransplantation 14, p. 452, 2007.

Supplemental European Search Report for Application No. 09831358.8 dated Jun. 13, 2013.

* cited by examiner

O-antigen　　　　A-antigen　　　　B-antigen

| Name | Position | FWHM | R.S.F. | Area | % Conc. |
|---|---|---|---|---|---|
| C 1s | 286.54 | 1.392 | 1 | 12889.8 | 100.000 |
| C=O | 287.95 | 1.385 | 1 | 885.3 | 6.870 |
| C-H/C-C | 284.94 | 1.356 | 1 | 4200.2 | 32.580 |
| C-O/C-N | 286.51 | 1.212 | 1 | 7806.2 | 60.550 |

Modified ELISA Assay Using Peanut Agglutinin

ELISA Using Mouse Anti-A Antibodies

ELISA Assay After Incubation With Pig A Blood Plasma

METHODS AND SYSTEMS FOR INDUCING IMMUNOLOGIC TOLERANCE TO NON-SELF ANTIGENS

CROSS-REFERENCE TO RELATED APPLICATIONS

The present application is a U.S. National Phase Application of International Application PCT/CA2009/001814 filed Dec. 11, 2009, which claims the benefit of U.S. Provisional Application No. 61/121,784, filed Dec. 11, 2008, which are hereby incorporated by reference in their entirety.

FIELD OF THE INVENTION

The present invention relates to the field of immunologic incompatibility in medical treatment, and more specifically, to methods and systems for inducing immunologic tolerance to non-self antigens.

BACKGROUND

Organ transplants are often life-saving medical therapies for a wide variety of ailments. For example, which is not meant to be limiting, neonatal heart transplantation is a relatively new therapy for congenital cardiac malformations and cardiomyopathies that would otherwise be lethal. Although organ transplants are life-saving in many cases, they are often difficult to offer to many patients who require this type of medical treatment. The waiting lists for various organ transplants are very long, and many patients die before a compatible donor organ can be found.

The two most important obstacles to providing this type of medical therapy are the lack of sufficient donor organs and the need for life-long immunosuppressive drug therapy, which can cause many undesirable, and sometimes life-threatening, side-effects. The donor pool for various organs is unfortunately very small, and finding a donor can prove extremely challenging depending on the type of organ and the age group of the recipient. Moreover, in order for a donor organ to be found, there must be blood group compatibility. This requirement can further severely limit the chances of finding an appropriate donor in a timely fashion.

In organ transplantation, blood group incompatibility between donor and recipient is a seemingly insurmountable immunologic barrier. ABH histo-blood group antigens are complex polysaccharide structures expressed on many tissues of embryonic mesodermal origin, including vascular endothelium (Cartron, J. P., Colin, Y. *Transfusion Clinique et Biologique*, 2001, 8:163-99; Mollicone, R., Candelier, J. J., Mennesson, B. et al., *Carb. Res.*, 1992, 228:265-76; Oriol, R., Mollicone, R., Coullin, P, et al. *APMIS Supplementum*, 1992, 27:28-38). Expression of only the H chain defines individuals of the O blood group, while addition of the A or B terminal trisaccharide residues, or both, catalyzed by genetically-determined production of specific glycosyltransferases, defines individuals of A, B and AB blood groups, respectively.

Organ transplantation across ABO barriers is usually followed by "hyperacute" rejection, a process initiated by the binding of pre-formed antibodies to cognate ABH antigens expressed on graft endothelium (Starzl, T., Ishikawa, M., Putnam, C., et al. *Transp. Proc.*, 1974, 6:129-139; Stock, P., Sutherland, D., Fryd, D., et al. *Transp. Proc.*, 1987, 19:711-712). This initiates a cascade of complement activation, recruitment of inflammatory cells and release of inflammatory mediators, which results in rapid and irreversible thrombosis of graft vasculature.

Due to the overwhelming need for donor organs, attempts have been made to cross the ABO barrier, particularly in kidney transplantation (Slapak, M., Naik, R., Lee, H. *Transplantation*, 1981, 31:4-7, Bannett, A., Bensinger, W., Raja, R., et al. *Transp.*, 1987, 43:909-911; Alexandre, G., Squifflet, J., De Bruyere, M., et al. *Transp. Proc.*, 1987, 19:4538-4542; Takahashi, K., Yagisawa, T., Sonda, K, et al. *Transp. Proc.*, 1995, 25:271-273; Gugenheim, J., Samuel, D., Reynes, M., et al. *Lancet*, 1990, 336:519-523). Success requires aggressive maneuvers in the recipient to remove pre-formed antibodies, including splenectomy, plasmapheresis, and B-cell pharmacologic agents. In many cases, however, anti-donor antibodies return due to B-cell memory. ABO-incompatible transplantation of cardiac allografts is never intentionally undertaken due to the lack of effective "rescue" therapies (such as dialysis in the case of renal transplant failure), combined with susceptibility of the heart to antibody-mediated rejection, with consequent events such as arrhythmias and graft vasculopathy. Until recently, the worldwide experience of ABO-incompatible heart transplantation was only described in 8 cases, all performed as a result of errors in determining or reporting the donor blood type, and with a high lethality rate (6 out of 8 cases) (Cooper, D. J. *Heart Lung Transp.*, 1990, 9:376-381).

Recently, it was shown by the present inventors that the ABO blood group barrier can be breached safely in infants (West, L. J., Pollock-Barziv, S. M., Dipchand, A. I., et al. *New Eng. J. Med.*, 2001, 344:793-800), and results in spontaneous development of immunologic tolerance to donor A/B antigens (Fan, X., Ang, A., Pollock-BarZiv, S. M., et al. *Nature Medicine*, 2004, 11:1227-33). Delayed production of ABO-antibodies during normal infancy combined with high waiting list mortality led the present inventors in 1996 to begin a clinical trial of ABO-incompatible heart transplantation in 10 infant patients (median age 2 months) (West, L. J., Pollock-Barziv, S. M., Dipchand, A. I., et al. *New Eng. J. Med.*, 2001, 344:793-800). Although never performed intentionally in adult heart transplant patients, it was reasoned that hyperacute rejection of ABO-incompatible heart grafts would not occur in the absence of pre-formed antibodies during this period of delayed antibody development. Eight of the ten infants survived, with the two deaths being unrelated to ABO incompatibility. There was no evidence of hyperacute rejection, nor were there significant clinical problems attributable to blood group incompatibility. The survival rate seen in this clinical trial was well within the rate expected at the time. In fact, the Canadian Institute for Health Information reported that the survival rate for first-time heart transplant recipients treated between 1996 and 2001 was 78% (http://secure.cihi.ca/cihiweb/dispPage.jsp?cw_page=media_22sep2004_e). Expansion of the donor pool afforded by this approach contributed to a dramatic decrease in waiting list mortality for infants at the inventors' institution (58% to 7%). However, although successful, this clinical protocol remains limited to very young infants.

Neonatal tolerance occurs when foreign antigens are intentionally introduced during a critical window of immaturity, resulting in permanent elimination of an immune response without further immunomodulatory maneuvers (Billingham, R. E., Brent, L, Medawar, P. B. *Nature*, 1953, 172:603-606; Owen, R. *Science*, 1945, 102:400; Streilein, J. W., Klein, J. J. *Immun.*, 1977, 119:2147-50; McCarthy, S. A., Bach, F. H. *J. Immun.*, 1983, 131:1676-82). The exquisite susceptibility of the immature immune system to tolerance induction was first proposed by Burnet (Burnet, F. *The Clonal Selection Theory of Acquired Immunity*: Cambridge Press, 1959), based on the work of Owen describing the immune consequences of a shared placental circulation in calves (Owen, R. *Science*, 1945, 102:400). The concept of "acquired immune tolerance to foreign antigens", thought to mirror the development of self-tolerance, was later defined and expanded in the mid-20$^{th}$ century by Medawar and colleagues (Billingham, R. E., Brent, L, Medawar, P. B. *Nature*, 1953, 172:603-606; Medawar, P. *Proc. R. Soc.* (*Lond*), 1956, 146B:1-8; Billingham, M. E., Brent, L. *Philos. Trans.* (*Biol. Sci.*), 1959, 242B: 439-444). Demonstrations of neonatal tolerance were limited to rodent models until the inventors studied the immunologic development of infant recipients of ABO-incompatible heart transplants (Fan, X., Ang, A., Pollock-BarZiv, S. M., et al. *Nature Medicine*, 2004, 11:1227-33). Using a panel of in vitro assays to study patients' blood and biopsy samples for the detection of specific antibodies and B cells, the present inventors showed that donor-specific B-cell tolerance develops spontaneously after ABO-incompatible transplantation. Combined evidence demonstrating this state of tolerance included: deficiency of circulating antibodies to donor A/B antigens, presence of circulating antibodies to "third-party" antigens, lack of intragraft deposition of immunoglobulin and complement components, absence of donor-specific antibody-producing cells by ELISA and ELISPOT assays and absence of antigen-specific B-cells by FACS analysis. This was the first study showing that neonatal tolerance can occur in humans, and by cellular and molecular mechanisms similar to those previously demonstrated in murine models. Importantly, persistence of donor A/B antigens within the heart graft was also demonstrated in these infant recipients some years after ABO-incompatible transplantation.

Although the above clinical procedures have proven successful and have demonstrated that inducing immune tolerance is possible, these procedures remain limited to use in neonates in the short window during which their immune system is immature. Once the immune system matures, however, inducing immune tolerance to non-self antigens generally becomes impossible and ABO-incompatible transplantation becomes life-threatening. The pool of donor organs becomes limited once again since only compatible organs can be used.

Previously, tolerogens and tolerogen compositions have been introduced to try to prevent the occurrence of organ transplant rejection. It was hoped that their use would prevent or lessen an immunologic reaction to the donor organ, and reduce reliance on immunosuppressant drug therapies, which carry many unpleasant, and sometimes life-threatening, side-effects. For example, David Cohen teaches, in U.S. Patent Application No. 20080044435, a Tat-based tolerogen composition comprising at least one immunogenic antigen coupled to at least one human immunodeficiency virus trans-activator of transcription (Tat) molecule. This composition is claimed to be helpful in the suppression of organ transplant rejection. There are, however, several major limitations to this technique. First, these tolerogens are all Tat-based, which depend on the recombinant production of Tat and the linking of antigens to this recombinant protein. Recombinant protein production is, in many cases, complicated and costly, and limited to in vivo systems. Further, the recombinant protein must be pure and homogeneous in order to be acceptable for use as a human drug therapy. Second, the reliance on Tat may limit the type of antigen that can be used. These limitations can severely hinder the use of such compositions in the broad medical community, where a great number of patients would be treated.

In U.S. Patent Application No. 20050214247, Sunil Shaunak and co-workers describe anionic glycodendrimers that are claimed to be useful in the suppression of organ transplant rejection. These molecules are, however, all dendrimer-based. The requirement for the use of denthimers can significantly increase production costs and may also hinder the type of antigens that can be used. Further, these glycodendrimers need to be continuously administered to patients to maintain the suppression of organ transplant rejection. These limitations would again greatly limit the use of these glycodendrimers in the broader medical community in the suppression of organ transplant rejection.

Other attempts at modulating immune response to organ transplants have focused on the use of postpartum-derived cells (for example, U.S. Patent Application No. 20070264269, WO2006116357, and EP0574527). Cell-based approaches are not, however, easily amenable to large-scale use in the medical community. It is difficult to see how these currently available techniques can be easily used to increase organ donor pools and decrease wait times. Moreover, due to these severe limitations, such tolerogens cannot be successfully used on a large scale to take advantage of the period during which the human immune system is immature and tolerance to non-self antigens can be acquired.

Consequently, there is a need for a method and system that allows for the extension of the window of safety for immunologically-incompatible organ transplantation to patients who are growing past the age of infancy, while avoiding some of the problems listed above. This would allow for the expansion of the potential donor pool, ultimately resulting in decreased waiting list mortality and more efficient use of rarely available donor organs.

This background information is provided for the purpose of making known information believed by the applicant to be of possible relevance to the present invention. No admission is necessarily intended, nor should be construed, that any of the preceding information constitutes prior art against the present invention.

SUMMARY

In accordance with a broad aspect of the invention, there is provided a method for inducing immunologic tolerance to non-self antigens. The method comprises administering a tolerogen, the tolerogen comprising at least one non-self antigen coupled to a carrier. The tolerogen can be administered intravenously or be surgically implanted, and it can be administered to neonates or people growing past the age of infancy to extend the window of safety for immunologically-incompatible transplantations. The non-self antigen can be selected from the group consisting of a carbohydrate antigen, a full-length antigenic protein, and fragments and combinations thereof. In one aspect, a plurality of different non-self antigens can be coupled to the carrier.

The carbohydrate antigen can be selected from the group consisting of the A blood group antigen, the B blood group antigen, the O blood group antigen, the Galili antigen (Gal-α-(1→3)-Gal), and fragments and combinations thereof. The A blood group antigen, the B blood group antigen and the O blood group antigen are selected from the group consisting of Type I, Type II, Type III, Type IV, Type V, and Type VI blood group antigens. The full-length antigenic protein can be selected from the group consisting of human leukocyte antigens class I and human leukocyte antigens class II.

In one aspect, the antigen is coupled to the carrier through a linker. The linker can be an aglycone that has an anchoring group. The anchoring group can be selected from the group consisting of a monoalkoxysilyl, a dialkoxysilyl, a trialkoxysilyl, a monohalosilyl, a dihalosilyl, and a trihalosilyl. In one embodiment, the anchoring group is trimethoxysilyl, while in another, it is trichlorosilyl. In another aspect, the carrier can be selected from the group consisting of a nanoparticle and a stent. The nanoparticle can be a $SiO_2$ nanoparticle or a silica-coated $Fe_3O_4$ nanoparticle. The stent can be made from a wide variety of different materials, which can include, but are not limited to, silica-coated 316L stainless steel and $Al_2O_3$-coated stainless steel.

In another aspect, the tolerogen can further comprise a polyethylene glycol (PEG)-containing molecule coupled to the carrier. The polyethylene glycol-containing molecule can comprise a surface binding group selected from the group consisting of a monoalkoxysilyl, a dialkoxysilyl, a trialkoxysilyl, a monohalosilyl, a dihalosilyl, and a trihalosilyl. In one embodiment, the surface binding group is trimethoxysilyl, while in another, it is trichlorosilyl.

In accordance with another broad aspect of the invention, there is provided a system for inducing immunologic tolerance to non-self antigens. The system comprises a tolerogen that comprises at least one non-self antigen coupled to a carrier. The tolerogen can be administered intravenously or be surgically implanted, and it can be administered to neonates or people growing past the age of infancy to extend the window of safety for immunologically-incompatible transplantations. The non-self antigen can be selected from the group consisting of a carbohydrate antigen, a full-length antigenic protein, and fragments and combinations thereof. In one aspect, a plurality of different non-self antigens can be coupled to the carrier.

The carbohydrate antigen can be selected from the group consisting of the A blood group antigen, the B blood group antigen, the O blood group antigen, the Galili antigen (Gal-α-(1→3)-Gal), and fragments and combinations thereof. The A blood group antigen, the B blood group antigen and the O blood group antigen are selected from the group consisting of Type I, Type II, Type III, Type IV, Type V, and Type VI blood group antigens. The full-length antigenic protein can be selected from the group consisting of human leukocyte antigens class I and human leukocyte antigens class II.

In one aspect, the antigen is coupled to the carrier through a linker. The linker can be an aglycone that has an anchoring group. The anchoring group can be selected from the group consisting of a monoalkoxysilyl, a dialkoxysilyl, a trialkoxysilyl, a monohalosilyl, a dihalosilyl, and a trihalosilyl. In one embodiment, the anchoring group is trimethoxysilyl, while in another, it is trichlorosilyl. In another aspect, the carrier can be selected from the group consisting of a nanoparticle and a stent. The nanoparticle can be a $SiO_2$ nanoparticle or a silica-coated $Fe_3O_4$ nanoparticle. The stent can be made from a wide variety of different materials, which can include, but are not limited to, silica-coated 316L stainless steel and $Al_2O_3$-coated stainless steel.

In another aspect, the tolerogen can further comprise a polyethylene glycol (PEG)-containing molecule coupled to the carrier. The polyethylene glycol-containing molecule can comprise a surface binding group selected from the group consisting of a monoalkoxysilyl, a dialkoxysilyl, a trialkoxysilyl, a monohalosilyl, a dihalosilyl, and a trihalosilyl. In one embodiment, the surface binding group is trimethoxysilyl, while in another, it is trichlorosilyl.

In accordance with another broad aspect of the invention, there is provided a tolerogen that can be used for inducing immunologic tolerance to non-self antigens. The tolerogen comprises at least one non-self antigen coupled to a carrier. The tolerogen can be administered intravenously or be surgically implanted, and it can be administered to neonates or people growing past the age of infancy to extend the window of safety for immunologically-incompatible transplantations.

The non-self antigen can be selected from the group consisting of a carbohydrate antigen, a full-length antigenic protein, and fragments and combinations thereof. In one aspect, a plurality of different non-self antigens can be coupled to the carrier.

The carbohydrate antigen can be selected from the group consisting of the A blood group antigen, the B blood group antigen, the O blood group antigen, the Galili antigen (Gal-α-(1→3)-Gal), and fragments and combinations thereof. The A blood group antigen, the B blood group antigen and the O blood group antigen are selected from the group consisting of Type I, Type II, Type III, Type IV, Type V, and Type VI blood group antigens. The full-length antigenic protein can be selected from the group consisting of human leukocyte antigens class I and human leukocyte antigens class II.

In one aspect, the antigen is coupled to the carrier through a linker. The linker can be an aglycone that has an anchoring group. The anchoring group can be selected from the group consisting of a monoalkoxysilyl, a dialkoxysilyl, a trialkoxysilyl, a monohalosilyl, a dihalosilyl, and a trihalosilyl. In one embodiment, the anchoring group is trimethoxysilyl, while in another, it is trichlorosilyl. In another aspect, the carrier can be selected from the group consisting of a nanoparticle and a stent. The nanoparticle can be a $SiO_2$ nanoparticle or a silica-coated $Fe_3O_4$ nanoparticle. The stent can be made from a wide variety of different materials, which can include, but are not limited to, silica-coated 316L stainless steel and $Al_2O_3$-coated stainless steel.

In another aspect, the tolerogen can further comprise a polyethylene glycol (PEG)-containing molecule coupled to the carrier. The polyethylene glycol-containing molecule can comprise a surface binding group selected from the group consisting of a monoalkoxysilyl, a dialkoxysilyl, a trialkoxysilyl, a monohalosilyl, a dihalosilyl, and a trihalosilyl. In one embodiment, the surface binding group is trimethoxysilyl, while in another, it is trichlorosilyl.

In accordance with another broad aspect of the invention, there is provided a method for suppressing organ transplant rejection comprising administering a tolerogen of the present invention. The tolerogen may be administered to a neonate or to a patient who is growing past the age of infancy. It can be administered intravenously or through surgical implantation.

BRIEF DESCRIPTION OF THE DRAWINGS

The present invention, both as to its organization and manner of operation, may best be understood by reference to the following description, and the accompanying drawings of various embodiments wherein like numerals are used throughout the several views, and in which.

DETAILED DESCRIPTION OF THE INVENTION

The present invention relates to the discovery of methods and systems for inducing immunologic tolerance to non-self antigens. The methods and systems comprise introducing a tolerogen comprising at least one immunogenic non-self antigen coupled to a carrier, wherein the immunogenic antigen can be a foreign or endogenous antigen or fragments thereof. Tolerogen compositions are also provided and can be used to induce immunologic tolerance to non-self antigens. These methods, systems and compositions are particularly advantageous since they can be used to allow for the extension of the window of safety for immunologically-incompatible transplantations to patients who are growing past the age of infancy. The extension of the window of safety can expand the potential donor pool, result in decreased waiting list mortality and more efficient use of rarely available donor organs. They can also minimize the need for chronic systemic pharmacologic immunosuppression and its many attendant side-effects.

Figure 1:
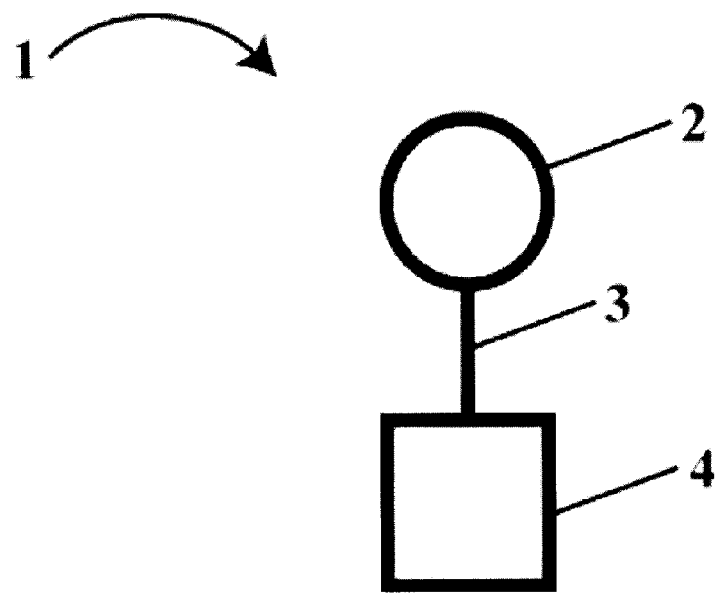
FIG. 1 is a schematic diagram of a tolerogen according to one embodiment of the present invention.

In one embodiment of the present invention (FIG. 1), a tolerogen 1 comprises at least one immunogenic non-self antigen 2 coupled via a linker 3 to a carrier 4. Immunogenic non-self antigen 2 can be selected from the group consisting of carbohydrate antigens, full-length antigenic proteins, and fragments and combinations thereof.

Carbohydrate antigens can include, but are not limited to, the A blood group antigen, the B blood group antigen, the O blood group antigen, the Galili antigen (Gal-α-(1→3)-Gal), and fragments and combinations thereof. Of course, one of skill in the art will appreciate that any carbohydrate antigen that may be immunogenic can be used.

Figure 2:
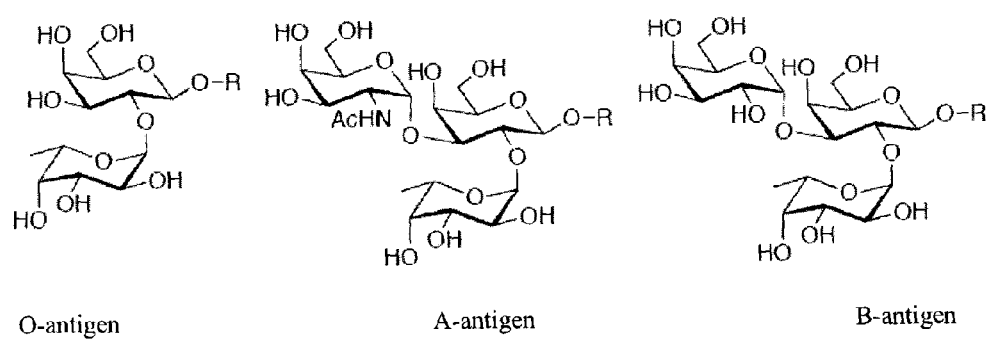
FIG. 2 is a schematic diagram of the ABO blood group antigens that can be used in one embodiment of the present invention.

The chemical structures of the ABO blood group antigens are shown in FIG. 2. The ABO blood group antigens may be further classified by the type of linkage connecting them to the remainder of the glycan motif. As shown in Table 1, six different families have been identified, termed Type I to Type VI based on the monosaccharide residue and position to which the reducing end β-galactoside moiety is linked. For example, which is not meant to be limiting, the A Type I antigen is the A-trisaccharide linked β-(1→3) to a N-acetyl-glucosamine (GlcNAc) residue, which is then attached through glycans of diverse structure to the protein or lipid in the human body. All types are meant to be included within the scope of this invention as useful antigens for the preparation of tolerogen 1.

TABLE 1

Definition of Type I to Type VI blood group structures

| Type | Definition |
| --- | --- |
| Type I | β-Galp-(1→3)-β-GlcpNAc-(1→ |
| Type II | β-Galp-(1→4)-β-GlcpNAc-(1→ |
| Type III | β-Galp-(1→3)-α-GalpNAc-(1→ |
| Type IV | β-Galp-(1→3)-β-GalpNAc-(1→ |
| Type V | β-Galp-(1→3)-β-Galp-(1→ |
| Type VI | β-Galp-(1→4)-β-Glcp-(1→ |

To facilitate the production of tolerogen 1 of the present invention, many different chemical synthesis protocols are currently available for the production of carbohydrate antigens. For example, which is not meant to be limiting, the ABO-blood group antigens of all six types can easily be produced in gram to kilogram quantities using techniques known in the art. Several procedures have now been published that teach the synthesis of these antigens and include publications by Zhang et al. (Zhang, Y., Yao, Q., Xia, C. et al. *Chem. Med. Chem.* 2006, 1:1361), Pazynina et al. (Pazynina, G. V., Tyrtysh, T. V., Bovin, N. V. *Mendeleev Commun.*, 2002, 12:143), and Meloncelli et al. (Meloncelli, P. J., Lowary, T. L. *Aust. J. Chem.*, 2009, 62:558).

In one embodiment, the antigenic full-length protein can include, but is not limited to, human leukocyte antigens (HLA). There are two main classes of HLA molecules. Class I comprises HLA-A, HLA-B, HLA-C and subtypes. Class II comprises DR, DQ, and subtypes. Either class of HLA can be used as antigen 2. Of course, as will be appreciated by one of skill in the art, fragments of HLA molecules could also be used as antigen 2 in the present invention.

HLA molecules and fragments thereof can easily be produced using recombinant technology. One of skill in the art will appreciate that many different techniques are available to produce and purify recombinant proteins such as HLA molecules. For example, which is not meant to be limiting, any of the techniques listed and described in *Molecular Cloning: A Laboratory Manual* (Sambrook, J. and Russell, D. W., CSHL Press, Cold Spring Harbor, N.Y., 3rd Edition, 2001) can be readily used to produce recombinant protein for the purposes of this invention.

Linker 3 can be selected from the group consisting of an aglycone comprising an anchoring group which can be, but is not limited to, the trialkoxysilyl group or a trihalosilyl group. In one embodiment, linker 3 has a trimethoxysilyl anchoring group. In one embodiment, linker 3 has a trichlorosilyl anchoring group. In one embodiment, the anchoring group can be —Si(OR)$_x$R$^2$$_y$, where R is an alkyl group, which can be methyl, ethyl, propyl or butyl;

where R$^2$ can be selected from the group consisting of an alkyl group, which can be methyl, ethyl, propyl, or butyl, and halogens, which can be, but is not limited to, I, Br, or Cl;

where x=0, 1, 2 or 3;

and where y=0, 1, or 2 if R$^2$ is an alkyl group, and where y=0, 1, 2 or 3 if R$^2$ if a halogen, wherein x+y must equal 3.

Of course, one of skill in the art will appreciate that many different linkers can be used to couple antigen 2 to carrier 4. For example, which is not meant to be limiting, the linker can selected from the group consisting of:

—O(CH$_2$)$_8$S(CH$_2$)$_3$Si(OR)$_x$R$^2$$_y$;

—O(CH$_2$)$_8$SO$_2$(CH$_2$)$_3$Si(OR)$_x$R$^2$$_y$;

—O(CH$_2$)$_7$CH$_2$Si(OR)$_x$R$^2$$_y$;

—O(CH$_2$)$_8$C(=O)NH(CH$_2$)$_3$Si(OR)$_x$R$^2$$_y$; and

—O(CH$_2$)$_8$S(CH$_2$)$_3$Si(OR)$_x$R$^2$$_y$, where R is an alkyl group, which can be methyl, ethyl, propyl, or butyl;

where R$^2$ can be selected from the group consisting of an alkyl group, which can be methyl, ethyl, propyl, or butyl, and halogens, which can be, but is not limited to, I, Br, or Cl;

where x=0, 1, 2 or 3;

and where y=0, 1, or 2 if R$^2$ is an alkyl group, and where y=0, 1, 2 or 3 if R$^2$ if a halogen, wherein x+y must equal 3.

Carrier 4 can be selected from the group consisting of a silica-coated stent, an Al$_2$O$_3$-coated stent, a SiO$_2$ nanoparticle, or a silica-coated iron oxide (Fe$_3$O$_4$) nanoparticle. As will be appreciated by one of skill in the art, the choice between stents or nanoparticles will vary depending on the intended application.

Stents and nanoparticles can be coated with silica or alumina in order to facilitate the coupling of at least one antigen 2 to carrier 4. Other functions of the silica or alumina coating include, but are not limited to, passivating the material and extending the half-life of carrier 4 in the body. The coating of the carrier with silica or alumina can be performed as taught by the prior art. For example, which is not meant to be limiting, silica coating of stainless steel stents can be carried out as taught by Meth and Sukenik (Meth, S., Sukenik, C. M. *Thin Solid Films*, 2003, 425:49) or as taught by Shapiro et al. (Shapiro, L., Marx, S., Mandler, D. *Thin Solid Films*, 2007, 515:4624-4628). Additionally, both silica and alumina coatings can be achieved on stainless steel through the use of atomic layer deposition (ALD). Alternatively, silica-coated nanoparticles can be achieved by incorporation into the Stöber synthesis (Stöber, W., Fink, A., Bohm, A. J. *Colloid Interface Sci.*, 1968, 26:62-69). Of course, as one of skill in the art will appreciate, the thickness of the silica or alumina coating can be varied for the intended application.

Nanoparticles can be selected from the group that includes, but is not limited to, silica (SiO$_2$) nanoparticles and silica-coated iron oxide (Fe$_3$O$_4$) nanoparticles. Both types of nanoparticles can be synthesized in sufficient quantities by using several techniques taught in the prior art. These techniques include, but are not limited to techniques taught by Tan et al. (Tan, W., Wang, K., He, H., et al. *Medicinal Research Reviews* 2004, 24:621-638), Aliev et al. (Aliev, F. G., Correa-Duarte, M. A., Mamedov, A., et al. *Adv. Mater.* 1999, 11:1006-1010), Ma et al. (Ma, D., Guan, J., Normandin, F., et al. *Chem. Mater.* 2006, 18:1920-1927), and Lee et al. (Lee, J., Lee, Y., Youn, J. K., et al. *Small*, 2008, 4:143-152).

Figure 3:
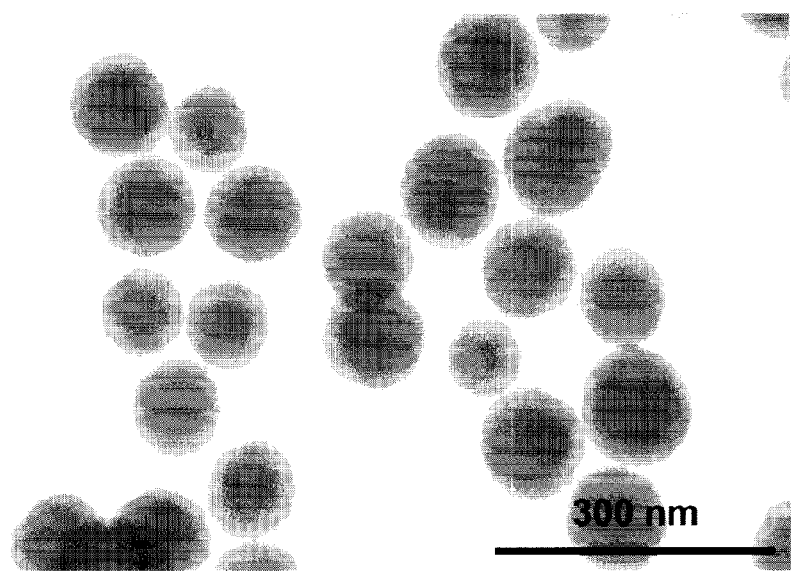
FIG. 3 is a scanning electron microscopy image in transmission mode of $SiO_2$ nanoparticles that can be used as a carrier in one embodiment of the present invention.

In one embodiment, SiO$_2$ nanoparticles can be used as carrier 4 (FIG. 3). The size of the nanoparticles can vary widely, and one of skill in the art will appreciate that optimal nanoparticle size will be determined by the intended application. Moreover, depending on the type of application, a monodisperse or polydisperse mixture of nanoparticles can be used. SiO$_2$ nanoparticles that can be used within the scope of this invention can be synthesized using techniques of the prior art, which can include, but is not limited to, the Stöber method (Stöber, W., Fink, A., Bohm, A. J. *Colloid Interface Sci.*, 1968, 26:62-69).

In one embodiment, silica-coated Fe$_3$O$_4$ nanoparticles can be used as carrier 4. The size of the nanoparticles can vary widely, and one of skill in the art will appreciate that optimal nanoparticle size will be determined by the intended application. Moreover, depending on the type of application, a monodisperse or polydisperse mixture of nanoparticles can be used.

Figure 4A:
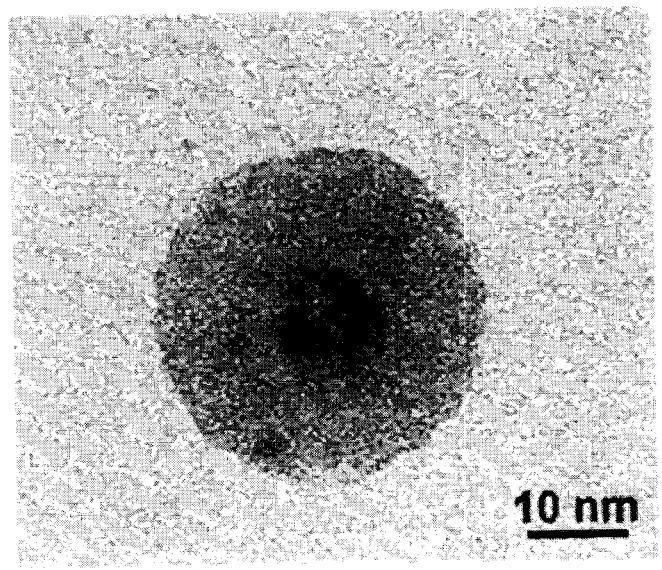
FIG. 4A is a bright field transmission electron microscopy image of $Fe_3O_4$—$SiO_2$ core-shell nanoparticles that can be used as a carrier in one embodiment of the present invention.
Figure 4B:
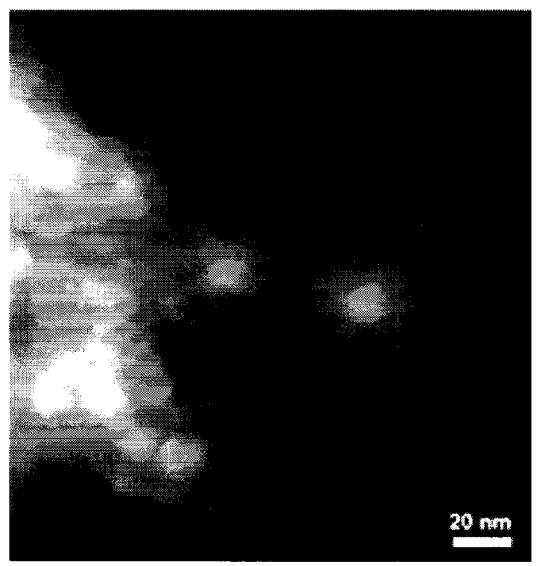
FIG. 4B is a high annular dark field transmission electron microscopy image of $Fe_3O_4$—$SiO_2$ core-shell nanoparticles that can be used as a carrier in one embodiment of the present invention.

Silica-coated Fe$_3$O$_4$ nanoparticles (FIGS. 4A and 4B) that can be used within the scope of this invention can be synthesized using techniques of the prior art. For example, which is not meant to be limiting, silica-coated Fe$_3$O$_4$ nanoparticles can be synthesized according to the teachings of Lee et al. (Lee, J., Lee, Y., Youn, J., et al. *Small*, 2008, 4:143-152). These nanoparticles can be coated with a continuous or complete thin sheath of silica to extend the half-life of these nanoparticles in the blood. Because of the core-shell structure of these nanoparticles, they are magnetic and may have several advantages, including, but not limited to, site-directed delivery with a magnetic or electric field and utility in magnetic resonance imaging.

In one embodiment, a stent may be used as carrier 4. As one of skill in the art will appreciate, the size of the stent will vary with the intended application. The size of the patient in which the stent will be inserted and the location of the stent will be important factors in determining the appropriate stent size.

Moreover, as one of skill in the art will appreciate, many different biocompatible materials can be used to prepare stents for the purposes of this invention. For example, which is not meant to be limiting, the stent can be made from 316L stainless steel, titanium, titanium alloys, and cobalt chromium alloys.

In one embodiment, the stent is made from 316L stainless steel due to its low rate of corrosion, good biocompatibility and low toxicity. 316L stainless steel stents can first be passivated with a thin silica or alumina coating, laden with the necessary hydroxyl groups to permit surface functionalization. As mentioned above, the addition of this thin silica or alumina coating can be performed using prior art techniques.

The tolerogens compositions of the present invention can be constructed through a variety of means known to persons skilled in the art. Antigen 2 can be coupled to carrier 4 through linker 3 in a variety of different ways. Several techniques are currently available and include those taught by Lemieux et al. (U.S. Pat. No. 4,362,720, U.S. Pat. No. 4,137,401, U.S. Pat. No. 4,238,473), and Terunuma et al. (WO2007 JP53318).

As discussed above, the silica or alumina coating of carrier 4 can be helpful for the attachment of linker 3 and antigen 2 to carrier 4. As mentioned above, different types of linker 3 can be used to tailor the surface(s) of carrier 4 with the necessary functional groups to covalently couple antigen 2. As one of skill in the art will appreciate, many different functional groups can be used.

Figure 5:
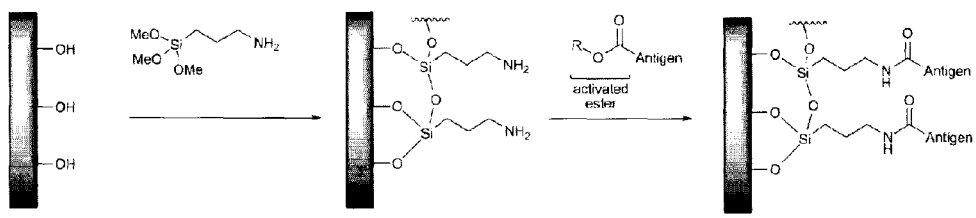
FIG. 5 is a schematic diagram of a silica or alumina-coated stent carrier whose surface has been functionalized with amino groups to allow for coupling with activated ester derivatives of antigens, according to one embodiment of the present invention.
Figure 8:
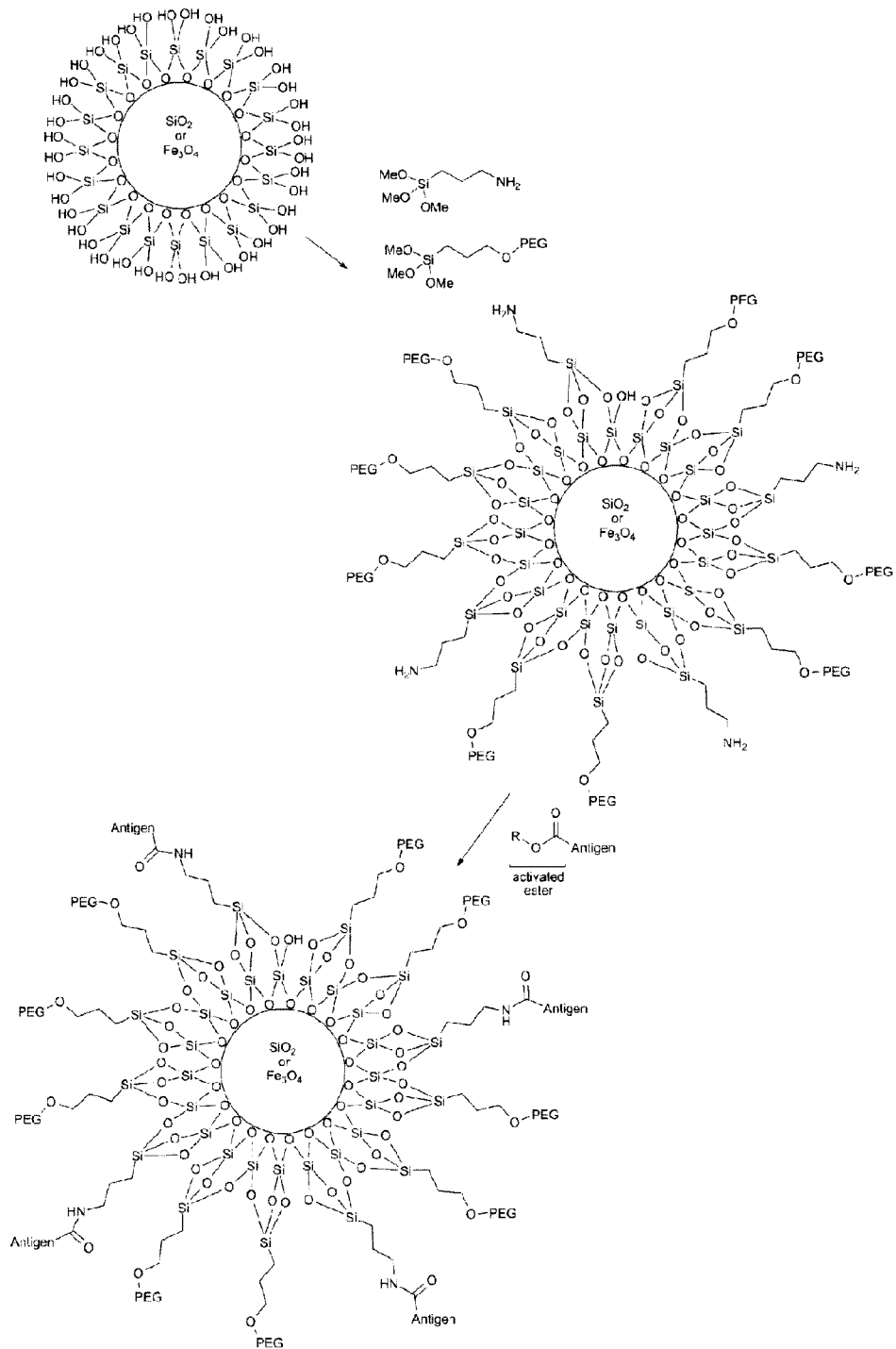
FIG. 8 is a schematic representation of a silica-coated $Fe_3O_4$ nanoparticle or a $SiO_2$ nanoparticle, whose surface has been functionalized with amino groups to allow for coupling with activated ester derivatives of antigens, according to one embodiment of the present invention.

In one embodiment, carrier 4 (FIG. 5 and FIG. 8) could be functionalized with amino groups through the use of $H_2N(CH_2)_3Si(OMe)_3$ as linker 3. Without wishing to be bound by theory, the presence of an amino group allows for an activated ester of antigen 2 to be coupled to carrier 4. Of course, as one of skill in the art will appreciate, $H_2N(CH_2)_3Si(OR)_xR^2_y$ can also be used depending on the intended application, where:

R is an alkyl group, which can be methyl, ethyl, propyl, or butyl;

$R^2$ can be selected from the group consisting of an alkyl group, which can be methyl, ethyl, propyl, or butyl, and halogens, which can be, but is not limited to, I, Br, or Cl;

x=0, 1, 2 or 3;

and y=0, 1, or 2 if $R^2$ is an alkyl group, and where y=0, 1, 2 or 3 if $R^2$ if a halogen, wherein x+y must equal 3.

Figure 6:
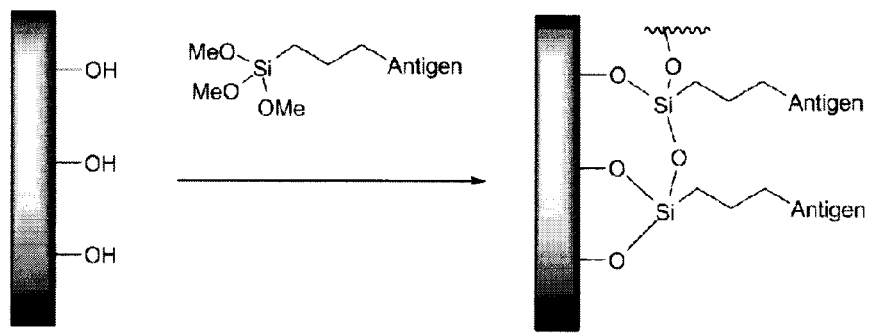
FIG. 6 is a schematic diagram of a silica or alumina-coated stent carrier, whose surface has been functionalized by direct attachment of the antigen to the hydroxyl groups of the silica or alumina coating, according to one embodiment of the present invention.
Figure 7:
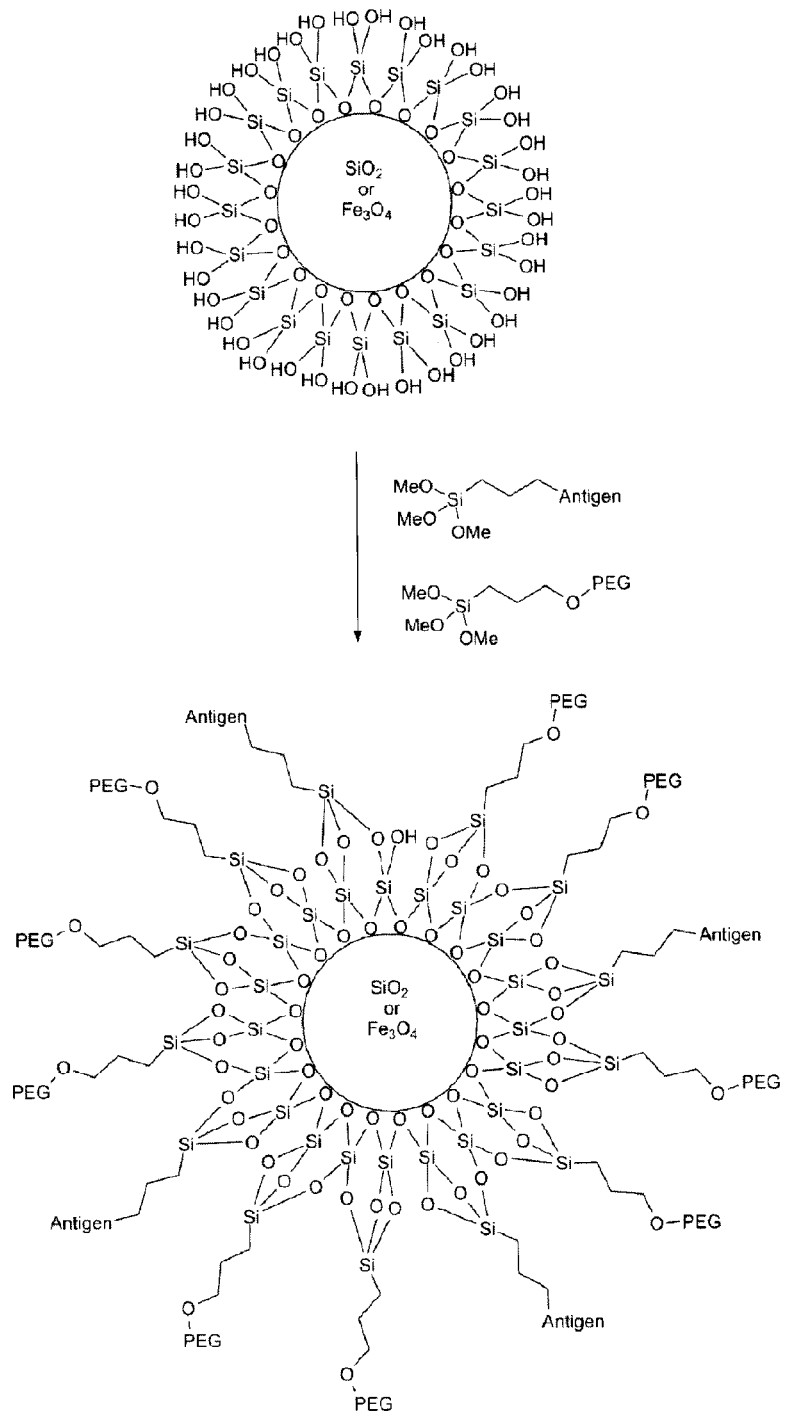
FIG. 7 is a schematic representation of a silica-coated $Fe_3O_4$ nanoparticle or a $SiO_2$ nanoparticle, whose surface has been functionalized by direct attachment of the antigen to the hydroxyl groups of the silica, according to one embodiment of the present invention.

In another embodiment, carrier 4 (FIG. 6 and FIG. 7) can be directly functionalized by the preparation of antigen 2 with a trimethoxysilyl $(Si(OCH_3)_3$ linker. Of course, as of one skill in the art will appreciate, a $—Si(OR)_xR^2_y$ linker can also be used depending on the intended application, where R is an alkyl group, which can be methyl, ethyl, propyl, or butyl;

$R^2$ can be selected from the group consisting of an alkyl group, which can be methyl, ethyl, propyl, or butyl, and halogens, which can be, but is not limited to, I, Br, or Cl;

x=0, 1, 2 or 3;

and y=0, 1, or 2 if $R^2$ is an alkyl group, and where y=0, 1, 2 or 3 if $R^2$ if a halogen, wherein x+y must equal 3.

Without wishing to be bound by theory, directly functionalizing antigen 2 may allow for an easier synthesis procedure, since there is no need for protection or deprotection of carbohydrate antigens. Further, this may allow for better control of the loading of antigen 2 onto carrier 4.

The number and type of antigen 2 molecules that can be attached to carrier 4 can vary widely. In one embodiment, tolerogen 1 comprises a plurality of antigen 2 molecules, wherein the antigen molecules correspond to the same type of antigen. In one embodiment, tolerogen 1 comprises a plurality of antigen 2 molecules, wherein the antigen molecules correspond to different types of antigen. For example, which is not meant to be limiting, all six permutations for a given ABO-blood group antigen can be coupled to carrier 4 to create tolerogen 1 and provide the patient with exposure to any of the structures likely to be encountered in a transplanted organ. In one embodiment, tolerogen 1 comprises both ABO-blood group antigens and HLA proteins. As one of skill in the art will appreciate, any combination of antigens or combinations of fragments of antigens can be used to prepare tolerogen 1 to allow for the induction of immunologic tolerance to non-self antigens.

The number of antigen 2 molecules coupled to carrier 4 may have to be varied depending on the intended application. It has been found that nanoparticles coated only with a dense overlayer of antigen 2 may be susceptible to opsonin adsorption, and subsequent rapid removal from the bloodstream. It has been established in the prior art that nanoparticles coated with either a hydrophilic monolayer or "cloud" or flexible polyethyleneglycol (PEG) molecules circulate with a longer half-life in the bloodstream, and belong to a class of particles termed "stealth particles" (FIG. 7 and FIG. 8) (Zillies, J. C., Zwiorek, K., Winter, G., et al. *Anal. Chem.*, 2007, 79:4574; Duguet, E., Vasseur, S., Mornet, S., et al. *Nanomed*, 2006, 1:157; Zahr, A. S., Davis, C. A., Pishko, M. V. *Langmuir*, 2006, 2:8178; Kirpotin, D. B., Drummond, D. C., Shao, Y., et al. *Cancer Res.*, 2006, 66:6732; Zahr, A. S., de Villiers, M., Pishko, M. V. *Langmuir*, 2005, 1:403; Peracchia, M. T., *Pharma Sciences*, 2003, 13:155; Beletsi, A., Panagi, Z., Avgoustakis, K. *Int. J. Pharmaceutics,* 2005, 298:233). Without wishing to be bound by theory, a stealth particle with an extended residence in plasma will permit greater contact between the antigens and circulating lymphocytes, decreasing the necessity for subsequent re-exposure to the nanoparticle solution.

In one embodiment, to increase the half-life in blood of tolerogen 1, nanoparticles are coated with a mixed layer of antigen 2 and an appropriate polyethylene glycol (PEG)-containing molecule that can have a surface binding group such as the —$Si(OR)_xR^2_y$ group, where R is an alkyl group, which can be methyl, ethyl, propyl, or butyl;

$R^2$ can be selected from the group consisting of an alkyl group, which can be methyl, ethyl, propyl, or butyl, and halogens, which can be, but is not limited to, I, Br, or Cl;

x=0, 1, 2 or 3;

and y=0, 1, or 2 if $R^2$ is an alkyl group, and where y=0, 1, 2 or 3 if $R^2$ if a halogen, wherein x+y must equal 3 (FIG. 8).

Without wishing to be bound by theory, this type of layer can dilute antigen 2 and surround the nanoparticles with PEG, thereby minimizing protein physisorption. The same effect has also been noted with stents, where PEG/antigen co-functionalization may be required to minimize biofouling, plasma protein physisorption, and biofilm formation. Of course, as one of skill in the art will appreciate, many other biofouling polymers can also be used and are meant to be included within the scope of the present invention.

A wide variety of different PEGs can be used to surround carrier 4. As one of skill in the art will appreciate, the length of the PEG chains can be varied to provide for an optimal level of protection, without hindering access to antigen 2. In one embodiment, a silane with a 3-carbon chain is bonded to a PEG chain with 6-9 or 9-12 repeat units and an O—R termination group, where R is an alkyl that can be selected from the group consisting of methyl, ethyl, propyl and butyl.

The concentration of antigen 2 and PEG in the mixed layer surrounding carrier 4 can vary. Of course, one of skill in the art will appreciate that the concentration of each component will vary depending on the intended application. At a minimum, carrier 4 should carry at least one antigen 2.

As discussed above, tolerogen 1 produced herein can be administered to a patient in order to suppress antigen-specific immune responses with no or less recourse to immunosuppressant therapy. Patients can vary widely in age and in health conditions. In one embodiment, the methods and systems for inducing immunologic tolerance to non-self antigens can be used in neonates prior to the maturation of the immune system. In another embodiment, the methods are systems can be used in patients who are growing past the age of infancy. The methods and systems of the present invention comprise administering to a patient tolerogen 1 to induce immunologic tolerance to non-self antigens. The selected non-self antigen can be attached to carrier 4, which can take the form of nanoparticles or a stent.

The administration of tolerogen 1 will depend upon the type of carrier 4 used to produce the tolerogen. In one embodiment, where carrier 4 is a stent, surgical implantation of tolerogen 1 will be required. The stent can be implanted in various locations in the body, so as to maximize the induction of immunologic tolerance to non-self antigens. In one embodiment, the stent can be implanted near an organ that has been transplanted or near a site that will receive a transplanted organ.

In another embodiment, where carrier 4 is a nanoparticle, intravenous administration of a composition of tolerogen 1 can be used. A tolerogen composition of the present invention can be formulated by combining tolerogen 1 with any pharmaceutically acceptable excipient as determined to be appropriate by those of skill in the art. Requirements for effective pharmaceutical excipients for intravenous compositions are well known to those of skill in the art and have been reported in many publications (*Pharmaceutical and Pharmacy Practice*, J.B. Lippincott Company, Philadelphia, Pa., Banker & Chalmers, Eds., 1982; *ASHP Handbook on Injectable Drugs*, Toissel, 4$^{th}$ Ed., 1986). Frequency of administration will vary according to intended application.

The following MATERIALS AND METHODS were used in the examples that follow. These materials and methods are for illustrative purposes only and are not to be construed as limiting the scope of the invention in any way. One of skill in the art will appreciate that several modifications and substitutions can be made without affecting the scope of the invention. More specifically, these include modifications and substitutions in the specific techniques and reaction conditions listed below.

General Methods

All reagents were purchased from commercial sources and were used without further purification, unless otherwise stated. Reaction solvents were purchased and were used without purification; dry solvents were purified by successive passage through columns of alumina and copper under nitrogen. All reactions were carried out at room temperature under a positive pressure of argon, unless otherwise stated. Thin layer chromatography (t.l.c.) was performed on Merck silica gel 60 $F_{254}$ aluminum-backed plates that were stained by heating (>200°) with either p-anisaldehyde in 5% sulfuric acid in ethanol or 10% ammonium molybdate in 10% sulfuric acid. Unless otherwise indicated, all column chromatography was performed on silica gel 60 (40-60 µM). Iatrobeads refers to a beaded silica gel 6RS-8060, which is manufactured by Iatron Laboratories (Tokyo). C-18 silica gel (35-70 µM) was manufactured by Toronto Research Chemicals. Optical rotations were measured at 22±2° C. $^1$H NMR spectra were recorded at 400 and 500 MHz, and chemical shifts were referenced to the peak for TMS (0.0 ppm, $CDCl_3$) or $CD_3OD$ (3.30 ppm, $CD_3OD$). $^{13}$C NMR (APT) spectra were recorded at 125 or 100 MHz, and $^{13}$C chemical shifts were referenced to the peak for internal $CDCl_3$ (77.1 ppm, $CDCl_3$) or $CD_3OD$ (49.0, $CD_3OD$). All spectra were recorded in $CDCl_3$ unless specified otherwise. Melting points were measured using a PerkinElmer Thermal Analysis. Electrospray mass spectra were recorded on samples suspended in mixtures of THF with $CH_3OH$ and added NaCl.

Hydrofluoric acid and sulphuric acid were purchased from J. T. Baker and used as received. Hydrogen peroxide was purchased from Fischer Scientific and used as received. Acetic acid was purchased from EMD and used as received. Ethanol (95%) was purchased from Fisher Scientific and used as received. 3-Mercaptopropyl trimethoxysilane (MPTMS) was purchased from Aldrich and used as received. 2-[Methoxy(polyethyleneoxy)propyl]-trimethoxysilane was purchased from Gelest Inc. (Morrisville, Pa., U.S.A.) and used as received. 18 MΩ (Barnstead) water was freshly generated before use. Palmaz-Schatz PS204C balloon expandable stainless steel stents were obtained from Johnson & Johnson (Miami, Fla.).

For the biological assays, PBST refers to a phosphate buffer saline solution at pH 7.4, containing 0.1% Tween-20. Phosphate buffer saline consists of a solution of 137 mM NaCl, 2.7 mM KCl, 100 mM $Na_2HPO_4$, and 2 mM $KH_2PO_4$ in deionized water. The OPD indicator was purchased from Aldrich (SIGMAFAST OPD P9187) and prepared according to the manufacturer's instructions. Absorbance was measured at 450 nm on a Molecular Devices SPECTRAmax 340PC UV/Vis spectrophotometer. Fluorescence was measured on a Molecular Devices SpectraMax M2 microplate reader. The peroxidase conjugated lectins (WGA-L3892 and PNA-L7759) were purchased from Aldrich and used without modification. The FITC conjugated lectins (WGA-L4895 and PNA-L7381) were also purchased from Aldrich and used without modification. The Anti-A mouse IgM was purchased from Virogen (Anti-A1, A2, A3 Cat#133-A), whereas the secondary goat anti-mouse IgM HRP antibody was purchased from Southern Biotech (1021-05).

Stent surfaces were characterized by scanning Auger microscopy (SAM), X-ray photoelectron spectroscopy (XPS), and a peroxidase biological assay. Nanoparticles were characterized by XPS, scanning electron microscopy (SEM), transmission electron microscopy (TEM), and atomic force microscopy (AFM). SAM, and XPS were performed under high-vacuum conditions (<$10^{-8}$ Torr). XPS (Kratos Analytical, Axis-Ultra) was performed using monochromatic Al KR with a photon energy of 1486.6 eV, in the Alberta Centre for Surface Engineering and Science (ACSES). The instrument was calibrated on the basis of the C 1s peak. SAM (JAMP-9500F, JEOL) was performed at 15 kV and 8 nA, for the accelerating voltage and emission current, respectively. SEM was carried out using a Hitachi S-4880 FE-SEM operating at 5-15 kV, and TEM with a JEOL 2010 microscope operating at 200 kV. AFM was performed using a Nanoscope IV (Digital Instruments/Veeco) using commercial Si cantilevers.

In order that the invention be more fully understood, the following examples are set forth. These examples are for illustrative purposes only and are not to be construed as limiting the scope of the invention in any way. Moreover, these examples are not intended to exclude equivalents and variations of the present invention, which are apparent to one skilled in the art.

Preparation of Antigens and Carbohydrates for Stainless Steel Stents and Nanoparticles According to Various Embodiments of the Present Invention Example 1

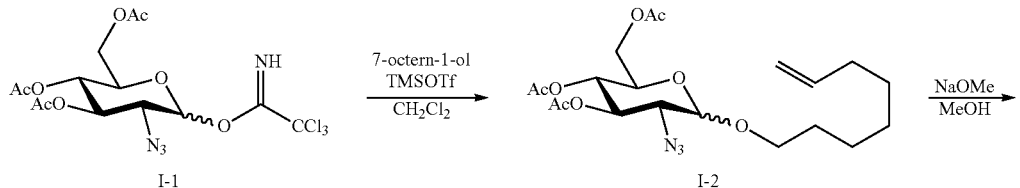

-continued
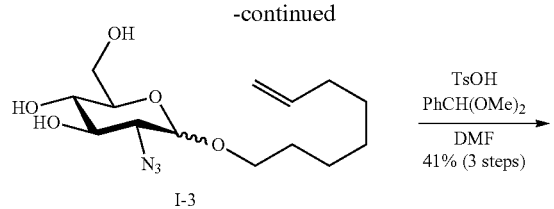
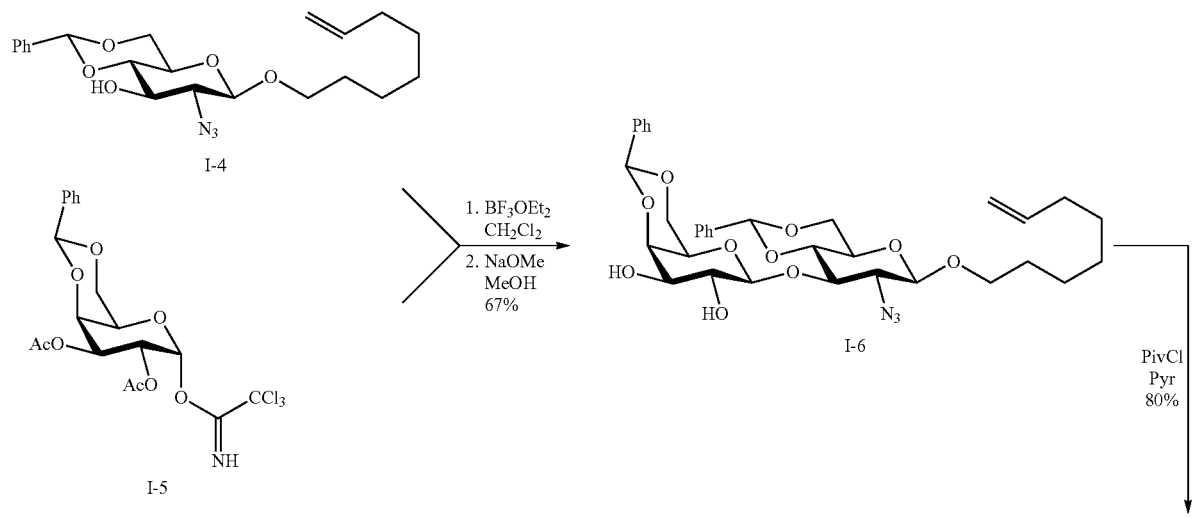
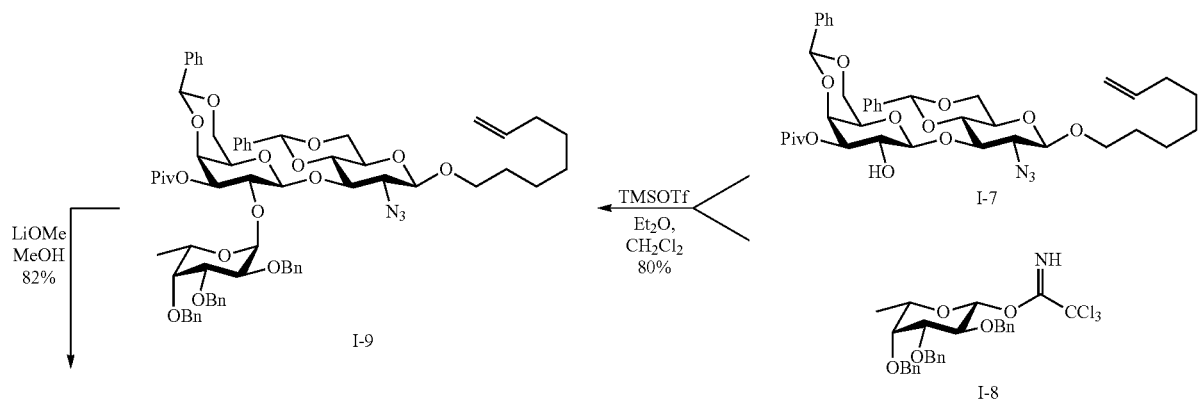
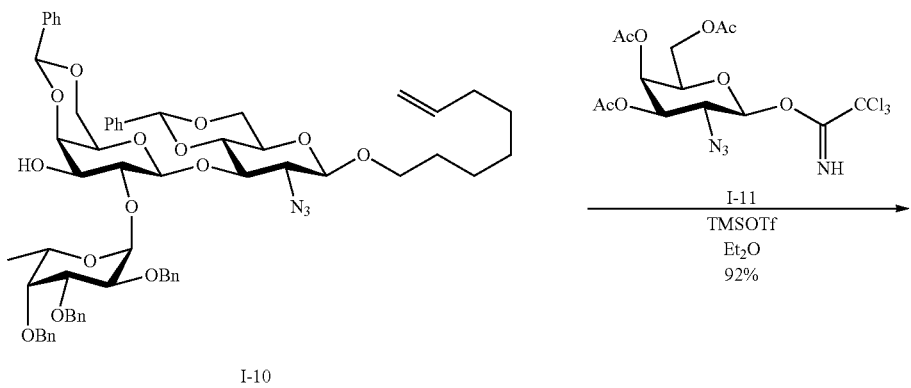

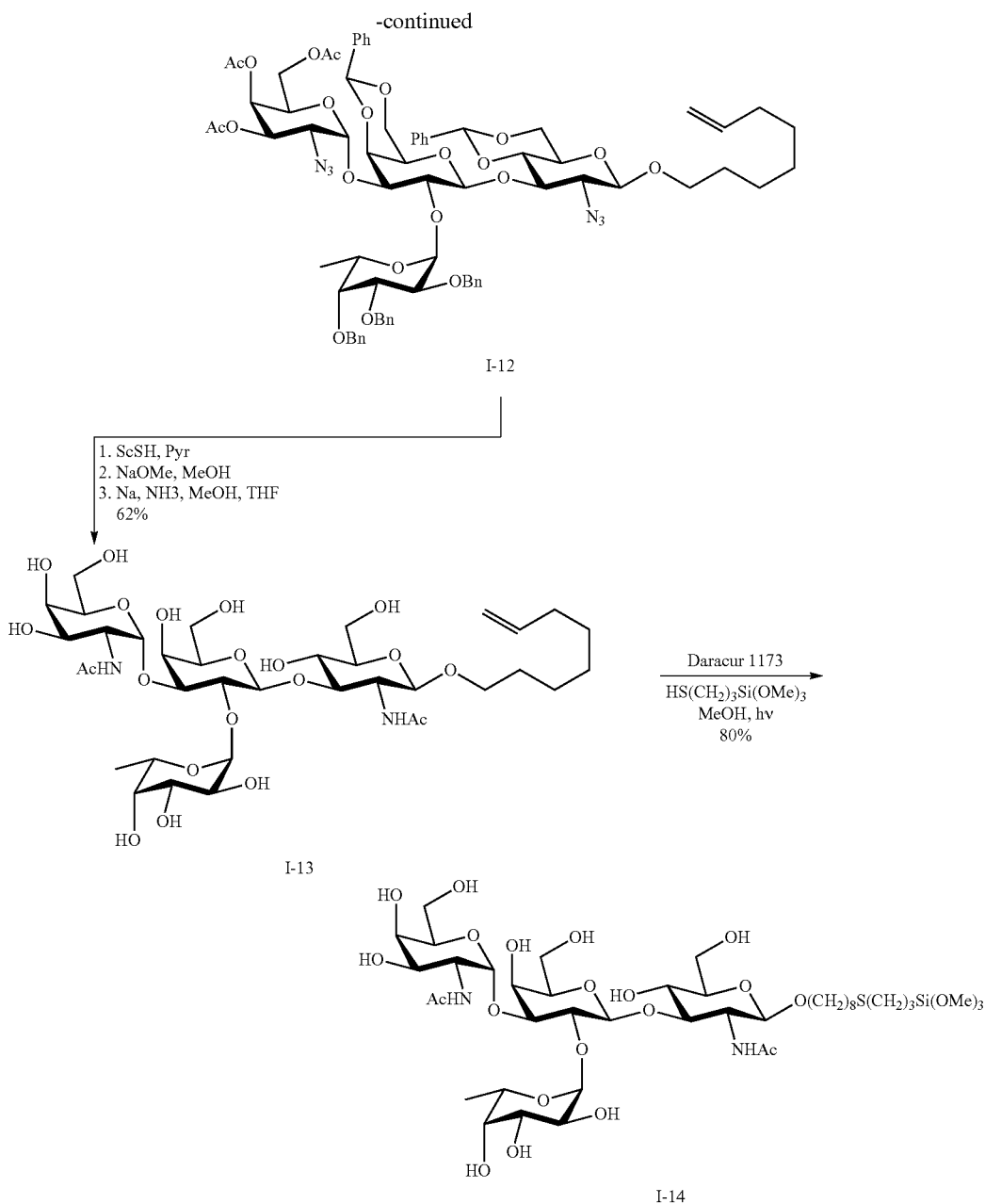

Synthesis of 7-Octen-1-yl 2-Azido-4,6-O-benzylidene-2-deoxy-β-D-glucopyranoside (I-4)

A stirred solution of trichloroacetimidate I-1 (Rele, S. M., Iyer, S. S., Baskaran, S., et al. *J. Org. Chem.*, 2004, 69:9159-9170) (8.69 g, 18.3 mmol) and 7-octen-1-ol (2.82 g, 22.0 mmol) in dry $CH_2Cl_2$ (50 mL) was treated with 4 Å molecular sieves (3.5 g) and the mixture stirred (rt, 1 h). The mixture was cooled (−30° C.), treated with TMSOTf (300 μL) and allowed to slowly warm (0° C.). The mixture was neutralized with $Et_3N$ (1 mL), filtered, concentrated and subjected to flash chromatography (EtOAc/Hexanes, 1:3) to give an inseparable α/β mixture I-2 used immediately in the subsequent step. The oil was taken up in $CH_3OH$ (80 mL) and treated with a catalytic amount of $NaOCH_3$ in $CH_3OH$ and the solution stirred (rt, 1 h). The solution was then neutralized with Amberlite IR120 and the mixture filtered; concentration followed by flash chromatography (EtOAc/Hexanes, 2:1) to yield the triol I-3 (3.32 g) as an inseparable α/β mixture. A solution of the triol (3.32 g, 10.5 mmol) in dry DMF (20 mL) was treated with benzaldehyde dimethyl acetal (2.13 g, 14.0 mmol) and TsOH (100 mg) and the solution stirred (50° C., 4 h). The solution was treated with $Et_3N$ (1 mL), concentrated and subjected to flash chromatography (EtOAc/Hexanes, 1:3) to afford the β-glycoside I-4 as a colourless oil (3.05 g, 41%). [α]−38.4 (c=0.4, $CH_2Cl_2$); $R_f$ 0.18 (EtOAc/hexanes, 7:3); $^1$H NMR (500 MHz): $\delta_H$ 7.52-7.35 (5H, m, Ph), 5.87-5.76 (1H, m, $CH=CH_2$), 5.54 (1H, s, PhCH), 5.04-4.92 (2H, m, $CH=CH_2$), 4.42 (1H, d, $J_{1,2}$ 8.0, H1), 4.34 (1H, dd, $J_{6,6}$ 10.3, $J_{5,6}$ 5.0, H6), 3.97-3.89 (1H, m, $CH=CH_2(CH_2)_5CH_2O$), 3.79 (1H, dd, $J_{6,6}$ 10.3, $J_{5,6}$ 10.3, H6), 3.69-3.51 (3H, m, H3, H4, $CH=CH_2(CH_2)_5CH_2O$), 3.45-3.35 (2H, m, H2, H5), 2.69 (1H, brs, OH), 2.10-1.99, 1.73-1.56, 1.46-1.25 (10H, m, CH=CH$_2$(CH$_2$)$_5$CH$_2$O). $^{13}$C NMR (125 MHz): δ$_C$ 139.0 (CH=CH$_2$), 136.8 (Ph), 129.4 (Ph), 128.4 (Ph), 126.2 (Ph), 114.3 (CH=CH$_2$), 102.7, 102.0 (PhCH, C1), 80.6, 72.0, 66.5, 66.2 (C2, C3, C4, C5), 70.7 (CH=CH$_2$(CH$_2$)$_5$CH$_2$O), 68.5 (C6), 33.7 (CH=CH$_2$(CH$_2$)$_5$CH$_2$O), 29.5 (CH=CH$_2$(CH$_2$)$_5$CH$_2$O), 28.81 (CH=CH$_2$(CH$_2$)$_5$CH$_2$O), 28.78 (CH=CH$_2$(CH$_2$)$_5$CH$_2$O), 25.8 (CH=CH$_2$(CH$_2$)$_5$CH$_2$O). ESI MS: m/z calcd [C$_{21}$H$_{29}$N$_3$O$_5$]Na$^+$: 426.2000. Found 426.2002.

Synthesis of 7-Octen-1yl 2-Azido-4,6-O-benzylidene-3-O-(4,6-O-benzylidene-3-O-pivaloyl-β-D-galactopyranosyl)-2-deoxy-β-D-glucopyranoside (I-7)

A solution of the acceptor I-4 (1.02 g, 2.53 mmol) in dry CH$_2$Cl$_2$ (50 mL) was stirred over 4 Å molecular sieves (3 g) (rt, 1 h). The solution was then cooled (−40° C.), treated with TMSOTf (0.1 mL) followed by drop-wise addition of the trichloroacetimidate (Figueroa-Pérez, S., Vérez-Bencomo, V. *Carbohydr. Res.* 1999, 317:29-38) (I-5) (4.4 g, 8.9 mmol) and then the mixture allowed to warm (0° C.). The mixture was neutralized with Et$_3$N (1 mL), concentrated and subjected to flash chromatography (EtOAc/hexanes, 1:1) to afford a colourless oil, which was immediately used in the next step. The colourless oil was taken up in CH$_3$OH (100 mL), treated with a solution of NaOCH$_3$ in CH$_3$OH and stirred (rt, 3 h). The solution was neutralized with Amberlite IR 120 (H$^+$), filtered and subjected to flash chromatography (EtOAc/hexanes, 7:3) to afford the somewhat pure diol I-6 as a colourless oil (1.20 g, 67%). The diol (1.20 g, 1.83 mmol) was then taken up in dry pyridine (25 mL) and treated with trimethylacetyl chloride (600 mg, 5.0 mmol) and the solution stirred (rt, 3 h). The solution was then concentrated and the residue subjected to flash chromatography (EtOAc/Hexanes, 1:3) to afford the alcohol I-7 (1.08 g, 80%) as a colorless oil. [α]+5.8 (c=0.1, CH$_2$Cl$_2$); R$_f$ 0.75 (EtOAc/hexanes, 2:3); $^1$H NMR (500 MHz): δ$_H$ 7.52-7.46, 7.38-7.30 (10H, m, Ph), 5.86-5.76 (1H, m, CH$_2$=CH), 5.54, 5.46 (2H, 2×s, PhCH), 5.04-4.92 (2H, m, CH$_2$=CH), 4.78 (1H, dd, J$_{2',3'}$ 9.5, J$_{3',4'}$ 3.6, H3'), 4.49 (1H, d, J$_{1',2'}$ 7.9, H1"), 4.47 (1H, d, J$_{1,2}$ 8.0, H1), 4.37-4.29 (2H, m, H4', H6), 4.17 (1H, d, J$_{6',6'}$ 12.1, H6'), 4.05 (1H, dd, J$_{2',3'}$ 9.5, J$_{1',2'}$ 8.2, H2'), 3.96-3.88 (2H, m, H6', CH=CH$_2$(CH$_2$)$_5$CH$_2$O), 3.80 (1H, dd, J$_{6,6}$ 10.1, J$_{5,6}$ 10.1, H6), 3.77-3.72 (2H, m, H3, H4), 3.62-3.49 (2H, m, H2, CH=CH$_2$(CH$_2$)$_5$CH$_2$O), 3.46-3.35 (1H, m, H5), 3.33-3.29 (1H, m, H5'), 3.02-2.96 (1H, brs, OH), 2.11-2.01 (2H, CH=CH$_2$(CH$_2$)$_5$CH$_2$O), 1.72-1.60 (2H, CH=CH$_2$(CH$_2$)$_5$CH$_2$O), 1.46-1.30 (6H, CH=CH$_2$(CH$_2$)$_5$CH$_2$O), 1.22 (9H, s, (CH$_3$)$_3$C). $^{13}$C NMR (125 MHz): δ$_C$ 178.3 (C=O), 139.0 (CH=CH), 137.9 (Ph), 137.0 (Ph), 129.1 (Ph), 128.7 (Ph), 128.2 (Ph), 128.0 (Ph), 126.02 (Ph), 125.96 (Ph), 114.3 (CH$_2$=CH), 104.5 (C1'), 102.7 (C1), 101.4 (PhCH), 100.5 (PhCH), 79.9, 79.8 (C3, C4), 73.21, 73.20 (C3', C4'), 70.8 (CH=CH$_2$(CH$_2$)$_5$CH$_2$O), 69.1 (C2'), 68.8, 68.5 (C6, C6'), 67.0 (C5'), 66.3 (C5), 65.5 (C2), 39.0 ((CH$_3$)$_3$C), 33.7 (CH=CH$_2$(CH$_2$)$_5$CH$_2$O), 29.5 (CH=CH$_2$(CH$_2$)$_5$CH$_2$O), 28.80 (CH=CH$_2$(CH$_2$)$_5$CH$_2$O), 28.77 (CH=CH$_2$(CH$_2$)$_5$CH$_2$O), 27.1 ((CH$_3$)$_3$C), 25.7 (CH=CH$_2$(CH$_2$)$_5$CH$_2$O). ESI MS: m/z calcd [C$_{44}$H$_{59}$N$_3$O$_{13}$]Na$^+$: 760.3416. Found 760.3415.

Synthesis of 7-Octen-1yl 2-Azido-4,6-O-benzylidene-3-O-(4,6-O-benzylidene-3-O-pivaloyl-2-O-(2,3,4-tri-O-benzyl-α-L-fucopyranosyl)-β-D-galactopyranosyl)-2-deoxy-β-D-glucopyranoside (I-9)

A solution of the acceptor I-7 (415 mg, 0.563 mmol) in dry Et$_2$O/CH$_2$Cl$_2$ (90:10, 20 mL) was stirred over 4 Å molecular sieves (rt, 1 h). The mixture was then cooled (−10° C.), treated with TMSOTf followed by drop-wise addition of the trichloroacetimidate (Schmidt, R. R., Toepfer, A. *J. Carb. Chem.* 1993, 12:809-822) (I-8) (1.02 g, 13.8 mmol) in dry Et$_2$O (15 mL) and the mixture stirred (20 min). The mixture was treated with Et$_3$N (0.5 mL), filtered and subjected to flash chromatography (EtOAc/Hexanes, 1:3) to yield the trisaccharide I-9 as a colourless oil (510 mg, 80%). [α]−20.7 (c=0.2, CH$_2$Cl$_2$); R$_f$ 0.59 (EtOAc/hexanes, 3:7); $^1$H NMR (500 MHz): δ$_H$ 7.55-7.22 (25H, m, Ph), 5.87-5.77 (1H, m, CH$_2$=CH), 5.41 (1H, d, J$_{1'',2''}$ 1.5, H1"), 5.48 (1H, s, PhCH), 5.37 (1H, s, PhCH), 5.04-4.92 (4H, m, H3', PhCH$_2$, CH$_2$=CH), 4.79, 4.74 (2H, AB, J 11.5, PhCH$_2$), 4.76 (1H, d, J$_{1',2'}$ 8.1, H1"), 4.69 (1H, A of AB, J 11.7, PhCH$_2$), 4.79, 4.63 (2H, AB, J 11.5, PhCH$_2$), 4.51 (1H, q, J$_{5'',6''}$ 6.3, H5"), 4.42 (1H, d, J$_{1,2}$ 7.7, H1), 4.34-4.29 (2H, m, H6, H6'), 4.24 (1H, d, J$_{1',2'}$ 8.5, J$_{2',3'}$ 8.5, H2'), 4.13-4.07 (3H, m, H2", H3", H4'), 3.97-3.91 (1H, m, CH=CH$_2$(CH$_2$)$_5$CH$_2$O), 3.83-3.70 (5H, m, H3, H4, H4', H6, H6'), 3.63-3.56 (1H, m, CH=CH$_2$(CH$_2$)$_5$CH$_2$O), 3.43-3.35 (2H, m, H2, H5), 3.04-2.99 (1H, m, 5'), 2.11-2.03 (2H, m, CH=CH$_2$(CH$_2$)$_5$CH$_2$O), 1.73-1.63 (2H, m, CH=CH$_2$(CH$_2$)$_5$CH$_2$O), 1.46-1.31 (6H, m, CH=CH$_2$(CH$_2$)$_5$CH$_2$O), 1.20 (3H, d, J$_{5'',6''}$ 6.3, H6"), 1.08 (9H, s, (CH$_3$)$_3$C). $^{13}$C NMR (125 MHz): δ$_C$ 177.9 (C=O), 139.01 (Ph), 138.98 (CH$_2$=CH), 138.6 (Ph), 138.4 (Ph), 137.6 (Ph), 136.8 (Ph), 129.2 (Ph), 128.7 (Ph), 128.5 (Ph), 128.4 (Ph), 128.33 (Ph), 128.28 (Ph), 128.2 (Ph), 128.0 (2C, Ph), 127.6 (Ph), 127.5 (Ph), 127.44 (Ph), 127.38 (Ph), 126.2 (2C, Ph), 114.3 (CH$_2$=CH), 102.8 (C1), 101.05 (C1'), 101.7 (PhCH), 100.8 (PhCH), 96.8 (C1'), 79.9, 79.7, 78.0, 77.5, 76.55, 76.52 (C3, C3', C3", C4, C4', C4"), 75.0 (PhCH$_2$), 73.5 (PhCH$_2$), 72.9 (PhCH$_2$), 72.6, 70.1 (C2', C2"), 70.7 (CH=CH$_2$(CH$_2$)$_5$CH$_2$O), 68.8, 68.6 (C6, C6"), 66.5 (C5"), 66.4, 65.9, 65.7 (C2, C5, C5'), 38.8 ((CH$_3$)$_3$C), 27.0 ((CH$_3$)$_3$C), 33.7 (CH=CH$_2$)$_5$CH$_2$O), 29.5 (CH=CH$_2$(CH$_2$)$_5$CH$_2$O), 28.83 (CH=CH$_2$(CH$_2$)$_5$CH$_2$O), 28.78 (CH=CH$_2$(CH$_2$)$_5$CH$_2$O), 25.8 (CH=CH$_2$(CH$_2$)$_5$CH$_2$O), 16.9 (C6"). ESI MS: m/z calcd [C$_{66}$H$_{79}$N$_3$O$_{15}$]$^+$: 1176.5403. Found 1176.5402.

Synthesis of 7-Octen-1yl 2-Azido-4,6-O-benzylidene-3-O-(4,6-O-benzylidene-3-O-pivaloyl-2-O-(2,3,4-tri-O-benzyl-α-L-fucopyranosyl)-β-D-galactopyranosyl)-2-deoxy-β-D-glucopyranoside (I-10)

A solution of the pivaloyl ester I-9 (1.456 g, 1.26 mmol) in CH$_3$OH (150 mL) was treated with catalytic LiOCH$_3$ (100 mg) and the solution refluxed (7 d). The solution was then concentrated, extracted with EtOAc (400 mL) and washed with saturated NaHCO$_3$ and brine. The organic extract was then dried, concentrated and subjected to flash chromatography (EtOAc/hexanes, 3:7) to afford the alcohol I-10 as a colourless oil (1.10 g, 82%). [α]−20.7 (c=0.1, CH$_2$Cl$_2$); R$_f$ 0.26 (EtOAc/hexanes, 3:7); $^1$H NMR (500 MHz): δ$_H$ 7.63-7.19 (25H, m, Ph), 5.89-5.79 (1H, m, CH$_2$=CH), 5.57 (1H, s, PhCH), 5.54 (1H, s, PhCH), 5.33 (1H, s, H1"), 5.06-4.94 (3H, m, PhCH$_2$, CH$_2$=CH), 4.85 (1H, A of AB, J 11.5, PhCH$_2$), 4.84-4.74 (3H, m, PhCH$_2$), 4.68 (1H, d, J$_{1',2'}$ 7.1, H1'), 4.66 (1H, A of AB, J 11.1, PhCH$_2$), 4.42 (1H, d, J$_{1,2}$ 8.2, H1), 4.35 (1H, dd, J$_{6,6}$ 10.5, J$_{5,6}$ 4.8, H6), 4.31 (1H, q, J$_{5'',6''}$ 6.3, H5"), 4.23 (1H, d, J$_{6',6'}$ 12.4, H6'), 4.18 (1H, d, J$_{3',4'}$ 3.2, H4'), 4.13-4.06 (2H, m, H2", H3"), 3.98-3.90 (3H, m, H2', H6, CH=CH$_2$(CH$_2$)$_5$CH$_2$O), 3.86-3.79 (3H, m, H4", H6', OH), 3.78-3.72 (2H, m, H3, H3'), 3.68 (1H, dd, J$_{3,4}$ 9.0, J$_{4,5}$ 9.0, H4), 3.63-3.58 (1H, m, CH=CH$_2$(CH$_2$)$_5$CH$_2$O), 3.44 (1H, dd, J$_{1,2}$ 8.2, J$_{2,3}$ 8.2, H2), 3.41-3.36 (1H, m, H5), 3.26 (1H, s, H5'), 2.12-2.04 (2H, m, CH=CH$_2$(CH$_2$)$_5$CH$_2$O), 1.78-1.56 (2H, m, CH=CH$_2$(CH$_2$)$_5$CH$_2$O), 1.49-1.32 (6H, m, CH=CH₂(CH₂)₅CH₂O), 1.24 (d, 3H, J₅",₆" 6.3, H6"). ¹³C NMR (125 MHz): δ_C 139.0 (CH₂=CH), 138.8 (Ph), 138.7 (Ph), 137.9 (Ph), 137.8 (Ph), 137.1 (Ph), 129.0 (Ph), 128.7 (Ph), 128.41 (Ph), 128.38 (Ph), 128.36 (Ph), 128.23 (2C, Ph), 128.19 (Ph), 128.1 (Ph), 127.8 (Ph), 127.54 (Ph), 127.46 (Ph), 127.4 (Ph), 126.9 (Ph), 126.1 (Ph), 114.3 (CH₂=CH), 102.9 (C1), 101.7, 101.2, 100.9 (3C, PhCH, C1'), 99.41 (C1"), 79.9, 78.8, 78.0, 77.8, 77.1, 76.5, 75.5 (C2', C2", C3, C3', C3", C4, C4'), 75.0 (PhCH₂), 74.0 (PhCH₂), 73.8 (C4"), 72.7 (PhCH₂), 70.7 (CH=CH₂(CH₂)₅CH₂O), 69.0, 68.5 (C6, C6'), 66.8, 66.74, 66.70, 66.6 (C2, C5, C5', C5"), 33.7 (CH=CH₂(CH₂)₅CH₂O), 29.5 (CH=CH₂(CH₂)₅CH₂O), 28.83 (CH=CH₂(CH₂)₅CH₂O), 28.80 (CH=CH₂(CH₂)₅CH₂O), 25.8 (CH=CH₂(CH₂)₅CH₂O), 17.04 (C6"). ESI MS: m/z calcd [C₆₁H₇₁N₃O₁₄]Na⁺: 1092.4828. Found 1092.4823.

Synthesis of 7-Octen-1yl 2-Azido-4,6-O-benzylidene-3-O-(3-O-(2-Azido-2-deoxy-3,4,6-tetra-O-acetyl-α-D-galactopyranosyl)-4,6-O-benzylidene-2-O-(2,3,4-tri-O-benzyl-α-L-fucopyranosyl)-β-D-galactopyranosyl)-2-deoxy-β-D-glucopyranoside (I-12)

A solution of the acceptor I-10 (621 mg, 0.58 mmol) and the trichloroacetimidate (Gerhard, G., Schmidt, R. R. *Liebigs Ann.*, 1984, 1826-1847) (I-11) (823 mg, 1.74 mmol) in dry Et₂O (15 mL) was treated with 4 Å molecular sieves (rt, 1 h). The mixture was cooled (−20° C.) and treated with TMSOTf (10 μL, 0.058 mmol) and allowed to warm (0° C.). The mixture was treated with Et₃N (200 μL), filtered, concentrated and subjected to flash chromatography (EtOAc/CH₂Cl₂, 3:97) to afford the tetrasaccharide I-12 as a colourless oil (737 mg, 92%). [α]+8.87 (c=0.1, CH₂Cl₂); R_f 0.25 (EtOAc/hexanes, 2:3); ¹H NMR (500 MHz): δ_H 7.55-7.20 (25H, m, Ph), 5.87-5.77 (1H, m, CH₂=CH), 5.53 (1H, d, 2.5, H1"), 5.51 (1H, s, PhCH), 5.49 (1H, s, PhCH), 5.28 (1H, d, J₁‴,₂‴ 3.2, H1‴), 5.20 (1H, dd, J₂‴,₃‴ 11.0, J₃‴,₄‴ 2.9, H3‴), 5.18-5.12 (2H, m, PhCH₂, H4‴), 5.04-4.93 (3H, m, PhCH₂, CH₂=CH), 4.90 (1H, A of AB, J 11.9, PhCH₂), 4.75 (2H, s, PhCH₂), 4.67 (1H, d, J₁',₂' 7.9, H1'), 4.63 (1H, A of AB, J 11.9, PhCH₂), 4.52 (1H, q, J₅",₆" 6.3, H5"), 4.46 (1H, d, J₁,₂ 8.0, H1), 4.33 (1H, dd, J₆,₆ 10.5, J₅,₆ 4.7, H6), 4.28-4.25 (1H, m, H4'), 4.22-4.12 (5H, m, H2', H2", H3", H5‴, H6'), 3.88 (1H, d, J₆',₆' 12.4, H6'), 3.84-3.74 (5H, m, H3', H4, H4", H6, H6‴), 3.70 (1H, dd, J₂,₃ 9.2, J₃,₄ 9.2, H3), 3.99-3.92 (1H, m, CH=CH₂(CH₂)₅CH₂O), 3.65-3.60 (1H, m, CH=CH₂(CH₂)₅CH₂O), 3.55 (1H, dd, J₂‴,₃‴ 11.0, J₁‴,₂‴ 3.2, H2"), 3.50-3.37 (2H, m, H2, H5), 3.22 (1H, dd, J₆‴,₆‴ 11.5, J₅‴,₆‴ 3.5, H6‴), 3.10-3.07 (1H, m, H5"), 2.09 (3H, s, CH₃C=O), 2.09 (3H, s, CH₃C=O), 1.94 (3H, s, CH₃C=O), 2.10-2.06 (2H, m, CH=CH₂(CH₂)₅CH₂O), 1.77-1.55 (2H, m, CH=CH₂(CH₂O), 1.47-1.35 (6H, m, CH=CH₂(CH₂)₅CH₂O), 1.22 (3H, d, J₅",₆" 6.3, H6") 125 MHz): δ_C 170.3 (C=O), 169.7 (C=O), 169.4 (C=O), 139.4 (Ph), 139.0 (Ph), 138.81 (Ph), 138.79 (CH₂=CH), 137.6 (Ph), 137.0 (Ph), 129.0 (Ph), 128.7 (Ph), 128.3 (Ph), 128.24 (Ph), 128.16 (Ph), 128.1 (Ph), 128.0 (Ph), 127.45 (Ph), 127.42 (Ph), 127.37 (Ph), 127.3 (Ph), 127.2 (Ph), 126.2 (Ph), 126.1 (Ph), 114.3 (CH₂=CH), 102.9 (C1), 101.4, 101.2, 100.7 (3C, C1', PhCH), 97.9 (C1"), 94.1 (C1‴), 80.7 (C2'), 79.7 (C3), 74.9 (PhCH₂), 74.0 (PhCH₂), 72.5 (PhCH₂), 77.9, 77.8, 77.3, 76.0, 72.0 (C2', C3', C3", C4, C4"), 72.0 (C4'), 70.8 (CH–CH₂(CH₂)₅CH₂O), 69.1, 68.6 (C6, C6'), 68.8, 68.0 (C3‴, C4‴), 67.6 (C5‴), 66.7, 66.4, 66.11, 66.09 (C2, C5, C5', C5"), 62.7 (C6‴), 57.9 (C2‴), 33.7 (CH=CH₂(CH₂)₅CH₂O), 29.5 (CH=CH₂(CH₂)₅CH₂O), 28.82 (CH=CH₂(CH₂)₅CH₂O), 28.80 (CH=CH₂(CH₂)₅CH₂O), 25.8 (CH=CH₂(CH₂)₅CH₂O), 20.7 (CH₃C=O), 20.62 (CH₃C=O), 20.58 (CH₃C=O), 16.9 (C6"). ESI MS: m/z calcd [C₇₁H₈₄N₅O₁₉]Na⁺: 1405.5738. Found 1405.5740.

Synthesis of 7-Octen-1yl 2-N-Acetyl-3-O-(3-O-(2-N-acetyl-2-deoxy-α-D-galactopyranosyl)-2-O-(α-L-fucopyranosyl)-β-D-galactopyranosyl)-2-deoxy-β-D-glucopyranoside (I-13)

A solution of the tetrasaccharide I-12 (355 mg, 0.257 mmol) in pyridine (2 mL) was treated with AcSH (4 mL) and the solution stirred (14 d). The mixture was filtered, concentrated and subjected to flash chromatography (EtOAc/CH₂Cl₂, 1:1) to afford the intermediate as a colourless oil (270 mg, 74%). A solution of the intermediate (225 mg, 0.160 mmol) in CH₃OH was treated with a catalytic amount of NaOCH₃ in CH₃OH and the solution stirred (2 h). The solution was neutralized with Amberlite IR 120 (H⁺), filtered and the residue subjected to flash chromatography (EtOAc/CH₂Cl₂, 1:1) to afford the triol as a colourless oil (192 mg, 94%). Redistilled liquid ammonia (20 mL) was collected in a flask cooled to −78° C. and treated with sodium until the blue colour persisted. A solution of the tetrasaccharide triol (58 mg, 0.045 mmol) in THF (4 mL) and CH₃OH (9.1 μL, 0.225 mmol) was added drop-wise and the solution stirred (−78° C., 1 h). The solution was then quenched with CH₃OH (4 mL) and the ammonia evaporated to dryness. The solution was taken up in CH₃OH (100 mL), neutralized with Amberlite IR 120 (H⁺), filtered and the residue subjected to C-18 chromatography (CH₃OH/H₂O, 1:1) to afford the fully deprotected tetrasaccharide I-13 (33.5 mg, 88%) as a colourless oil. [α]+27.15 (c=0.2, H₂O); ¹H NMR (500 MHz, D₂O): δ_H 5.95-5.86 (1H, m, CH₂=CH), 5.23 (1H, d, J₁",₂" 4.5, H1"), 5.16 (1H, d, J₁‴,₂‴ 3.8, H1‴), 5.08-50.1, 4.98-4.94 (2H, 2×m, CH₂=CH), 4.68 (1H, d, J₁,₂ 7.1, H1), 4.38 (1H, d, J₁',₂' 8.6, H1"), 4.34 (1H, q, J₅",₆" 6.6, H5"), 4.31-4.17, 4.01-3.59, 3.56-3.43 (23H, 3×m, H2, H2', H2", H2‴, H3, H3', H3", H4‴, H5, H5', H5‴, H6, H6', H6‴, CH=CH₂(CH₂)₅CH₂O), 2.03 (3H, s, C=O), 2.02 (3H, s, CH₃C=O), 2.08-2.00 (2H, m, CH=CH₂(CH₂)₅CH₂O), 1.56-1.44 (2H, m, CH=CH₂(CH₂)₅CH₂O), 1.41-1.26 (6H, m, CH=CH₂(CH₂)₅CH₂O), 1.22 (1H, d, J₅",₆" 6.6, H6"). ¹³C NMR (125 MHz): δ_C 175.7 (C=O), 174.5 (C=O), 141.2 (CH₂=CH), 114.9 (CH₂=CH), 102.8, 100.8, 100.0 (C1, C1', C1"), 92.1 (C1‴), 78.3, 76.33, 76.27, 75.7, 74.7, 72.7, 71.8, 70.6, 69.7, 69.4, 68.53, 68.50, 67.5, 63.8 (C2', C2‴, C3, C3', C3", C3‴, C4, C4', C4", C4‴, C5, C5', C5", C5‴), 71.5 (CH=CH₂(CH₂)₅CH₂O), 62.3, 62.1, 61.6 (C6, C6', C6‴), 55.6 (C2), 50.5 (C2"), 34.0 (CH=CH₂(CH₂)₅CH₂O), 29.4 (CH=CH₂(CH₂)₅CH₂O), 29.0 (CH=CH₂(CH₂)₅CH₂O), 28.8 (CH=CH₂(CH₂)₅CH₂O), 25.8 (CH=CH₂(CH₂)₅CH₂O), 23.2 (CH₃C=O₃C=O), 16.1 (C6"). ESI MS: m/z calcd [C₃₆H₆₂N₂O₂₀]Na⁺: 865.3788. Found 865.3788.

Synthesis of 8-(3-(trimethoxysilyl)propylthio)octan-1-yl 2-N-Acetyl-3-O-(3-O-(2-N-acetyl-2-deoxy-α-D-galactopyranosyl)-2-O-(α-L-fucopyranosyl)-β-D-galactopyranosyl)-2-deoxy-β-D-glucopyranoside (I-14)

A degassed solution of the alkene (I-13) (10 mg, 0.012 mmol) in dry MeOH (0.4 mL) was treated with MPTMS (7 mg, 0.0.36 mmol), DAROCUR 1173 (2 μL) and the solution irradiated at 254 nm and 1200 W (16×75 W lamps) for 30 min. The solution was then diluted with dry MeOH (2 mL) and washed with hexanes (3×2 mL). The solution was then concentrated to afford I-14 (9.5 mg, 80%) as a somewhat unstable colourless oil.

Example 2
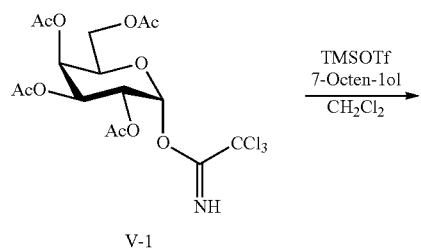
V-1
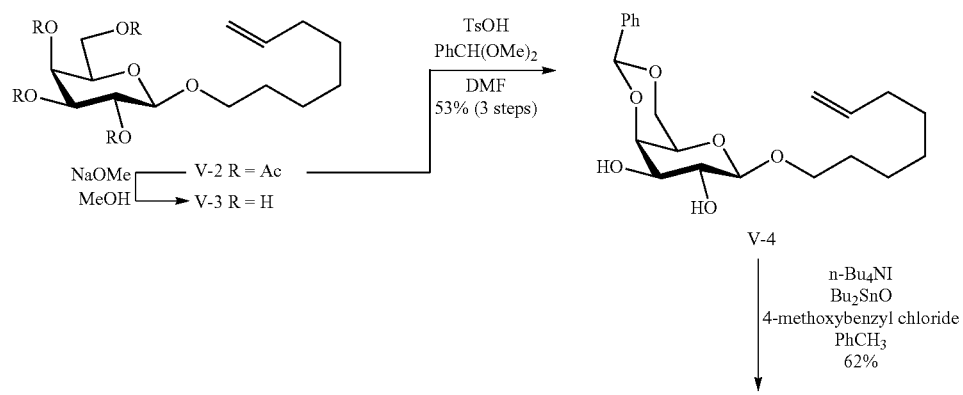
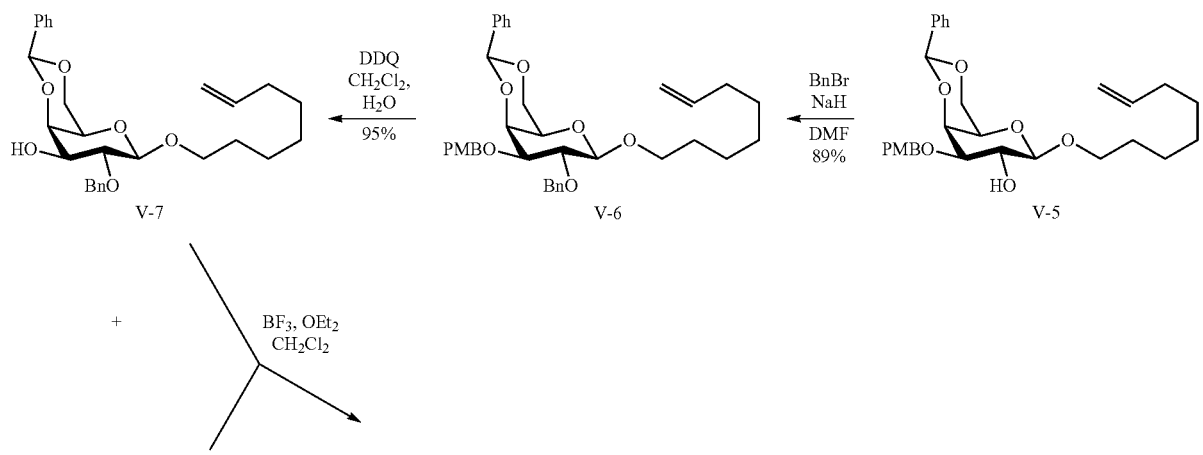
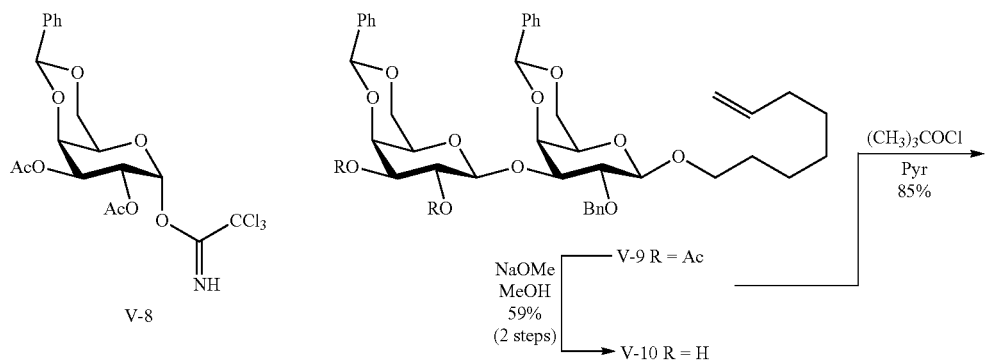

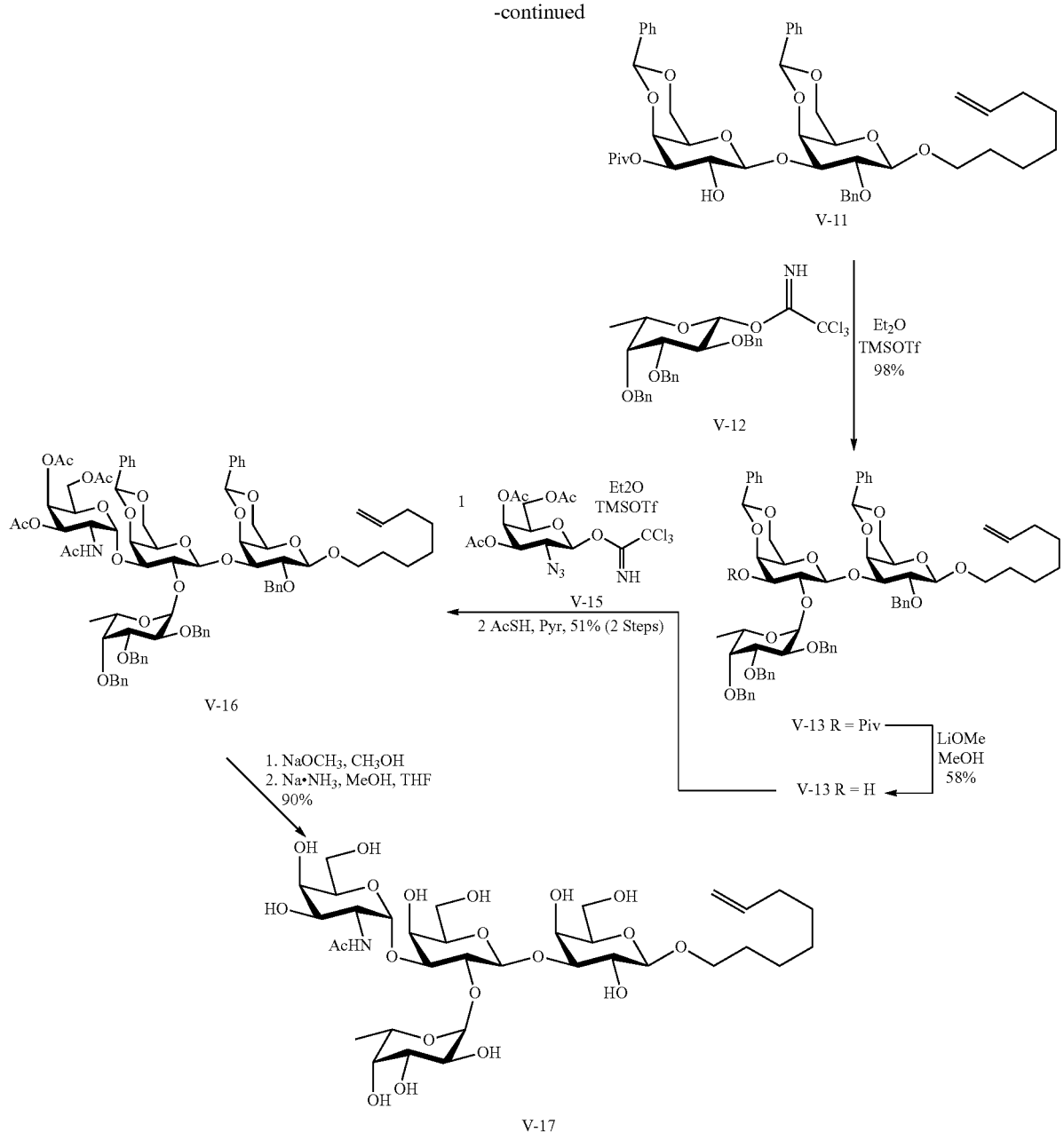

Synthesis of 7-Octen-1-yl 4,6-O-Benzylidene-β-D-galactopyranoside (V-4)

A stirred solution of 2,3,4,6-tetra-O-acetyl-α-D-galactopyranosyl trichloroacetimidate (Amvamzollo, P. H., Sinay, P. *Carbohydr. Res.*, 1986, 150:199-212) (V-1) (20.9 g, 42.5 mmol) and 7-octen-1-ol (6.53 g, 51.0 mmol) in dry CH$_2$Cl$_2$ (400 mL) was treated with 4 Å molecular sieves (5 g) and the mixture stirred (rt, 1 h). The mixture was then cooled (−40° C.), treated with TMSOTf (0.5 mL) and the mixture was allowed to warm (rt, 1 h). The reaction was quenched by the addition of Et$_3$N (2 mL), filtered and subjected to flash chromatography (EtOAc/hexanes, 2:3) to afford a colourless oil. The oil was taken up in CH$_3$OH (200 mL), treated with a catalytic amount of NaOCH$_3$ in CH$_3$OH and stirred (rt, 2 h); the NaOCH$_3$ was neutralized with Amberlite IR120 (H$^+$), filtered and then concentrated. The residue was subjected to flash chromatography (EtOAc/hexanes, 5:1) to afford the tetrol V-3 as a white solid (9.0 g, 73%), which was immediately used in the subsequent step. A solution of the tetrol V-3 (9.0 g, 31.0 mmol) in dry DMF (100 mL) was treated with benzaldehyde dimethyl acetal (5.9 mL, 38.7 mmol), p-TsOH (300 mg) and the solution was stirred (40° C., 18 h). The solution was neutralized with Et$_3$N (1.5 mL), concentrated and subjected to flash chromatography (EtOAc/hexanes, 1:1) to afford the diol V-4 (8.4 g, 72%) as a white solid. Mp 156-158° C.; [α]−26.0 (c=0.7, CH$_2$Cl$_2$). Found: C, 66.54; H, 8.05%. C$_{21}$H$_{30}$O$_6$ requires C, 66.65; H, 7.99%); R$_f$ 0.37 (EtOAc/hexanes, 7:10). $^1$H NMR (500 MHz): δ$_H$ 7.54-7.48 (2H, m, Ph), 7.40-7.34 (3H, m, Ph), 5.86-5.77 (1H, m, CH═CH$_2$), 5.56 (1H, s, PhCH), 5.03-4.92 (2H, m, CH═CH$_2$), 4.35 (1H, dd, J$_{6,6}$ 12.5, J$_{5,6}$ 1.4, H6), 4.28 (1H, d, $J_{1,2}$ 7.5, H1), 4.22 (1H, d, $J_{3,4}$ 3.8, H4), 4.10 (1H, dd, $J_{6,6}$ 12.5, $J_{5,6}$ 1.9, H6), 3.97 (1H, ddd, J 9.4, 6.8, 6.8, CH=CH$_2$ (CH$_2$)$_5$CH$_2$O), 3.76 (1H, ddd, $J_{2,3}$ 9.4, $J_{1,2}$ 7.5, J 1.7, H2), 3.70 (1H, ddd, $J_{2,3}$ 9.4, J 8.9, $J_{3,4}$ 3.8, H3), 3.54-3.48 (2H, m, H5, CH=CH$_2$(CH$_2$)$_5$CH$_2$O), 2.51 (1H, d, J 8.9, OH), 2.45 (1H, d, J 1.7, OH), 2.10-2.02 (2H, m, CH=CH$_2$(CH$_2$)$_5$CH$_2$O), 1.72-1.63 (2H, m, CH=CH$_2$(CH$_2$)$_5$CH$_2$O), 1.46-1.30 (6H, m, CH=CH$_2$(CH$_2$)$_5$CH$_2$O); $^{13}$C NMR (125.7 MHz): $\delta_C$ 139.3 (CH=CH$_2$), 137.6 (Ph), 129.2 (Ph), 128.2 (Ph), 126.4 (Ph), 114.3 (CH=CH$_2$), 102.8 (C1), 101.4 (PhCH), 75.4 (C4), 72.7, 71.7 (C2, C3), 70.0, 69.2 (C6, CH=CH$_2$(CH$_2$)$_5$CH$_2$O), 66.66 (C5), 33.7 (CH=CH$_2$(CH$_2$)$_5$CH$_2$O), 29.5 (CH=CH$_2$(CH$_2$)$_5$CH$_2$O), 28.9 (CH=CH$_2$(CH$_2$)$_5$CH$_2$O), 28.8 (CH=CH$_2$(CH$_2$)$_5$CH$_2$O), 25.8 (CH=CH$_2$(CH$_2$)$_5$CH$_2$O), ESI MS: m/z calcd [C$_{21}$H$_{30}$O$_6$]Na$^+$: 401.1935. Found: 401.1937.

Synthesis of 7-Octen-1-yl 4,6-O-Benzylidene-3-O-[(4-methoxyphenyl)methyl]-β-D-galactopyranoside (V-5)

A stirred mixture of the diol V-4 (5.83 g, 15.4 mmol) and n-Bu$_2$SnO (4.21 g, 17.0 mmol) in dry toluene (200 mL) was heated at reflux with azeotropic removal of water (1 h). The solution was treated with n-Bu$_4$NI (7.95 g, 21.6 mmol), p-methoxybenzyl chloride (2.9 mL, 21.6 mmol) and then heated at reflux further (4 h). The solution was partially concentrated, taken up in EtOAc (300 mL), washed with water, brine and dried. The organic extract was then concentrated and subjected to flash chromatography (EtOAc/hexanes, 2:3) to afford the 3-O-p-methoxybenzyl derivative V-5 as a white solid (4.7 g, 62%). Mp 139-141° C.; [α]+34.8 (c=0.6, CH$_2$Cl$_2$); R$_f$ 0.56 (EtOAc/hexanes, 1:1); (Found: C, 70.03; H, 7.79%. C$_{29}$H$_{38}$O$_7$ requires C, 69.86; H, 7.68%). $^1$H NMR (500 MHz): $\delta_H$ 7.55-7.51 (2H, m, Ph), 7.38-7.30 (5H, m, Ph), 6.89-6.85 (2H, m, Ph), 5.86-5.76 (1H, m, CH=CH$_2$), 5.47 (1H, s, PhCH), 5.03-4.91 (2H, m, CH=CH$_2$), 4.71-4.69 (2H, AB, J 12.0, PhCH$_2$), 4.33-4.27 (2H, m, H1, H6), 4.11 (1H, d, $J_{3,4}$ 3.5, H4), 4.06-3.91 (3H, m, H2, H6, CH=CH$_2$(CH$_2$)$_5$CH$_2$O), 3.80 (3H, s, CH$_3$O), 3.54-3.45 (2H, m, H3, CH=CH$_2$(CH$_2$)$_5$CH$_2$O), 3.36-3.33 (1H, m, H5), 2.45 (1H, d, J 1.65, OH), 2.08-2.01 (2H, m, CH=CH$_2$(CH$_2$)$_5$CH$_2$O), 1.70-1.61 (2H, m, CH=CH$_2$(CH$_2$)$_5$CH$_2$O), 1.44-1.30 (6H, m, CH=CH$_2$(CH$_2$)$_5$CH$_2$O); $^{13}$C NMR (125.7 MHz): $\delta_C$ 159.3 (Ph), 139.0 (CH=CH$_2$), 137.8 (Ph), 130.2 (Ph), 129.5 (Ph), 128.8 (Ph), 128.0 (Ph), 126.4 (Ph), 114.2 (CH=CH$_2$), 113.8 (Ph), 102.9 (C1), 101.1 (PhCH), 78.8 (C3), 73.2 (C4), 71.1 (PhCH$_2$), 70.0 (C2), 69.7, 69.3 (C6, CH=CH$_2$(CH$_2$)$_5$CH$_2$O), 66.7 (C5), 55.2 (CH$_3$O), 33.7 (CH=CH$_2$(CH$_2$)$_5$CH$_2$O), 29.4 (CH=CH$_2$(CH$_2$)$_5$CH$_2$O), 28.9 (CH=CH$_2$(CH$_2$)$_5$CH$_2$O), 28.8 (CH=CH$_2$(CH$_2$)$_5$CH$_2$O), 25.7 (CH=CH$_2$(CH$_2$)$_5$CH$_2$O). ESI MS: m/z calcd [C$_{29}$H$_{38}$O$_7$]Na$^+$: 521.2518. Found 521.2510.

Synthesis of 7-Octen-1-yl 2-O-Benzyl-4,6-O-benzylidene-3-O-[(4-methoxyphenyl)methyl]-β-D-galactopyranoside (V-6)

A stirred solution of the alcohol V-5 (5.5 g, 11.0 mmol) in dry DMF (75 mL) was cooled (−20° C.), treated with BnBr (2.10 mL, 17.6 mmol) and NaH (60%, 572 mg, 14.3 mmol) and allowed to warm (rt, 1 h). The mixture was then treated with CH$_3$OH (1 mL) and partially concentrated; the residue was taken up in EtOAc (250 mL) and washed with water and brine. The organic extract was dried, concentrated and then subjected to flash chromatography (EtOAc/hexanes, 2:3) to afford the benzyl ether V-6 as a white solid (5.83 g, 89%). Mp 99-103° C.; [α]+42.7 (c=0.5, CH$_2$Cl$_2$); R$_f$ 0.74 (EtOAc/hexanes, 1:1); (Found: C, 73.47; H, 7.54%. C$_{29}$H$_{38}$O$_7$ requires C, 73.44; H, 7.53%); $^1$H NMR (500 MHz): $\delta_H$ 7.60-7.54 (2H, m, Ph), 7.41-7.26 (10H, m, Ph), 6.88-6.82 (2H, m, Ph), 5.86-5.76 (1H, m, CH=CH$_2$), 5.50 (1H, s, PhCH), 5.02-4.92 (3H, m, PhCH$_2$, CH=CH$_2$), 4.78 (1H, A of AB, J 10.8, PhCH$_2$), 4.73, 4.69 (2H, AB, J 11.9, PhCH$_2$), 4.38 (1H, d, $J_{1,2}$ 7.8, H1), 4.31 (1H, dd, $J_{6,6}$ 12.2, $J_{5,6}$ 1.3 H6), 4.08 (1H, d, $J_{3,4}$ 3.7, H4), 4.05-3.96 (2H, m, H6, CH=CH$_2$(CH$_2$)$_5$CH$_2$O), 3.85-3.80 (4H, m, H2, CH$_3$O), 3.54 (1H, dd, $J_{2,3}$ 9.7, $J_{3,4}$ 3.7, H3), 3.53-3.48 (1H, m, CH=CH$_2$(CH$_2$)$_5$CH$_2$O), 3.31 (1H, s, H5), 2.09-1.98 (2H, m, CH=CH$_2$(CH$_2$)$_5$CH$_2$O), 1.73-1.60 (2H, m, CH=CH$_2$(CH$_2$)$_5$CH$_2$O), 1.49-1.27 (6H, m, CH=CH$_2$(CH$_2$)$_5$CH$_2$O); $^{13}$C NMR (125.7 MHz): $\delta_C$ 159.2 (Ph), 139.1 (CH=CH$_2$), 139.0 (Ph), 137.9 (Ph), 130.5 (Ph), 129.3 (Ph), 128.9 (Ph), 128.2 (Ph), 128.1 (Ph), 128.0 (Ph), 127.5 (Ph), 126.5 (Ph), 114.2 (CH=CH$_2$), 113.7 (Ph), 103.7 (C1), 101.3 (PhCH), 78.8, 78.5 (C2, C3), 74.1 (C4), 75.2 (PhCH$_2$), 71.7 (PhCH$_2$), 69.9, 69.3 (C6, CH=CH$_2$(CH$_2$)$_5$CH$_2$O), 66.42 (C5), 55.27 (CH$_3$O), 33.7 (CH=CH$_2$(CH$_2$)$_5$CH$_2$O), 29.7 (CH=CH$_2$(CH$_2$)$_5$CH$_2$O), 29.0 (CH=CH$_2$(CH$_2$)$_5$CH$_2$O), 28.8 (CH=CH$_2$(CH$_2$)$_5$CH$_2$O), 26.0 (CH=CH$_2$(CH$_2$)$_5$CH$_2$O). ESI MS: m/z calcd [C$_{36}$H$_{44}$O$_7$]Na$^+$: 611.2979. Found: 611.2977.

Synthesis of 7-Octen-1-yl 2-O-Benzyl-4,6-O-benzylidene-β-D-galactopyranoside (V-7)

A stirred solution of V-6 (5.60 g, 9.52 mmol) in CH$_2$Cl$_2$/H$_2$O (19:1, 100 mL) was treated with 2,3-dichloro-5,6-dicyano-p-benzoquinone (2.59 g, 11.4 mmol) and the solution was stirred (2 h). The mixture was then diluted with CH$_2$Cl$_2$ (300 mL) and washed twice with saturated NaHCO$_3$ (300 mL). The solution was dried, concentrated and subjected to flash chromatography (EtOAc/hexanes, 1:1) to afford the alcohol V-7 as a white non-crystalline solid (4.22 g, 95%). [α]+9.0 (c=0.6, CH$_2$Cl$_2$); R$_f$ 0.48 (EtOAc/hexanes, 1:1); $^1$H NMR (500 MHz): $\delta_H$ 7.55-7.50 (2H, m, Ph), 7.42-7.26 (8H, m, Ph), 5.86-5.76 (1H, m, CH=CH$_2$), 5.56 (1H, s, PhCH), 5.03-4.92 (3H, m, PhCH$_2$, CH=CH$_2$), 4.73 (1H, A of AB, J 11.3, PhCH$_2$), 4.40 (1H, d, $J_{1,2}$ 7.7, H1), 4.34 (1H, dd, $J_{6,6}$ 12.4, $J_{5,6}$ 1.5, H6), 4.41 (1H, dd, $J_{6,6}$ 12.4, $J_{5,6}$ 1.9, H6), 4.22 (1H, dd, $J_{3,4}$ 3.8, $J_{4,5}$ 0.9, H4), 4.01 (1H, ddd, J 9.4, 6.5, 6.5, CH=CH$_2$(CH$_2$)$_5$CH$_2$O), 3.74 (1H, ddd, $J_{2,3}$ 9.6, J 7.3, $J_{3,4}$ 3.8, H3), 3.63 (1H, dd, $J_{2,3}$ 9.6, $J_{1,2}$ 7.7, H2), 3.52 (1H, ddd, J 9.4, 6.9, 6.9, CH=CH$_2$(CH$_2$)$_5$CH$_2$O), 3.43-3.44 (1H, m, H5), 2.53 (1H, d, J 7.3, OH), 2.08-2.01 (2H, m, CH=CH$_2$(CH$_2$)$_5$CH$_2$O), 1.61-1.73 (2H, m, CH=CH$_2$(CH$_2$)$_5$CH$_2$O), 1.49-1.30 (6H, m, CH=CH$_2$(CH$_2$)$_5$CH$_2$O). $^{13}$C NMR (125.7 MHz): $\delta_C$ 139.0 (CH=CH$_2$), 138.6 (Ph), 137.6 (Ph), 129.1 (Ph), 128.3 (Ph), 128.2 (Ph), 127.9 (Ph), 127.6 (Ph), 126.5 (Ph), 114.2 (CH=CH$_2$), 103.6 (C1), 101.4 (PhCH), 79.3 (C2), 75.6 (C4), 74.8 (PhCH$_2$), 72.5 (C3), 70.0, 69.2 (C6, CH=CH$_2$(CH$_2$)$_5$CH$_2$O), 66.5 (C5), 33.7 (CH=CH$_2$(CH$_2$)$_5$CH$_2$O), 29.7 (CH=CH$_2$(CH$_2$)$_5$CH$_2$O), 28.9 (CH=CH$_2$(CH$_2$)$_5$CH$_2$O), 28.8 (CH=CH$_2$(CH$_2$)$_5$CH$_2$O), 26.0 (CH=CH$_2$(CH$_2$)$_5$CH$_2$O). ESI MS: m/z calcd [C$_{28}$H$_{36}$O$_6$]Na$^+$: 491.2404. Found: 491.2402.

Synthesis of 7-Octen-1-yl 2-O-Benzyl-3-O-(4,6-O-benzylidene-β-D-galactopyranosyl)-4,6-O-benzylidene-β-D-galactopyranoside (V-10)

A solution of the acceptor V-7 (3.59 g, 7.67 mmol) in dry CH$_2$Cl$_2$ (50 mL) was stirred over 4 Å molecular sieves (3 g) (rt, 1 h). The solution was then cooled (−40° C.), treated with BF$_3$.OEt$_2$ (0.5 mL) followed by drop-wise addition of the trichloroacetimidate (Figueroa-Pérez, S., Vérez-Bencomo, V. *Carbohydr. Res.*, 1999, 317:29-38) (V-8) (7.57 g, 15.34 mmol) and then the mixture allowed to warm (0° C.). The mixture was neutralized with Et$_3$N (2 mL), concentrated and subjected to flash chromatography (EtOAc/hexanes, 1:1) to afford a colourless oil, which was immediately used in the next step. The colourless oil was taken up in CH$_3$OH (100 mL), treated with a solution of NaOCH$_3$ in CH$_3$OH and stirred (rt, 3 h). The solution was neutralized with Amberlite IR 120 (H$^+$), filtered and subjected to flash chromatography (EtOAc/hexanes, 7:3) to afford the diol V-10 as a colourless oil (3.24 g, 59%). [α]+14.0 (c=0.4, CH$_2$Cl$_2$); R$_f$ 0.44 (EtOAc/hexanes, 7:3); $^1$H NMR (500 MHz): δ$_H$ 7.60-7.23 (15H, m, Ph), 5.87-5.76 (1H, m, CH$_2$=CH), 5.56 (1H, s, PhCH), 5.51 (1H, s, PhCH), 5.04-4.92 (3H, m, PhCH$_2$, CH$_2$=CH), 4.70 (1H, A of AB, J 10.4, PhCH$_2$), 4.69 (1H, d, J$_{1',2'}$ 8.3, H1'), 4.41 (1H, d, J$_{1,2}$ 7.1, H1), 4.35 (1H, d, J$_{3,4}$ 2.8, H4), 4.31 (1H, dd, J$_{6,6}$ 12.3, J$_{5,6}$ 1.2, H6), 4.26 (1H, dd, J$_{6',6'}$ 12.4, J$_{5',6'}$ 1.1, H6'), 4.11 (1H, d, J$_{3',4'}$ 3.7, H4'), 4.08-4.00 (3H, m, H6, H6', CH=CH$_2$(CH$_2$)$_5$CH$_2$O), 3.92-3.85 (2H, m, H2, H3), 3.78 (1H, dd, 8.5, J$_{1',2'}$ 8.3, H2'), 3.63-3.57 (1H, m, H3'), 3.54 (1H, ddd, J 9.4, 6.9, 6.9, CH=CH$_2$(CH$_2$)$_5$CH$_2$O), 3.39 (1H, s, H5'), 3.31 (1H, s, H5'), 2.87 (1H, s, OH), 2.59 (1H, d, J 8.3, OH), 2.08-2.01 (2H, m, CH=CH$_2$(CH$_2$)$_5$CH$_2$O), 1.77-1.61 (2H, m, CH=CH$_2$(CH$_2$)$_5$CH$_2$O), 1.50-1.30 (6H, m, CH=CH$_2$(CH$_2$)$_5$CH$_2$O); $^{13}$C NMR (125 MHz): δ$_C$ 139.2 (CH$_2$=CH), 138.3 (Ph), 138.0 (Ph), 137.6 (Ph), 129.2 (Ph), 128.9 (Ph), 128.7 (Ph), 128.4 (Ph), 128.3 (Ph), 128.1 (Ph), 127.9 (Ph), 126.7 (Ph), 126.3 (Ph), 114.3 (CH$_2$=CH), 103.9 (PhCH), 103.7 (PhCH), 101.3, 101.2 (C1, C1'), 78.4, 77.4 (C2, C3), 76.4 (C4), 75.1 (PhCH$_2$), 75.3, 72.5, 71.8 (C2', C3', C4'), 70.1 (CH=CH$_2$(CH$_2$)$_5$CH$_2$O), 69.2, 69.1 (C6, C6'), 66.6, 66.5 (C5, C5'), 33.7 (CH=CH$_2$(CH$_2$)$_5$CH$_2$O), 28.7 (CH=CH$_2$(CH$_2$)$_5$CH$_2$O), 29.0 (CH=CH$_2$(CH$_2$)$_5$CH$_2$O), 28.9 (CH=CH$_2$(CH$_2$)$_5$CH$_2$O), 26.1 (CH=CH$_2$(CH$_2$)$_5$CH$_2$O). ESI MS: m/z calcd [C$_{41}$H$_{50}$O$_{11}$]Na$^+$: 741.3245. Found: 741.3245.

Synthesis of 7-Octen-1-yl 2-O-Benzyl-3-O-(4,6-O-benzylidene-3-O-pivaloyl-β-D-galactopyranosyl)-4,6-O-benzylidene-β-D-galactopyranoside (V-11)

A solution of the diol V-10 (2.7 g, 3.76 mmol) in pyridine (50 mL) was treated with trimethylacetal chloride (0.69 mL, 5.64 mmol) and the solution was stirred. A further addition of trimethylacetal chloride (0.69 mL, 5.64 mmol) was required to ensure completion. The solution was concentrated and subjected to flash chromatography (EtOAc/hexanes, 1:1) to afford the alcohol V-11 as a white solid (2.55 g, 85%). [α]+ 62.7 (c=2.2, CH$_2$Cl$_2$); R$_f$ 0.59 (EtOAc/hexanes, 3:2); $^1$H NMR (500 MHz): δ$_H$ 7.57-7.28 (15H, m, Ph), 5.85-5.76 (1H, m, CH$_2$=CH), 5.56 (1H, s, PhCH), 5.50 (1H, s, PhCH), 5.03-4.92 (3H, m, CH$_2$=CH, PhCH$_2$), 4.82 (1H, d, J$_{1',2'}$ 7.8, H1'), 4.79 (1H, dd, J$_{2',3'}$ 10.2, J$_{3',4'}$ 3.8, H3'), 4.68 (1H, A of AB, J 10.0, PhCH$_2$), 4.40 (1H, d, J$_{1,2}$ 7.5, H1), 4.35-4.25 (4H, m, H4, H4', H6, H6'), 4.07-3.99 (4H, m, H2', H6, H6', CH=CH$_2$(CH$_2$)$_5$CH$_2$O), 3.92 (1H, dd, J$_{2,3}$ 9.9, J$_{3,4}$ 3.4, H3), 3.87 (1H, dd, J$_{2,3}$ 9.9, J$_{1,2}$ 7.5, H2), 3.52 (1H, ddd, J 9.2, 7.0, 7.0, CH=CH$_2$(CH$_2$)$_5$CH$_2$O), 3.40-3.37 (2H, m, H5, H5'), 2.69 (1H, s, OH), 2.08-2.01 (2H, m, CH=CH$_2$(CH$_2$)$_5$CH$_2$O), 1.74-1.62 (2H, m, CH=CH$_2$(CH$_2$)$_5$CH$_2$O), 1.48-1.31 (6H, m, CH=CH$_2$(CH$_2$)$_5$CH$_2$O), 1.24 (9H, s, (CH$_3$)$_3$C); $^{13}$C NMR (100 MHz): δ$_C$ 178.4 (C=O), 139.0 (CH$_2$=CH), 138.2 (Ph), 137.9 (Ph), 137.8 (Ph), 128.9 (Ph), 128.8 (Ph), 128.7 (Ph), 128.5 (Ph), 128.1 (Ph), 128.0 (Ph), 127.9 (Ph), 126.6 (Ph), 125.9 (Ph), 114.2 (CH$_2$=CH), 103.9 (PhCH), 103.6 (PhCH), 101.2 (C1'), 100.4 (C1), 78.5 (C3), 76.2 (C2), 75.1 (PhCH$_2$), 73.3, 73.2 (3C, C3', C4, C4'), 70.1 (CH=CH$_2$(CH$_2$)$_5$CH$_2$O), 69.09, 69.07 (C6, C6'), 68.9 (C2'), 66.5 (2C, C5, C5'), 39.0 ((CH$_3$)$_3$C), 33.7 (CH=CH$_2$(CH$_2$)$_5$CH$_2$O), 29.7 (CH=CH$_2$(CH$_2$)$_5$CH$_2$O), 29.0 (CH=CH$_2$(CH$_2$)$_5$CH$_2$O), 28.8 (CH=CH$_2$(CH$_2$)$_5$CH$_2$O), 27.1 ((CH$_3$)$_3$C), 26.1 (CH=CH$_2$(CH$_2$)$_5$CH$_2$O). ESI MS: m/z calcd [C$_{46}$H$_{58}$O$_{12}$]Na$^+$: 825.3820. Found: 825.3830.

Synthesis of 7-Octen-1-yl 2-O-Benzyl-3-O-[4,6-O-benzylidene-2-O-(2,3,4-tri-O-benzyl-α-L-fucopyranosyl)-3-O-pivaloyl-β-D-galactopyranosyl]-4,6-β-benzylidene-β-D-galactopyranoside (V-13)

A solution of the alcohol V-11 (1.74 g, 2.16 mmol) in dry Et$_2$O/CH$_2$Cl$_2$ (9:1, 50 mL) was treated with 4 Å molecular sieves (1 g) and the mixture stirred (rt, 1 h). The mixture was then cooled (-10° C.), treated with TMSOTf (100 μL) followed by drop-wise addition of the trichloroacetimidate (Schmidt, R. R., Toepfer, A. *J. Carb. Chem.*, 1993, 12:809-822) (V-12) (3.65 g, 6.50 mmol) in dry Et$_2$O (15 mL). The mixture was treated with Et$_3$N (0.5 mL), filtered and subjected to flash chromatography (EtOAc/hexanes, 1:3) to yield the trisaccharide V-13 as a colourless oil (2.60 g, 98%). [α]-62.7 (c=0.3, CH$_2$Cl$_2$); R$_f$ 0.17 (EtOAc/hexanes, 1:1); $^1$H NMR (500 MHz): δ$_H$ 7.53-7.44 (6H, m, Ph), 7.39-7.13 (24H, m, Ph), 5.87-5.76 (1H, m, CH$_2$=CH), 5.51 (1H, s, PhCH), 5.44 (1H, s, PhCH), 5.46 (1H, d, J$_{1'',2''}$ 3.5, H1''), 5.13 (1H, d, J$_{1',2'}$ 8.0, H1'), 5.03-4.92 (2H, m, CH$_2$=CH), 4.89 (1H, dd, J$_{2',3'}$ 9.8, J$_{3',4'}$ 3.8, H3'), 4.82 (1H, A of AB, J 9.6, PhCH$_2$), 4.79 (1H, A of AB, J 12.0, PhCH$_2$), 4.74 (1H, A of AB, J 11.7, PhCH$_2$), 4.63-4.54 (4H, m, PhCH$_2$), 4.43 (1H, d, J$_{1,2}$ 7.7, H1), 4.36-4.24 (7H, m, H2', H4, H4', H5'', H6, H6', PhCH$_2$), 4.12-3.94 (6H, m, H2'', H3, H3'', H6, H6', CH=CH$_2$(CH$_2$)$_5$CH$_2$O), 3.79 (1H, dd, J$_{2,3}$ 9.9, J$_{1,2}$ 7.7, H2), 3.57 (1H, ddd, J 9.4, 7.0, 7.0, CH=CH$_2$(CH$_2$)$_5$CH$_2$O), 3.38 (1H, s, H5), 3.23 (1H, s, H5'), 3.20 (1H, d, J 1.3, H4''), 2.11-2.02 (2H, m, CH=CH$_2$(CH$_2$)$_5$CH$_2$O), 1.80-1.69 (2H, m, CH=CH$_2$(CH$_2$)$_5$CH$_2$O), 1.54-1.34 (6H, m, CH=CH$_2$(CH$_2$)$_5$CH$_2$O), 1.13 (9H, s, (CH$_3$)$_3$C), 0.54 (3H, d, J$_{5'',6''}$ 6.4, H6''); $^{13}$C NMR (100 MHz): δ$_C$ 178.0 (C=O), 139.1 (Ph), 139.0 (CH$_2$=CH), 138.9 (Ph), 138.5 (Ph), 137.9 (Ph), 137.6 (Ph), 129.3 (Ph), 129.1 (Ph), 128.8 (Ph), 128.6 (Ph), 128.3 (Ph), 128.21 (Ph), 128.16 (Ph), 128.1 (2C, Ph), 128.0 (Ph), 127.9 (Ph), 127.4 (Ph), 127.34 (Ph), 127.30 (Ph), 127.2 (Ph), 127.14 (Ph), 127.08 (Ph), 127.0 (Ph), 125.9 (Ph), 114.3 (CH$_2$=CH), 103.8 (C1), 101.9, 101.3, 100.4 (3C, C1', PhCH), 96.4 (C1''), 79.9 (C2), 79.3 (C3), 78.6 (C4'), 76.7, 76.4, 76.1, 74.3, 73.1 (C2'', C3', C3'', C4, C4'), 75.3 (PhCH$_2$), 75.0 (PhCH$_2$), 73.0 (PhCH$_2$), 72.6 (PhCH$_2$), 70.2 (CH=CH$_2$(CH$_2$)$_5$CH$_2$O), 69.03, 68.97 (C6, C6'), 68.9 (C5''), 66.52, 66.5, 66.3 (C2', C5, C5'), 38.9 ((CH$_3$)$_3$C), 33.8 (CH=CH$_2$(CH$_2$)$_5$CH$_2$O), 29.8 (CH=CH$_2$(CH$_2$)$_5$CH$_2$O), 29.0 (CH=CH$_2$(CH$_2$)$_5$CH$_2$O), 28.9 (CH=CH$_2$(CH$_2$)$_5$CH$_2$O), 27.1 ((CH$_3$)$_3$C), 26.3 (CH=CH$_2$(CH$_2$)$_5$CH$_2$O), 15.89 (C6''). ESI MS: m/z calcd [C$_{73}$H$_{86}$O$_{16}$]Na$^+$: 1241.5808. Found: 1241.5808.

Synthesis of 7-Octen-1-yl 2-O-Benzyl-3-O-[4,6-O-benzylidene-2-O-(2,3,4-tri-O-benzyl-α-L-fucopyranosyl)-β-D-galactopyranosyl]-4,6-O-benzylidene-β-D-galactopyranoside (V-14)

A stirred solution of V-13 (3.21 g, 2.62 mmol) in CH$_3$OH (150 mL) was treated with catalytic LiOCH$_3$ (200 mg) and the solution was heated at reflux (5 d). The solution was allowed to cool, neutralized with Amberlite IR 120 (H$^+$), filtered and subjected to flash chromatography (EtOAc/hexanes, 1:3) to afford first unreacted V-13 (350 mg, 11%); further elution (EtOAc/hexanes, 1:2) afforded alcohol V-14 as a colourless oil (1.72 g, 58%). [α]–50.3 (c=0.4, CH$_2$Cl$_2$); R$_f$ 0.77 (EtOAc/hexanes, 1:1); $^1$H NMR (500 MHz): δ$_H$ 7.56-7.47 (6H, m, Ph), 7.40-7.18 (24H, m, Ph), 5.88-5.78 (1H, m, CH$_2$=CH), 5.58 (1H, d, J$_{1'',2''}$ 3.55, H1''), 5.55 (1H, s, PhCH), 5.53 (1H, s, PhCH), 5.05-4.94 (3H, m, H1', CH$_2$=CH), 4.82, 4.76 (2H, AB, J 11.5, PhCH$_2$), 4.90, 4.64 (2H, AB, J 9.6, PhCH$_2$), 4.61, 4.53 (2H, AB, J 12.0, PhCH$_2$), 4.85, 4.45 (2H, AB, J 11.6, PhCH$_2$), 4.42 (1H, d, J$_{1,2}$ 7.8, H1), 4.31 (1H, d, J$_{3,4}$ 3.4, H4), 4.34-4.18 (3H, m, H5'', H6, H6'), 4.11 (1H, d, J$_{3',3'}$ 3.8, H4'), 4.10-3.97 (6H, m, H2'', H3, H3'', H6, H6', CH=CH$_2$(CH$_2$)$_5$CH$_2$O), 3.93 (1H, dd, J$_{2',3'}$ 8.4, J$_{1',2'}$ 8.2, H2'), 3.83 (1H, dd, J$_{2,3}$ 9.7, J$_{1,2}$ 7.8, H$^2$), 3.78-3.73 (1H, m, H3'), 3.55 (1H, ddd, J 9.1, 6.9, 6.9, CH=CH$_2$(CH$_2$)$_5$CH$_2$O), 3.39 (1H, s, H$^5$), 3.33 (1H, d, J 1.8, H4''), 3.29 (1H, d, J 7.5, OH), 3.24 (1H, s, H5'), 2.13-2.03 (2H, m, CH=CH$_2$(CH$_2$)$_5$CH$_2$O), 1.80-1.67 (2H, m, CH=CH$_2$(CH$_2$)$_5$CH$_2$O), 1.55-1.32 (6H, m, CH=CH$_2$(CH$_2$)$_5$CH$_2$O), 0.70 (3H, d, J$_{5'',6''}$ 6.4, H6''); $^{13}$C NMR (100 MHz): δ$_C$ 139.03 (CH$_2$=CH), 138.9 (Ph), 138.5 (Ph), 138.3 (Ph), 137.6 (Ph), 129.1 (Ph), 129.0 (Ph), 128.8 (Ph), 128.4 (Ph), 128.32 (Ph), 128.25 (Ph), 128.22 (Ph), 128.17 (Ph), 128.12 (2C, Ph), 128.09 (Ph), 128.0 (2C, Ph), 127.8 (Ph), 127.41 (Ph), 127.40 (Ph), 127.34 (Ph), 127.29 (Ph), 126.9 (Ph), 126.4 (Ph), 114.3 (CH$_2$=CH), 103.9 (C1), 101.5, 101.4, 101.2 (3C, C1', PhCH), 97.8 (C1''), 79.8, 79.5 (C2, C3), 78.3 (C4''), 76.7, 76.2, 75.9, 75.2, 74.8, 74.4 (C2', C2'', C3', C3'', C4, C4'), 75.0 (PhCH$_2$), 74.8 (PhCH$_2$), 73.0 (PhCH$_2$), 72.8 (PhCH$_2$), 70.1 (CH=CH$_2$(CH$_2$)$_5$CH$_2$O), 69.1, 69.0 (C6, C6'), 66.8, 66.64, 66.61 (C5, C5', C5''), 33.8 (CH=CH$_2$(CH$_2$)$_5$CH$_2$O), 29.8 (CH=CH$_2$(CH$_2$)$_5$CH$_2$O), 29.0 (CH=CH$_2$(CH$_2$)$_5$CH$_2$O), 28.9 (CH=CH$_2$(CH$_2$)$_5$CH$_2$O), 26.2 (CH=CH$_2$(CH$_2$)$_5$CH$_2$O), 16.14 (C6''). ESI MS: m/z calcd [C$_{68}$H$_{78}$O$_{15}$]Na$^+$: 1157.5233. Found: 1157.5237.

Synthesis of 7-Octen-1-yl 3-O-[3-O-(2-N-Acetyl-2-deoxy-3,4,6-tetra-O-acetyl-α-D-galactopyranosyl)-4,6-O-benzylidene-2-O-(2,3,4-tri-O-benzyl-α-L-fucopyranosyl)-β-D-galactopyranosyl]-2-O-benzyl-4,6-O-benzylidene-β-D-galactopyranoside (V-16)

A solution of the acceptor V-14 (359 mg, 0.292 mmol) in dry Et$_2$O (15 mL) was treated with 4 Å molecular sieves (300 mg) and the mixture stirred (rt, 1 h). The mixture was then cooled (–10° C.), treated with TMSOTf (10 μL, 0.058 mmol); the trichloroacetimidate (Gerhard, G., Schmidt, R. R. *Liebigs Ann.*, 1984, 1826-1847) (V-15) (457 mg, 0.965 mmol) in dry Et$_2$O (15 mL) was then added drop-wise and the mixture allowed to stand (20 min). The mixture was neutralized with Et$_3$N (0.5 mL), filtered, concentrated and subjected to flash chromatography (EtOAc/hexanes, 1:3) to afford the partially pure tetrasaccharide as a colourless oil (270 mg, 65%). The residue was taken up in pyridine (4 mL) and treated with AcSH (2 mL) and the solution was stirred (3 d). The solution was concentrated and subjected to flash chromatography (CH$_2$Cl$_2$/CH$_3$OH, 20:1) to afford V-16 as a colourless oil (205 mg, 78%). [α]+11.7 (c=0.6, CH$_2$Cl$_2$); R$_f$ 0.38 (EtOAc/hexanes, 3:1); $^1$H NMR (500 MHz): δ$_H$ 7.59-7.11 (30H, m, Ph), 5.89-5.77 (1H, m, CH$_2$=CH), 5.57 (1H, d, J$_{NH}$ 10.8 NH), 5.51 (1H, d, J$_{1'',2''}$ 3.7, H1''), 5.55 (1H, s, PhCH), 5.44 (1H, s, PhCH), 5.13-5.08 (2H, m, H1''', PhCH$_2$), 5.07-5.02 (3H, m, H1', H4''', CH=CH$_2$), 4.92-5.01 (3H, m, H3''', PhCH$_2$, CH=CH$_2$), 4.90, 4.89 (2H, AB, J 10.0, PhCH$_2$), 4.79 (1H, A of AB, J 11.4, PhCH$_2$), 4.78 (1H, A of AB, J 12.2, PhCH$_2$), 4.64 (1H, ddd, J$_{NH}$ 10.8, J$_{2''',3'''}$ 10.6, J$_{1''',2'''}$ 3.6, H2'''), 4.52 (1H, A of AB, J 11.8, PhCH$_2$), 4.45 (1H, d, J$_{1,2}$ 7.8, H1), 4.44-4.39 (2H, m, H5'', PhCH$_2$), 4.35-4.22 (5H, m, H3', H4, H4', H6, H6'), 4.18 (1H, dd, J$_{2'',3''}$ 10.2, J$_{1'',2''}$ 3.7, H2''), 4.13-4.01 (6H, m, H3, H3'', H5''', H6, H6', CH=CH$_2$(CH$_2$)$_5$CH$_2$O), 3.87-3.81 (2H, m, H2, H2'), 3.71 (1H, dd, J$_{6''',6'''}$ 11.5, J$_{5''',6'''}$ 7.8, H6'''), 3.57 (1H, ddd, J 9.1, 7.0, 7.0, CH=CH$_2$(CH$_2$)$_5$CH$_2$O), 3.32 (1H, s, H4''), 3.40, 3.27 (2H, 2×s, H5, H5'), 3.10 (1H, dd, J$_{6''',6'''}$ 11.5, J$_{5''',6'''}$ 2.6, H6'''), 2.09, 1.97, 1.78, 1.57 (12H, 4×s, CH$_3$C=O), 2.12-2.04 (2H, m, CH=CH$_2$(CH$_2$)$_5$CH$_2$O), 1.80-1.67 (2H, m, CH=CH$_2$(CH$_2$)$_5$CH$_2$O), 1.53-1.35 (6H, m, CH=CH$_2$(CH$_2$)$_5$CH$_2$O), 0.56 (3H, d, J$_{5'',6''}$ 6.2, H6''); $^{13}$C NMR (100 MHz): δ$_C$ 170.7 (C=O), 170.3 (C=O), 170.1 (C=O), 170.0 (C=O), 139.3 (Ph), 139.0 (CH$_2$=CH), 138.9 (Ph), 138.41 (2C, Ph), 138.39 (Ph), 137.4 (Ph), 129.4 (Ph), 129.2 (Ph), 128.72 (Ph), 128.71 (Ph), 128.33 (Ph), 128.30 (Ph), 128.26 (Ph), 128.23 (Ph), 128.17 (2C, Ph), 128.0 (Ph), 127.9 (Ph), 127.44 (Ph), 127.38 (Ph), 127.2 (Ph), 127.1 (Ph), 126.9 (Ph), 126.0 (Ph), 114.3 (CH$_2$=CH), 103.8 (C1), 102.0, 101.6, 100.7 (C1', PhCH), 98.1 (C1''), 92.1 (C1'''), 80.2, 79.8 (C2, C3), 78.2 (C4''), 75.3 (PhCH$_2$), 75.0 (PhCH$_2$), 74.1 (PhCH$_2$), 72.2 (PhCH$_2$), 76.3, 76.1, 76.0, 75.0, 70.7, 69.9 (C2', C2'', C3', C3'', C4, C4'), 70.3 (CH=CH$_2$(CH$_2$)$_5$CH$_2$O), 69.2, 69.0 (C6, C6'), 68.9 (C3'''), 67.6 (C4'''), 67.3 (C5''), 66.9 (C5'''), 66.5, 66.2 (C5, C5'), 62.5 (C6'''), 46.4 (C2''), 33.8 (CH=CH$_2$(CH$_2$)$_5$CH$_2$O), 29.8 (CH=CH$_2$(CH$_2$)$_5$CH$_2$O), 29.0 (CH=CH$_2$(CH$_2$)$_5$CH$_2$O), 28.9 (CH=CH$_2$(CH$_2$)$_5$CH$_2$O), 26.2 (CH=CH$_2$(CH$_2$)$_5$CH$_2$O), 22.8 (CH$_3$C=O), 20.74 (CH$_3$C=O), 20.71 (CH$_3$C=O), 20.66 (CH$_3$C=O), 15.91 (C6''). ESI MS: m/z calcd [C$_{82}$H$_{97}$NO$_{23}$]Na$^+$: 1486.6344. Found: 1486.6348.

Synthesis of 7-Octen-1-yl 3-O-[3-O-(2-N-Acetyl-2-deoxy-α-D-galactopyranosyl)-2-O-(α-L-fucopyranosyl)-β-D-galactopyranosyl]-β-D-galactopyranoside (V-17)

A stirred solution of the tetrasaccharide V-16 (186 mg, 0.154 mmol) in CH$_3$OH (25 mL) was treated with a catalytic amount of NaOCH$_3$ in CH$_3$OH and the solution was stirred (2 h). The solution was neutralized with Amberlite IR 120 (H$^+$), filtered and the residue subjected to flash chromatography (Iatrobeads, CH$_2$Cl$_2$/CH$_3$OH, 9:1) to afford the triol (162 mg, 96%) as a colourless oil. Redistilled liquid ammonia (20 mL) was collected in a flask cooled to (–78° C.) and treated with sodium until the blue colour persisted. A solution of the tetrasaccharide (160 mg, 0.063 mmol) in THF (4 mL) and CH$_3$OH (29 μL, 0.120 mmol) was added drop-wise and the mixture was stirred (–78° C., 1 h). The reaction was then quenched by the addition of CH$_3$OH (4 mL) and the ammonia evaporated to dryness. The solution was taken up in CH$_3$OH (100 mL), neutralized with Amberlite IR 120 (H$^+$), filtered and the residue subjected to C-18 chromatography (CH$_3$OH/H$_2$O, 1:1) to afford the fully deprotected tetrasaccharide V-17 (85 mg, 90%) as a colourless oil. [α]+24.4 (c=0.3, CH$_3$OH); NMR (500 MHz, CD$_3$OD): δ$_H$ 5.85-5.75 (1H, m, CH$_2$=CH), 5.30 (1H, d, 3.8, H1''), 5.16 (1H, d, J$_{1''',2'''}$ 3.7, H1'''), 5.01-4.93 (1H, m, CH=CH$_2$), 4.93-4.88 (1H, m, CH=CH$_2$), 4.67 (1H, d, J$_{1',2'}$ 7.7, H1'), 4.65 (1H, q, J$_{5'',6''}$ 6.5, H5''), 4.22 (1H, d, J$_{1,2}$ 6.9, H1), 4.01 (1H, dd, J$_{2',3'}$ 9,7, J$_{2',3'}$ 7.7, H2'), 4.34-4.30, 4.20-4.09, 3.95-3.80, 3.63-3.47 (22H, 4×m, H2, H2'', H2''', H3, H3', H3'', H3''', H4, H4', H4'', H4''', H5, H5', H5''', H6, H6', H6''', CH=CH$_2$(CH$_2$)$_5$CH$_2$O), 2.01 (3H, s, CH$_3$C=O), 2.09-2.00 (2H, m, CH=CH$_2$(CH$_2$)$_5$CH$_2$O), 1.69-1.58 (2H, m, CH=CH$_2$(CH$_2$)$_5$CH$_2$O), 1.45-1.26 (6H, m, CH=CH$_2$(CH$_2$)$_5$CH$_2$O), 1.22 (3H, d, J$_{5',6'}$ 6.5, H6''); $^{13}$C NMR (125 MHz, CD$_3$OD): δ$_C$ 174.4 (C=O), 140.1 (CH$_2$=CH), 114.8 (CH$_2$=CH), 105.02, 104.96 (C1, C1'), 100.2 (C1''), 93.7 (C1'''), 84.2, 77.8, 76.3, 76.2, 74.0, 73.8, 72.8, 71.7, 71.6, 70.5, 70.33, 70.25, 70.0, 68.1, 64.8 (C2, C2', C2'', C3, C3', C3", C3'", C4, C4', C4", C4'", C5, C5', C5", C5'"), 70.8 (CH=CH$_2$(CH$_2$)$_5$CH$_2$O), 63.4, 62.54, 62.51 (C6, C6', C6'"), 51.30 (C2'"), 34.9 (CH=CH$_2$(CH$_2$)$_5$CH$_2$O), 30.8 (2C, CH=CH$_2$(CH$_2$)$_5$CH$_2$O), 30.1 (CH=CH$_2$(CH$_2$)$_5$CH$_2$O), 27.0 (CH=CH$_2$(CH$_2$)$_5$CH$_2$O), 22.9 (CH$_3$C=O), 16.8 (C6"). ESI MS: m/z calcd [C$_{34}$H$_{59}$NO$_{20}$]Na$^+$: 824.3523. Found: 824.3513.

Example 3

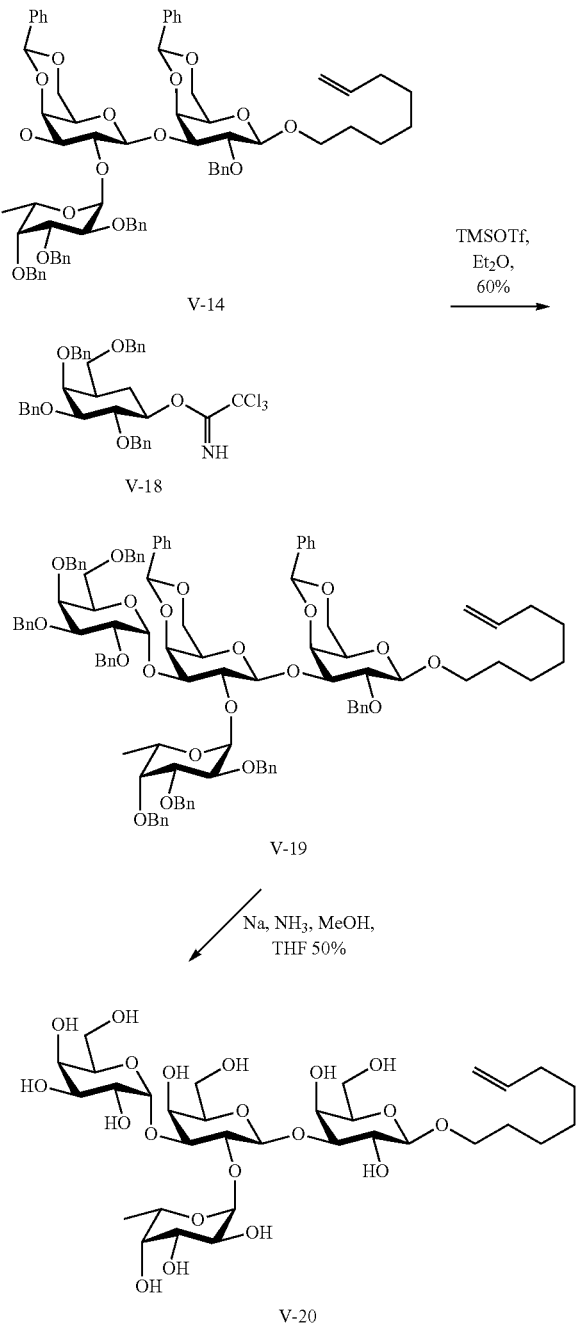

Synthesis of 7-Octen-1-yl 2-O-Benzyl-3-O-[4,6-O-benzylidene-3-O-(2,3,4,6-tetra-O-benzyl-α-D-galactopyranosyl)-2-O-(2,3,4-tri-O-benzyl-α-L-fucopyranosyl)-β-D-galactopyranosyl]-4,6-O-benzylidene-β-D-galactopyranoside (V-19)

A solution of the acceptor V-14 (310 mg, 0.273 mmol) in dry Et$_2$O (5 mL) was treated with 4 Å molecular sieves and the mixture stirred (rt, 1 h). The mixture was then cooled (−10° C.), treated with TMSOTf (10 µL, 0.058 mmol); the trichloroacetimidate (Wegmann, B., Schmidt, R. R. *J. Carbohydr. Chem.*, 1987, 6:357-375) (V-18) (700 mg, 1.02 mmol) in dry Et$_2$O (10 mL) was then added drop-wise and the mixture allowed to stand (20 min). The mixture was neutralized with Et$_3$N (0.5 mL), filtered, concentrated and subjected to flash chromatography (EtOAc/hexanes, 1:4) to afford the partially pure tetrasaccharide V-19 (270 mg, 60%) as a colourless oil.

Synthesis of 7-Octen-1-yl 3-O-[2-O-(α-L-Fucopyranosyl)-3-O-(α-D-galactopyranosyl)-β-D-galactopyranosyl]-β-D-galactopyranoside (V-20)

Redistilled liquid ammonia (20 mL) was collected in a flask cooled to −78° C. and treated with sodium until the blue colour persisted. A solution of the tetrasaccharide V-19 (260 mg, 0.157 mmol) in THF (4 mL) and CH$_3$OH (63 µL, 1.57 mmol) was added drop-wise and the solution was stirred (−78° C., 1 h). The reaction was then quenched by the addition of CH$_3$OH (4 mL) and the ammonia evaporated to dryness. The solution was taken up in CH$_3$OH (100 mL), neutralized with Amberlite IR 120 (H$^+$), filtered and the residue subjected to chromatography (Iatrobeads, CH$_2$Cl$_2$/CH$_3$OH, 1:1) to afford the first unreacted V-19 (104 mg, 40%); further elution (CH$_2$Cl$_2$/CH$_3$OH, 2:1) afforded the fully deprotected compound V-20 (60 mg, 50%). [α]+7.2 (c=0.2, CH$_3$OH); $^1$H NMR (500 MHz, CD$_3$OD): δ$_H$ 5.85-5.75 (1H, m, CH$_2$=CH), 5.29 (1H, d, J$_{1",2"}$ 3.8, H1"), 5.16 (1H, d, J$_{1'",2'"}$ 3.6, H1'"), 5.01-4.94 (1H, m, CH=CH$_2$), 4.93-4.88 (1H, m, CH=CH$_2$), 4.67 (1H, d, J$_{1',2'}$ 7.5, H1'), 4.61 (1H, q, J$_{5",6"}$ 6.3, H5"), 4.23 (1H, d, J$_{1,2}$ 7.0, H1), 4.01 (1H, dd, J$_{2',3'}$ 8.1, 7.5, H2'), 4.19-4.09, 3.97-3.65, 3.64-3.49 (22H, 3×m, H2, H2", H2'", H3, H3', H3", H3'", H4, H4', H4", H4'", H5, H5', H5'", H6, H6', H6'", CH=CH$_2$(CH$_2$)$_5$CH$_2$O), 2.08-2.00 (2H, m, CH=CH$_2$ (CH$_2$)$_5$CH$_2$O), 1.66-1.57 (2H, m, CH=CH$_2$(CH$_2$)$_5$CH$_2$O), 1.45-1.27 (6H, m, CH=CH$_2$(CH$_2$)$_5$CH$_2$O), 0.56 (3H, d, J$_{5",6"}$ 6.3, H6"); $^{13}$C NMR (125 MHz, CD$_3$OD): δ$_C$ 140.1 (CH$_2$=CH), 114.8 (CH$_2$=CH), 105.04, 104.98 (C1, C1'), 100.3 (C1"), 96.1 (C1'"), 84.3, 79.4, 76.3, 76.0, 74.4, 73.8, 73.1, 71.64, 71.61, 71.4, 71.2, 70.32, 70.30, 70.0, 68.0, 66.6 (C2, C2', C2", C2'", C3, C3', C3", C3'", C4, C4', C4", C4'", C5, C5', C5", C5'"), 70.8 (CH=CH$_2$(CH$_2$)$_5$CH$_2$O), 63.3, 62.56, 62.54 (C6, C6', C6'"), 34.9 (CH=CH$_2$(CH$_2$)$_5$CH$_2$O), 30.8 (CH=CH$_2$(CH$_2$)$_5$CH$_2$O), 30.10 (2C, CH=CH$_2$ (CH$_2$)$_5$CH$_2$O), 27.0 (CH=CH$_2$(CH$_2$)$_5$CH$_2$O), 16.7 (C6"). ESI MS: m/z calcd [C$_{32}$H$_{56}$O$_{20}$]Na$^+$: 783.3257. Found: 783.3258.

Example 4
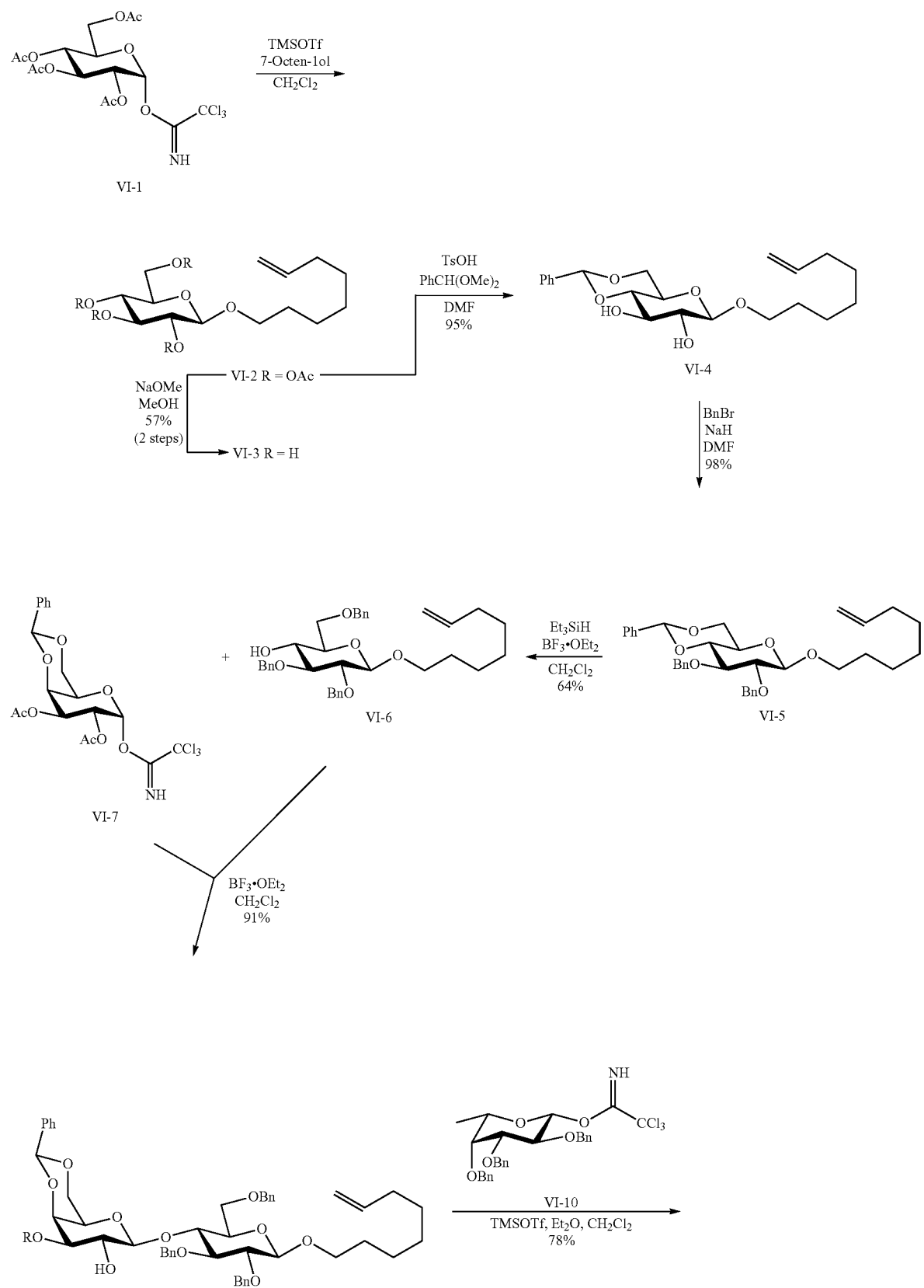

-continued
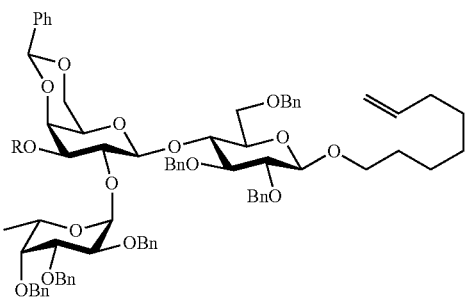
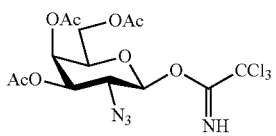
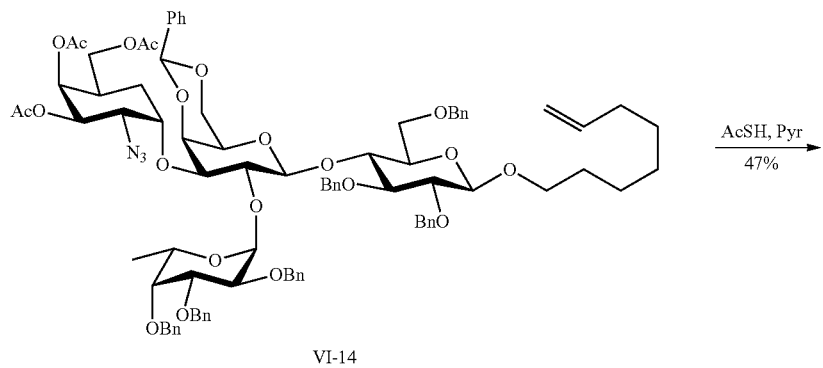
VI-14
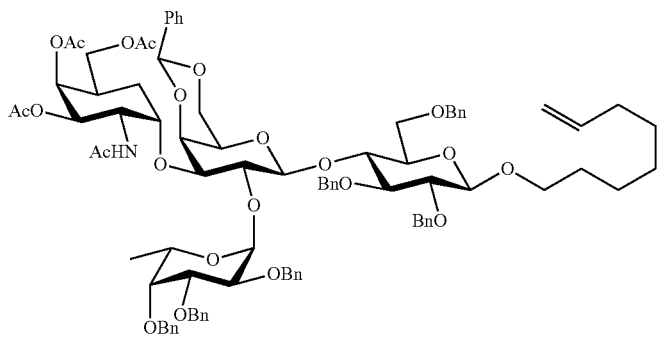
VI-15
1. NaOMe, MeOH, 95%
2. Na, NH$_3$, MeOH, THF, 90%

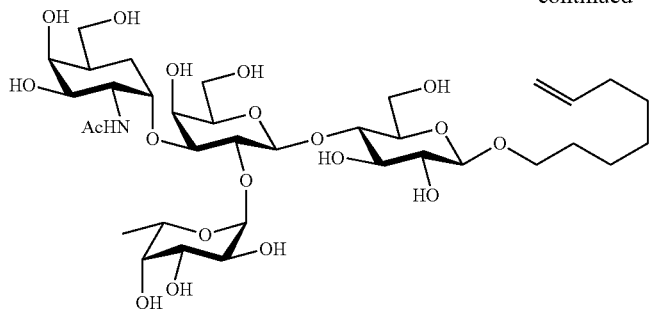

VI-16

Synthesis of 7-Octen-1-yl 4,6-O-Benzylidene-β-D-glucopyranoside (VI-4)

A stirred solution of 2,3,4,6-tetra-O-acetyl-α-D-glucopyranosyl trichloroacetimidate (Schmidt, R. R., Josef, M. *Angew. Chem.*, 1980, 92:763) VI-1 (33.9 g, 69 mmol) and 7-octen-1-ol (11.0 g, 86 mmol) was treated with 4 Å molecular sieves (5 g) and the mixture stirred (rt, 1 h). The mixture was then cooled (−40° C.), treated with TMSOTf (0.5 mL) and the mixture was allowed to warm (rt, 1 h). The reaction was quenched by the addition of Et$_3$N (2 mL), filtered and subjected to flash chromatography (EtOAc/hexanes, 2:3) to afford a colourless oil. The oil was taken up in CH$_3$OH (200 mL), treated with a catalytic amount of NaOCH$_3$ in CH$_3$OH and stirred (rt, 2 h); the NaOCH$_3$ was neutralized with Amberlite IR120 (H$^+$), filtered and then concentrated. The residue was subjected to flash chromatography (EtOAc/hexanes, 5:1) to afford the tetrol VI-3 as a white solid (11.3 g, 57%), which was immediately used in the subsequent step. A solution of the tetrol VI-3 (11.3 g, 38.9 mmol) in dry DMF (200 mL) was treated with benzaldehyde dimethyl acetal (7.2 mL, 48 mmol), p-TsOH (300 mg) and the solution was stirred (40° C., 18 h). The solution was neutralized with Et$_3$N (1.5 mL), concentrated and subjected to flash chromatography (EtOAc/hexanes, 1:1) to afford the diol VI-4 (14.0 g, 95%) as a white solid. Mp 149-151° C.; [α]−46.8 (c=0.3, CH$_2$Cl$_2$); R$_f$ 0.82 (EtOAc/hexanes, 7:10); $^1$H NMR (500 MHz): δ$_H$ 7.52-7.48 (2H, m, Ph), 7.41-7.35 (3H, m, Ph), 5.86-5.77 (1H, m, CH═CH$_2$), 5.55 (1H, s, PhCH), 5.03-4.92 (2H, m, CH═CH$_2$), 4.41 (1H, d, J$_{1,2}$ 8.0, HD, 4.35 (1H, dd, J$_{6,6}$ 10.5, J$_{5,6}$ 4.9, H6), 3.93-3.77 (3H, m, H3, H6, CH═CH$_2$(CH$_2$)$_5$CH$_2$O), 3.61-3.43 (4H, m, H2, H4, H5, CH═CH$_2$(CH$_2$)$_5$CH$_2$O), 2.71 (1H, d, J 2.2, OH), 2.51 (1H, d, J 2.4, OH), 2.10-2.01 (2H, m, CH═CH$_2$(CH$_2$)$_5$CH$_2$O), 1.71-1.59 (2H, m, CH═CH$_2$(CH$_2$)$_5$CH$_2$O), 1.47-1.28 (6H, m, CH═CH$_2$(CH$_2$)$_5$CH$_2$O); $^{13}$C NMR (125 MHz): δ$_C$ 139.0 (CH═CH$_2$), 136.9 (Ph), 129.3 (Ph), 128.3 (Ph), 126.3 (Ph), 114.3 (CH═CH$_2$), 103.1 (C1), 101.9 (PhCH), 80.6 (C4), 73.2, 70.5, 64.6 (C2, C3, C5), 68.7 (CH═CH$_2$(CH$_2$)$_5$CH$_2$O), 66.4 (C6), 33.7 (CH═CH$_2$(CH$_2$)$_5$CH$_2$O), 29.5 (CH═CH$_2$(CH$_2$)$_5$CH$_2$O), 28.83 (CH═CH$_2$(CH$_2$)$_5$CH$_2$O), 28.77 (CH═CH$_2$(CH$_2$)$_5$CH$_2$O), 25.8 (CH═CH$_2$(CH$_2$)$_5$CH$_2$O). ESI MS: m/z calcd [C$_{21}$H$_{30}$O$_6$]Na$^+$: 401.1935. Found: 401.1934.

Synthesis of 7-Octen-1-yl 4,6-O-Benzylidene-2,3-di-O-benzyl-β-D-glucopyranoside (VI-5)

A stirred solution of the diol VI-4 (13.0 g, 34.4 mmol) in DMF (200 mL, −20° C.) was treated with BnBr (12.2 mL, 0.103 mmol) and NaH (60%, 3.44 g, 86 mmol) and the mixture stirred (rt, 6 h). The mixture was cooled (−20° C.), treated with CH$_3$OH (10 mL) and allowed to stand (rt, 10 min). The solution was concentrated, taken up in EtOAc (500 mL) and washed with water (400 mL), and brine (400 mL). The organic extract was dried and then concentrated and subjected to flash chromatography (EtOAc/hexanes, 1:9) to afford the dibenzyl ether VI-5 as a white solid (18.8 g, 98%). Mp 49-51° C.; [α]−27.8 (c=1.2, CH$_2$Cl$_2$); R$_f$ 0.56 (EtOAc/hexanes, 1:5); $^1$H NMR (500 MHz): δ$_H$ 7.52-7.49 (2H, m, Ph), 7.43-7.26 (13H, m, Ph), 5.86-5.76 (1H, m, CH═CH$_2$), 5.59 (1H, s, PhCH), 5.04-4.91 (4H, m, PhCH$_2$, CH═CH$_2$), 4.83 (1H, A of AB, J 10.9, PhCH$_2$), 4.79 (1H, A of AB, J 11.0, PhCH$_2$), 4.57 (1H, d, J$_{1,2}$ 7.9, H1), 4.37 (1H, dd, J$_{6,6}$ 10.3, J$_{5,6}$ 5.1, H6), 3.93 (1H, ddd, J 9.4, 6.5, 6.5, CH═CH$_2$(CH$_2$)$_5$CH$_2$O), 3.81 (1H, dd, J$_{6,6}$ 10.3, J$_{5,6}$ 5.1, H6), 3.77 (1H, dd, J$_{2,3}$ 8.6, J$_{3,4}$ 9.1, H3), 3.71 (1H, dd, J$_{4,5}$ 9.2, J$_{3,4}$ 9.1, H4), 3.58 (1H, ddd, 1H, J 9.4, 6.9, 9.4, CH═CH$_2$(CH$_2$)$_5$CH$_2$O), 3.48 (1H, dd, J$_{2,3}$ 8.6, J$_{1,2}$ 7.9, H2), 3.43 (1H, ddd, J$_{5,6}$ 9.9, J$_{4,5}$ 9.4, J$_{5,6}$ 5.1, H5), 2.09-2.02 (2H, m, CH═CH$_2$(CH$_2$)$_5$CH$_2$O), 1.72-1.62 (2H, m, CH═CH$_2$(CH$_2$)$_5$CH$_2$O), 1.47-1.31 (6H, m, CH═CH$_2$(CH$_2$)$_5$CH$_2$O); $^{13}$C NMR (125 MHz): δ$_C$ 139.0 (CH═CH$_2$), 138.6 (Ph), 138.4 (Ph), 137.4 (Ph), 128.9 (Ph), 128.4 (Ph), 128.32 (Ph), 128.27 (Ph), 128.2 (Ph), 128.0 (Ph), 127.7 (Ph), 127.6 (Ph), 126.0 (Ph), 114.3 (CH═CH$_2$), 104.2 (C1), 101.1 (PhCH), 82.2, 81.5, 90.9 (C2, C3, C4), 75.3 (PhCH$_2$), 75.1 (PhCH$_2$), 70.6 (CH═CH$_2$(CH$_2$)$_5$CH$_2$O), 68.8 (C6), 66.0 (C5), 33.7 (CH═CH$_2$(CH$_2$)$_5$CH$_2$O), 29.7 (CH═CH$_2$(CH$_2$)$_5$CH$_2$O), 28.9 (CH═CH$_2$(CH$_2$)$_5$CH$_2$O), 28.8 (CH═CH$_2$(CH$_2$)$_5$CH$_2$O), 26.0 (CH═CH$_2$(CH$_2$)$_5$CH$_2$O). ESI MS: m/z calcd [C$_{35}$H$_{42}$O$_6$]Na$^+$: 581.2874. Found: 581.2876.

Synthesis of 7-Octen-1-yl 2,3,6-Tri-O-benzyl-β-D-glucopyranoside (VI-6)

A stirred solution of the alkene VI-5 (7.47 g, 13.3 mmol) in dry CH$_2$Cl$_2$ (200 mL) was treated with 4 Å molecular sieves (5 g) and the mixture stirred (rt, 1 h). The mixture was then cooled (0° C.) and treated with triethylsilane (10.7 mL, 66.9 mmol) and BF$_3$.OEt$_2$ (3.3 mL, 26.6 mm and the mixture stirred (rt, 5 h). The mixture was neutralized with Et$_3$N (5 mL), diluted with CH$_2$Cl$_2$ (300 mL) and washed with saturated NaHCO$_3$, water and then brine. The organic extract was concentrated and subjected to flash chromatography (EtOAc/hexanes, 1:4) to afford the alcohol VI-6 as a colourless oil (4.7 g, 64%). [α]−18.0 (c=0.3, CH$_2$Cl$_2$); R$_f$ 0.73 (EtOAc/hexanes, 3:7); $^1$H NMR (500 MHz): δ$_H$ 7.40-7.26 (15H, m, Ph), 5.87-5.76 (1H, m, CH═CH$_2$), 5.03-4.93 (4H, m, PhCH$_2$, CH═CH$_2$), 4.75 (1H, A of AB, J 11.4, PhCH$_2$), 4.73 (1H, A of AB, J 10.7, PhCH$_2$), 4.62, 4.58 (2H, AB, J 12.3, PhCH$_2$), 4.43 (1H, d, J$_{1,2}$ 7.2, H1), 3.99-3.93 (1H, m, CH═CH$_2$ (CH$_2$)$_5$CH$_2$O), 3.79 (1H, dd, J$_{6,6}$ 10.4, J$_{5,6}$ 3.9, H6), 3.72 (1H, dd, J$_{6,6}$ 10.4, J$_{5,6}$ 5.4, H6), 3.63-3.52 (2H, m, H4, CH=CH$_2$(CH$_2$)$_5$CH$_2$O), 3.50-3.40 (3H, m, H2, H3, H5), 2.54 (1H, d, J 2.1, OH), 2.09-2.01 (2H, m, CH=CH$_2$(CH$_2$)$_5$CH$_2$O), 1.72-1.62 (2H, m, CH=CH$_2$(CH$_2$)$_5$CH$_2$O), 1.47-1.30 (6H, m, CH=CH$_2$(CH$_2$)$_5$CH$_2$O); $^{13}$C NMR (125 MHz): δ$_C$ 139.0 (CH=CH$_2$), 138.7 (Ph), 138.5 (Ph), 138.0 (Ph), 128.5 (Ph), 128.40 (Ph), 128.36 (Ph), 128.1 (Ph), 128.0 (Ph), 127.8 (Ph), 127.71 (Ph), 127.69 (2C, Ph), 114.2 (CH=CH$_2$), 103.7 (C1), 84.1, 81.7 (C2, C3), 75.3 (PhCH$_2$), 74.7 (PhCH$_2$), 74.0 (C4), 73.7 (PhCH$_2$), 71.7 (C5), 70.4, 70.2 (C6, CH=CH$_2$(CH$_2$)$_5$CH$_2$O), 33.7 (CH=CH$_2$(CH$_2$)$_5$CH$_2$O), 29.7 (CH=CH$_2$(CH$_2$)$_5$CH$_2$O), 28.9 (CH=CH$_2$(CH$_2$)$_5$CH$_2$O), 28.8 (CH=CH$_2$(CH$_2$)$_5$CH$_2$O), 26.0 (CH=CH$_2$(CH$_2$)$_5$CH$_2$O). ESI MS: m/z calcd [C$_{35}$H$_{44}$O$_6$]Na$^+$: 583.3030. Found: 583.3031.

Synthesis of 7-Octen-1-yl 4-O-(4,6-o-Benzylidene-β-D-galactopyranosyl)-2,3,6-tri-O-benzyl-β-D-glucopyranoside (VI-8)

A solution of the acceptor VI-6 (4.02 g, 7.19 mmol) in dry CH$_2$Cl$_2$ (50 mL) was stirred over 4 Å molecular sieves (rt, 1 h). The solution was then cooled (−40° C.), treated with BF$_3$.OEt$_2$ (0.5 mL) followed by drop-wise addition of the trichloroacetimidate (Figueroa-Pérez, S., Vérez-Bencomo, V. *Carbohydr. Res.*, 1999, 317:29-38) (VI-7) (8.90 g, 18.0 mmol) and then the mixture was allowed to warm (0° C.). The mixture was neutralized with Et$_3$N (2 mL), concentrated and subjected to flash chromatography (EtOAc/hexanes, 1:1) to afford a colourless oil, which was immediately used in the next step. The colourless oil was taken up in CH$_3$OH (100 mL), treated with a solution of NaOCH$_3$ in CH$_3$OH and stirred (rt, 3 h). The solution was neutralized with Amberlite IR 120 (H$^+$), filtered and subjected to flash chromatography (EtOAc/hexanes, 7:3) to afford the diol VI-8 as a colourless oil (5.3 g, 91%). [α]−3.1 (c=1.4, CH$_2$Cl$_2$); R$_f$ 0.68 (EtOAc/hexanes, 7:3); $^1$H NMR (500 MHz): δ$_H$ 7.50-7.21 (20H, m, Ph), 5.86-5.77 (1H, m, CH$_2$=CH), 5.46 (1H, s, PhCH), 5.03-4.91 (5H, m, PhCH$_2$, CH$_2$=CH), 4.73 (1H, A of AB, J 10.1, PhCH$_2$), 4.74, 4.62 (2H, AB, J 12.3, PhCH$_2$), 4.58 (1H, d, J$_{1,2}$ 8.5, H1'), 4.40 (1H, d, J$_{1,2}$ 8.1, H1), 4.06-3.99 (4H, m, H4, H4', H6, H6'), 3.95 (1H, ddd, J 9.5, 6.4, 6.4, CH=CH$_2$(CH$_2$)$_5$CH$_2$O), 3.80 (1H, dd, J$_{6,6}$ 11.6, J$_{5,6}$ 1.9, H6), 3.75 dd, J$_{6',6'}$ 12.5, J$_{5',6'}$ 1.5, H6'), 3.73-3.68 (2H, m, H3, H5), 3.64 (1H, dd, J$_{2',3'}$ 9.0, J$_{1',2'}$ 8.5, H2'), 3.54 (1H, ddd, J 9.5, 6.8, 6.8, CH=CH$_2$(CH$_2$)$_5$CH$_2$O), 3.51-3.44 (3H, m, H2, H3', OH), 2.87 (1H, s, H5'), 2.49 (1H, d, J 7.3, OH), 2.10-2.01 (2H, m, CH=CH$_2$(CH$_2$)$_5$CH$_2$O), 1.74-1.61 (2H, m, CH=CH$_2$(CH$_2$)$_5$CH$_2$O), 1.49-1.29 (6H, m, CH=CH$_2$(CH$_2$)$_5$CH$_2$O); $^{13}$C NMR (125 MHz): δ$_C$ 139.2 (CH$_2$=CH), 139.0 (Ph), 138.4 (Ph), 137.69 (Ph), 137.67 (Ph), 129.1 (Ph), 128.4 (Ph), 128.3 (Ph), 128.2 (Ph), 128.1 (2C, Ph), 128.0 (Ph), 127.8 (Ph), 127.6 (Ph), 127.2 (2C, Ph), 126.4 (Ph), 114.3 (CH$_2$=CH), 103.9, 103.5 (C1, C1'), 101.3 (PhCH), 83.7 (C3), 82.1 (C2), 77.6 (C4), 75.2 (PhCH$_2$), 75.1, 74.2 (C4', C5), 74.9 (PhCH$_2$), 73.5 (PhCH$_2$), 72.7, 72.5 (C2', C3'), 70.10 (CH=CH$_2$(CH$_2$)$_5$CH$_2$O), 68.9, 68.5 (C6, C6'), 66.7 (C5'), 33.7 (CH=CH$_2$(CH$_2$)$_5$CH$_2$O), 29.7 (CH=CH$_2$(CH$_2$)$_5$CH$_2$O), 28.9 (CH=CH$_2$(CH$_2$)$_5$CH$_2$O), 28.8 (CH=CH$_2$(CH$_2$)$_5$CH$_2$O), 26.1 (CH=CH$_2$(CH$_2$)$_5$CH$_2$O). ESI MS: m/z calcd [C$_{48}$H$_{58}$O$_{11}$]Na$^+$: 833.3871. Found: 833.3872.

Synthesis of 7-Octen-1-yl 4-O-(4,6-O-Benzylidene-3-O-pivaloyl-β-D-galactopyranosyl)-2,3,6-tri-O-benzyl-β-D-glucopyranoside (VI-9)

A stirred solution of the diol VI-8 (5.93 g, 3.72 mmol) in pyridine (50 mL) was treated with trimethylacetal chloride (1.16 mL, 9.52 mmol) and the solution was stirred. The solution was concentrated and subjected to flash chromatography (EtOAc/hexanes, 1:1) to afford the alcohol VI-9 as a white solid (6.22 g, 95%). [α]+42.4 (c=0.5, CH$_2$Cl$_2$); R$_f$ 0.55 (EtOAc/hexanes, 3:2); $^1$H NMR (500 MHz): δ$_H$ 7.52-7.18 (20H, m, Ph), 5.86-5.77 (1H, m, CH$_2$=CH), 5.40 (1H, s, PhCH), 5.05-4.90 (5H, m, CH$_2$=CH, PhCH$_2$), 4.73 (1H, A of AB, J 11.9, PhCH$_2$), 4.72 (1H, A of AB, J 10.9, PhCH$_2$), 4.67-4.63 (2H, m, H1', H3'), 4.59 (1H, A of AB, J 12.4, PhCH$_2$), 4.39 (1H, d, J$_{1,2}$ 7.8, H1), 4.17 (1H, d, J$_{3',4'}$ 3.7, H4'), 4.04-3.90 (4H, m, H4, H6, H6', CH=CH$_2$(CH$_2$)$_5$CH$_2$O), 3.87 (1H, dd, J$_{2',3'}$ 9.7, J$_{1',2'}$ 7.9, H2'), 3.78 (1H, dd, J$_{6,6}$ 11.6, J$_{5,6}$ 2.0, H6), 3.73-3.65 (2H, m, H3, H6'), 3.49-3.42, 3.60-3.50 (4H, 2×m, H2, H5, OH, CH=CH$_2$(CH$_2$)$_5$CH$_2$O), 2.81 (1H, s, H5'), 2.09-2.01 (2H, m, CH=CH$_2$(CH$_2$)$_5$CH$_2$O), 1.72-1.61 (2H, m, CH=CH$_2$(CH$_2$)$_5$CH$_2$O), 1.47-1.31 (6H, m, CH=CH$_2$(CH$_2$)$_5$CH$_2$O), 1.22 (9H, s, (CH$_3$)$_3$C); $^{13}$C NMR (125 MHz): δ$_C$ 178.3 (C=O), 139.2 (Ph), 139.0 (CH$_2$=CH), 138.4 (Ph), 137.9 (Ph), 137.5 (Ph), 128.6 (Ph), 128.4 (Ph), 128.3 (Ph), 128.2 (Ph), 128.14 (Ph), 128.12 (Ph), 127.92 (Ph), 127.86 (Ph), 127.6 (Ph), 127.1 (Ph), 126.9 (Ph), 126.0 (Ph), 114.3 (CH$_2$=CH), 103.9 (2C, C1, C1'), 100.4 (PhCH), 83.9 (C3), 82.2 (C2), 77.7 (C4), 75.1 (PhCH$_2$), 74.8 (PhCH$_2$), 74.0, 73.4, 73.1 (C3', C4', C5), 73.7 (PhCH$_2$), 70.1 (CH=CH$_2$(CH$_2$)$_5$CH$_2$O), 69.5 (C2'), 68.8 (2C, C6, C6'), 66.5 (C5'), 38.7 ((CH$_3$)$_3$C), 33.7 (CH=CH$_2$(CH$_2$)$_5$CH$_2$O), 29.7 (CH=CH$_2$(CH$_2$)$_5$CH$_2$O), 28.9 (CH=CH$_2$(CH$_2$)$_5$CH$_2$O), 28.8 (CH=CH$_2$(CH$_2$)$_5$CH$_2$O), 27.1 ((CH$_3$)$_3$C), 26.0 (CH=CH$_2$(CH$_2$)$_5$CH$_2$O). ESI MS: m/z calcd [C$_{53}$H$_{66}$O$_{12}$]Na$^+$: 917.4446. Found: 917.4449.

Synthesis of 7-Octen-1-yl 4-O-[4,6-O-Benzylidene-2-O-(2,3,4-tri-O-benzyl-α-L-fucopyranosyl)-β-D-galactopyranosyl]-2,3,6-tri-O-benzyl-β-D-glucopyranoside (VI-12)

A solution of the alcohol VI-9 (2.90 g, 3.24 mmol) in dry Et$_2$O/CH$_2$Cl$_2$ (9:1, 50 mL) was treated with 4 Å molecular sieves (2 g) and the mixture was stirred (rt, 1 h). The mixture was then cooled (−10° C.), treated with TMSOTf (100 μL) followed by drop-wise addition of the trichloroacetimidate (Schmidt, R. R., Toepfer, A. *J. Carb. Chem.*, 1993, 12:809-822) (VI-10) (5.20 g, 9.25 mmol) in dry ether (15 mL). The mixture was treated with Et$_3$N (0.5 mL), filtered and subjected to flash chromatography (EtOAc/hexanes, 1:3) to yield the trisaccharide (VI-11) as a colourless oil (3.34 g, 78%). The oil was taken up in CH$_3$OH (100 mL), treated with catalytic LiOCH$_3$ (150 mg) and the solution was heated at reflux (5 d). The solution was allowed to cool, neutralized with Amberlite IR 120 (H$^+$), filtered and subjected to flash chromatography (EtOAc/hexanes, 1:3) to afford first unreacted starting material (480 mg, 16%); further elution (EtOAc/hexanes, 1:2) afforded the alcohol VI-12 as a colourless oil (1.96 g, 68%). [α]−40.8 (c=0.4, CH$_2$Cl$_2$); R$_f$ 0.44 (EtOAc/hexanes, 3:2); $^1$H NMR (500 MHz): δ$_H$ 7.58-7.09 (35H, m, Ph), 5.87-5.76 (1H, m, CH$_2$=CH), 5.58 (1H, s, PhCH), 5.16 (1H, A of AB, J 10.4, PhCH$_2$), 5.05 (1H, d, J$_{1'',2''}$ 3.4, H1''), 5.03-5.01, 4.97-4.93 (3H, m, PhCH$_2$, CH$_2$=CH), 4.82 (1H, A of AB, J 11.6, PhCH$_2$), 4.81 (1H, A of AB, J 12.1, PhCH$_2$), 4.76-4.70 (4H, m, PhCH$_2$), 4.89, 4.64 (2H, AB, J 10.9, PhCH$_2$), 4.67, 4.43 (2H, AB, J 12.4, PhCH$_2$), 4.42 (1H, d, J$_{1',2'}$ 7.9, H1'), 4.35 (1H, d, J$_{6,6'}$ 12.4, H6), 4.34 (1H, d, J$_{1,2}$ 7.9, H1), 4.14 (1H, d, J$_{3',4'}$ 3.6, H4'), 4.07 (1H, dd, J$_{2'',3''}$ 6.8, J$_{1'',2''}$ 3.4, H2''), 4.09-4.00 (2H, m, H4, H4''), 3.98 (1H, dd, $J_{6',6'}$ 12.4, $J_{5',6'}$ 1.5, H6'), 3.97-3.87 (4H, m, H3", H5", H6, CH=CH$_2$(CH$_2$)$_5$CH$_2$O), 3.81 (1H, dd, $J_{2',3'}$ 9.7, $J_{1',2'}$ 7.9, H2'), 3.69-3.57 (3H, m, H3', H6, CH=CH$_2$(CH$_2$)$_5$CH$_2$O), 3.54-3.46 (2H, m, H3, OH), 3.41 (1H, dd, $J_{2,3}$ 9.1, $J_{1,2}$ 8.0, H2), 3.31-3.26 (1H, m, H5), 3.13 (1H, s, H5'), 2.06-2.01 (2H, m, CH=CH$_2$(CH$_2$)$_5$CH$_2$O), 1.72-1.59 (2H, m, CH=CH$_2$(CH$_2$)$_5$CH$_2$O), 1.47-1.29 (6H, m, CH=CH$_2$(CH$_2$)$_5$CH$_2$O), 1.08 (3H, d, $J_{5''',6''-}$ 6.5, H6"); $^{13}$C NMR (125 MHz): $\delta_C$ 139.0 (CH$_2$=CH), 138.8 (Ph), 138.74 (Ph), 138.69 (Ph), 138.6 (Ph), 138.3 (Ph), 138.1 (Ph), 137.5 (Ph), 129.0 (Ph), 128.9 (Ph), 128.6 (Ph), 128.43 (Ph), 128.42 (Ph), 128.32 (2C, Ph), 128.27 (Ph), 128.24 (Ph), 128.19 (Ph), 128.10 (Ph), 128.06 (Ph), 128.0 (Ph), 127.7 (Ph), 127.64 (Ph), 127.60 (Ph), 127.57 (Ph), 127.54 (Ph), 127.43 (Ph), 127.38 (Ph), 126.6 (Ph), 114.2 (CH$_2$=CH), 103.7 (C1), 101.4, 101.2 (C1', PhCH), 99.2 (C1"), 82.9, 81.7 (C2, C3), 79.0, 78.1, 77.6, 77.3, 76.3 (C2', C2', C3", C4, C4"), 75.8 (C4'), 76.0 (PhCH$_2$), 75.11 (PhCH$_2$), 75.07 (C5), 74.8 (PhCH$_2$), 74.1 (PhCH$_2$), 73.4 (PhCH$_2$), 73.0 (PhCH$_2$), 72.9 (C3'), 70.0 (CH=CH$_2$(CH$_2$)$_5$CH$_2$O), 69.0, 68.1 (C6, C6'), 67.3, 66.5 (C5', C5"), 33.7 (CH=CH$_2$(CH$_2$)$_5$CH$_2$O), 29.7 (CH=CH$_2$(CH$_2$)$_5$CH$_2$O), 29.0 (CH=CH$_2$(CH$_2$)$_5$CH$_2$O), 28.8 (CH=CH$_2$(CH$_2$)$_5$CH$_2$O), 26.0 (CH=CH$_2$(CH$_2$)$_5$CH$_2$O), 16.8 (C6"). ESI MS: m/z calcd [C$_{75}$H$_{86}$O$_{15}$]Na$^+$: 1249.5859. Found: 1249.5855.

Synthesis of 7-Octen-1-yl 4-O-[3-O-(2-N-Acetyl-2-deoxy-3,4,6-tetra-O-acetyl-α-D-galactopyranosyl)-4,6-O-benzylidene-2-O-(2,3,4-tri-O-benzyl-α-L-fucopyranosyl)-β-D-galactopyranosyl]-2,3,6-tri-O-benzyl-β-D-glucopyranoside (VI-15)

A solution of the acceptor VI-12 (365 mg, 0.321 mmol) in dry Et$_2$O (15 mL) was treated with 4 Å molecular sieves (250 mg) and the mixture stirred (rt, 1 h). The mixture was then cooled (−10° C.), treated with TMSOTf (10 µL, 0.058 mmol); the trichloroacetimidate (Gerhard, G., Schmidt, R. R. *Liebigs Ann.*, 1984, 1826-1847) (VI-13) (457 mg, 0.965 mmol) in dry Et$_2$O (15 mL) was then added drop-wise and the mixture allowed to stand (20 min). The mixture was neutralized with Et$_3$N (0.5 mL), filtered, concentrated and subjected to flash chromatography (EtOAc/hexanes, 1:3) to afford the partially pure tetrasaccharide VI-14 as a colourless oil (330 mg, 67%). The residue was taken up in pyridine (4 mL) and treated with AcSH (2 mL) and the solution was stirred (3 d). The solution was concentrated and subjected to flash chromatography (CH$_2$Cl$_2$:CH$_3$OH, 20:1) to afford VI-15 as a colourless oil (230 mg, 70%). [+]−3.4 (c=0.3, CH$_3$OH); $^1$H NMR (500 MHz): $\delta_H$ 7.55-7.12 (35H, m, Ph), 5.87-5.75 (1H, m, CH$_2$=CH), 5.47 (1H, d, $J_{1'',2''}$ 3.9, H1"), 5.43 (1H, s, PhCH), 5.42 (1H, d, J 9.7, NH), 5.23-5.17 (2H, m, PhCH$_2$), 5.10 (1H, d, $J_{1''',2'''}$ 3.7, H1'''), 5.03-4.93 (6H, m, H3''', H4''', PhCH$_2$, CH=CH$_2$), 4.89 (1H, A of AB, J 10.6, PhCH$_2$), 4.74 (1H, A of AB, J 10.5, PhCH$_2$), 4.74 (1H, A of AB, J 11.8, PhCH$_2$), 4.70-4.57 (7H, m, H1', H2", PhCH$_2$), 4.40-4.34 (2H, m, H5", H6'), 4.35 (1H, d, $J_{1,2}$ 8.0, H1), 4.29 (1H, d, $J_{3',4'}$ 3.8, H4'), 4.25 (1H, dd, $J_{2'',3''}$ 10.1, $J_{1'',2''}$ 3.9, H2"), 4.21 (1H, dd, $J_{2',3'}$ 9.6, $J_{1',2'}$ 8.1, H2'), 4.12 (1H, dd, $J_{3,4}$ 9.1, $J_{4,5}$ 9.1, H4), 4.14-4.07 (1H, m, H5"'), 4.02-3.94 (2H, m, H6', CH$_2$(CH$_2$)$_5$CH$_2$O), 3.90 (1H, dd, $J_{6,6}$ 11.5, $J_{5,6}$ 3.7, H6), 3.86 (1H, dd, $J_{2'',3''}$ 10.1, $J_{3'',4''}$ 2.6, H3"), 3.84 (1H, dd, $J_{2',3'}$ 9.4, $J_{3',4'}$ 3.8, H3'), 3.71-3.64 (3H, m, H4", H6, H6"), 3.59 (1H, ddd, J 9.5, J 6.8, J 6.8, CH=CH$_2$(CH$_2$)$_5$CH$_2$O), 3.50 (1H, dd, $J_{2,3}$ 9.0, $J_{3,4}$ 9.1, H3), 3.49 (1H, dd, $J_{2,3}$ 9.0, $J_{1,2}$ 8.0, H2), 3.20-3.14 (2H, m, H5, H5'), 3.04 (1H, dd, $J_{6''',6'''}$ 11.5, $J_{5''',6'''}$ 3.6, H6'''), 2.09, 1.97, 1.81, 1.46 (12H, 4×s, CH$_3$CO), 2.10-2.01 (2H, m, CH=CH$_2$(CH$_2$)$_5$CH$_2$O), 1.74-1.66 (2H, m, CH=CH$_2$(CH$_2$)$_5$CH$_2$O), 1.48-1.38 (6H, m, CH=CH$_2$(CH$_2$)$_5$CH$_2$O), 1.16 (3H, d, $J_{5''',6''}$ 6.6, H6"); $^{13}$C NMR (125 MHz): $\delta_C$ 170.4 (C=O), 170.3 (C=O), 170.1 (C=O), 170.0 (C=O), 139.4 (Ph), 139.0 (CH$_2$=CH), 138.6 (Ph), 138.52 (Ph), 138.50 (Ph), 138.4 (Ph), 138.3 (Ph), 137.7 (Ph), 129.1 (Ph), 129.0 (Ph), 128.42 (Ph), 128.36 (Ph), 128.32 (3C, Ph), 128.29 (Ph), 128.25 (Ph), 128.20 (Ph), 128.19 (Ph), 127.8 (Ph), 127.7 (Ph), 127.55 (Ph), 127.53 (Ph), 127.40 (2C, Ph), 127.36 (Ph), 127.3 (Ph), 126.4 (Ph), 126.3 (Ph), 114.3 (CH$_2$=CH), 103.8 (C1), 101.3, 100.8 (C1', PhCH), 98.3 (C1"), 92.1 (C1'''), 83.0, 71.7 (C2, C3), 79.9, 77.2, 76.5, 75.8, 75.5, 75.5, 71.3, 70.6 (C2', C2", C3', C3", C4, C4', C4", C5), 76.2 (PhCH$_2$), 75.3 (PhCH$_2$), 74.7 (PhCH$_2$), 7.36 (PhCH$_2$), 73.4 (PhCH$_2$), 72.1 (PhCH$_2$), 70.1 (CH=CH$_2$(CH$_2$)$_5$CH$_2$O), 69.0, 67.9 (C6, C6'), 68.8, 67.7, 67.4 (C3''', C4''', C5'''), 66.7, 66.4 (C5', C5"), 63.0 (C6'''), 46.5 (C2'''), 33.8 (CH=CH$_2$(CH$_2$)$_5$CH$_2$O), 29.8 (CH=CH$_2$(CH$_2$)$_5$CH$_2$O), 29.0 (CH=CH$_2$(CH$_2$)$_5$CH$_2$O), 28.9 (CH=CH$_2$(CH$_2$)$_5$CH$_2$O), 26.1 (CH=CH$_2$(CH$_2$)$_5$CH$_2$O), 22.6 (CH$_3$C=O), 20.69, (CH$_3$C=O), 20.66 (CH$_3$C=O), 20.6 (CH$_3$C=O), 16.7 (C6"). ESI MS: m/z calcd [C$_{89}$H$_{105}$NO$_{23}$]Na$^+$: 1578.6970. Found: 1578.6986.

Synthesis of 7-Octen-1-yl 4-O-[3-O-(2-N-Acetyl-2-deoxy-α-D-galactopyranosyl)-2-O-(α-L-fucopyranosyl)-β-D-galactopyranosyl]-β-D-glucopyranoside (VI-16)

A stirred solution of the tetrasaccharide VI-15 (240 mg, 0.154 mmol) in CH$_3$OH (25 mL) was treated with a catalytic amount of NaOCH$_3$ in CH$_3$OH and the solution was stirred (2 h). The solution was neutralized with Amberlite IR 120 (H$^+$), filtered and the residue subjected to flash chromatography (Iatrobeads, CH$_2$Cl$_2$/CH$_3$OH, 9:1) to afford the triol (210 mg, 95%) as a colourless oil. Redistilled liquid ammonia (20 mL) was collected in a flask cooled to −78° C. and treated with sodium until the blue colour persisted. A solution of the tetrasaccharide (90 mg, 0.063 mmol) in THF (4 mL) and CH$_3$OH (18 µL, 0.44 mmol) was added drop-wise and the solution was stirred (−78° C., 1 h). The reaction was then quenched by the addition of CH$_3$OH (4 mL) and the ammonia evaporated to dryness. The solution was taken up in CH$_3$OH (100 mL), neutralized with Amberlite IR 120 (H$^+$), filtered and the residue subjected to C-18 chromatography (CH$_3$OH/H$_2$O, 1:1) to afford the fully deprotected tetrasaccharide VI-16 (45.0 mg, 90%) as a colourless oil. [α]+17.1 (c=0.3, CH$_3$OH); $^1$H NMR (500 MHz, CD$_3$OD): $\delta_H$ 5.87-5.73 (1H, m, CH$_2$=CH), 5.34 (1H, d, $J_{1'',2''}$ 3.9, H1"), 5.16 (1H, d, $J_{1''',2'''}$ 3.9, H1'''), 5.01-4.95 (1H, m, CH=CH$_2$), 4.94-4.89 (1H, m, CH=CH$_2$), 4.52 (1H, d, $J_{1',2'}$ 7.8, H1'), 4.35-4.28 (2H, m, H2''', H5"), 4.26 (1H, d, $J_{1,2}$ 7.8, H1), 4.00 (1H, dd, $J_{2',3'}$ 9.7, $J_{1',2'}$ 7.8, H2'), 4.20-4.15, 4.13-4.09, 3.94-3.61, 3.57-3.50, 3.32-3.23 (21H, 5×m, H2, H2', H3', H3", H4, H4', H4", H4''', H5, H5', H5"', H6, H6', H6''', CH=CH$_2$(CH$_2$)$_5$CH$_2$O), 3.46 (1H, d, $J_{2,3}$ 9.1, $J_{3,4}$ 9.1, H3), 2.01 (3H, s, CH$_3$C=O), 2.09-1.98 (2H, m, CH=CH$_2$(CH$_2$)$_5$CH$_2$O), 1.65-1.58 (2H, m, CH=CH$_2$(CH$_2$)$_5$CH$_2$O), 1.44-1.30 (6H, m, CH=CH$_2$ (CH$_2$)$_5$CH$_2$O), 1.22 (3H, d, J$_{5',6'}$ 6.5, H6"); $^{13}$C NMR (125 MHz, CD$_3$OD): δ$_C$ 174.5 (C=O), 140.1 (CH$_2$=CH), 114.8 (CH$_2$=CH), 104.3 (C1), 102.2 (C1'), 100.2 (C1"), 93.6 (C1'''), 78.2, 78.0, 77.0, 76.8, 76.5, 74.9, 73.6, 73.5, 72.7, 71.9, 70.6, 70.0, 67.7, 64.9 (C2, C2', C2", C3, C3', C3", C3''', C4, C4', C4", C4''', C5, C5', C5"), 71.0 (CH=CH$_2$(CH$_2$)$_5$CH$_2$O), 69.9 (C5"), 63.4, 62.5, 61.7 (C6, C6', C6'''), 51.3 (C2'''), 34.8 (CH=CH$_2$(CH$_2$)$_5$CH$_2$O), 30.8 (CH=CH$_2$(CH$_2$)$_5$CH$_2$O), 30.08 (CH=CH$_2$(CH$_2$)$_5$CH$_2$O), 30.07 (CH=CH$_2$(CH$_2$)$_5$CH$_2$O), 27.0 (CH=CH$_2$(CH$_2$)$_5$CH$_2$O), 22.8 (CH$_3$C=O), 16.6 (C6"). ESI MS: m/z calcd [C$_{34}$H$_{59}$NO$_{20}$]Na$^+$: 824.3523. Found: 824.3526.

Example 5

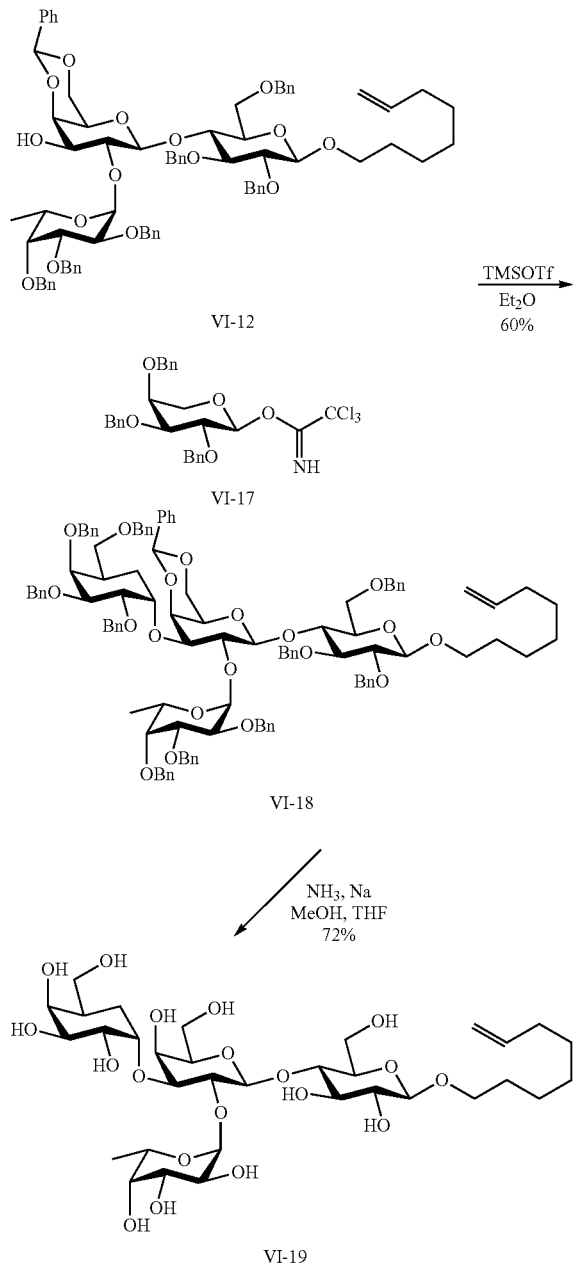

Synthesis of 7-Octen-1-yl 4-O-[4,6-O-Benzylidene-3-O-(2,3,4,6-tetra-O-benzyl-α-D-galactopyranosyl)-2-O-(2,3,4-tri-O-benzyl-α-L-fucopyranosyl)-β-D-galactopyranosyl]-2,3,6-tri-O-benzyl-β-D-glucopyranoside (VI-18)

A solution of the acceptor VI-12 (320 mg, 0.261 mmol) in dry Et$_2$O (5 mL) was treated with 4 Å molecular sieves and the mixture stirred (rt, 1 h). The mixture was then cooled (−10° C.), treated with TMSOTf (10 μL, 0.058 mmol); the trichloroacetimidate (Wegmann, B., Schmidt, R. R. *J. Carbohydr. Chem.*, 1987, 6:357-375) (VI-17) (700 mg, 1.02 mmol) in dry Et$_2$O (10 mL) was then added drop-wise and the mixture was allowed to stand (20 min). The mixture was neutralized with Et$_3$N (0.5 mL), filtered, concentrated and subjected to flash chromatography (EtOAc/hexanes, 1:4) to afford the partially pure tetrasaccharide VI-18 (270 mg, 60%) as a colourless oil.

Synthesis of 7-Octen-1-yl 4-O-[2-O-(α-L-Fucopyranosyl)-3-O-(α-D-galactopyranosyl)-β-D-galactopyranosyl]-β-D-glucopyranoside (VI-19)

Redistilled liquid ammonia (10 mL) was collected in a flask cooled to −78° C. and treated with sodium until the blue colour persisted. A solution of the tetrasaccharide VI-18 (160 mg, 0.091 mmol) in THF (4 mL) and CH$_3$OH (41 μL, 1.01 mmol) was added drop-wise and the solution stirred (−78° C., 1 h). The reaction was then quenched by the addition of CH$_3$OH (4 mL) and the ammonia evaporated to dryness. The solution was taken up in CH$_3$OH (100 mL), neutralized with Amberlite IR 120 (H$^+$), filtered and the residue subjected to chromatography (Iatrobeads, CH$_2$Cl$_2$/CH$_3$OH, 1:1) to afford the fully deprotected compound VI-19 (50 mg, 72%). [α]−3.0 (c=1.0, CH$_3$OH); $^1$H NMR (500 MHz, CD$_3$OD): δ$_H$ 5.86-5.76 (1H, m, CH$_2$=CH), 5.33 (1H, d, J$_{1',2'}$ 3.8, H1'), 5.17 (1H, d, J$_{1''',2'''}$ 3.7, H1"), 5.00-4.95 (1H, m, CH=CH$_2$), 4.93-4.89 (1H, m, CH=CH$_2$), 4.53 (1H, d, J$_{1',2'}$ 7.6, H1'), 4.29 (1H, q, J$_{5'',6''}$ 6.6, H5"), 4.28 (1H, d, J$_{1,2}$ 8.2, H1), 3.47 (1H, dd, J$_{2,3}$ 9,1, J$_{3,4}$ 9,1, H3), 4.19-4.10, 4.03-3.50, 3.31-3.24 (22H, 3×m, H2, H2', H2", H2''', H3', H3", H3''', H4, H4', H4", H4''', H5, H5', H5''', H6, H6', H6''', CH=CH$_2$(CH$_2$)$_5$CH$_2$O), 2.09-2.00 (2H, m, CH=CH$_2$(CH$_2$)$_5$CH$_2$O), 1.66-1.57 (2H, m, CH=CH$_2$(CH$_2$)$_5$CH$_2$O), 1.44-1.25 (6H, m, CH=CH$_2$(CH$_2$)$_5$CH$_2$O), 1.20 (3H, d, J$_{5'',6''}$ 6.6, H6"); $^{13}$C NMR (125 MHz, CD$_3$OD): δ$_C$ 140.1 (CH$_2$=CH), 114.8 (CH$_2$=CH), 104.3 (C1'), 102.2 (C1), 100.3 (C1"), 96.1 (C1'''), 79.8, 78.3, 77.0, 76.5, 76.4, 74.8, 73.7, 73.6, 73.1, 71.8, 71.4, 71.3, 71.0, 69.9, 67.7, 65.8 (C2, C2', C2", C2''', C3, C3', C3", C3''', C4, C4', C4", C4''', C5, C5', C5", C5'''), 71.0 (CH=CH$_2$(CH$_2$)$_5$CH$_2$O), 63.3, 62.5, 61.7 (C6, C6', C6'''), 34.8 (CH=CH$_2$(CH$_2$)$_5$CH$_2$O), 30.8 (2C, CH=CH$_2$(CH$_2$)$_5$CH$_2$O), 30.1 (CH=CH$_2$(CH$_2$)$_5$CH$_2$O), 27.0 (CH=CH$_2$(CH$_2$)$_5$CH$_2$O), 16.6 (C6"). ESI MS: m/z calcd [C$_{32}$H$_{56}$O$_{20}$]Na$^+$: 783.3257. Found: 783.3258.

Example 6

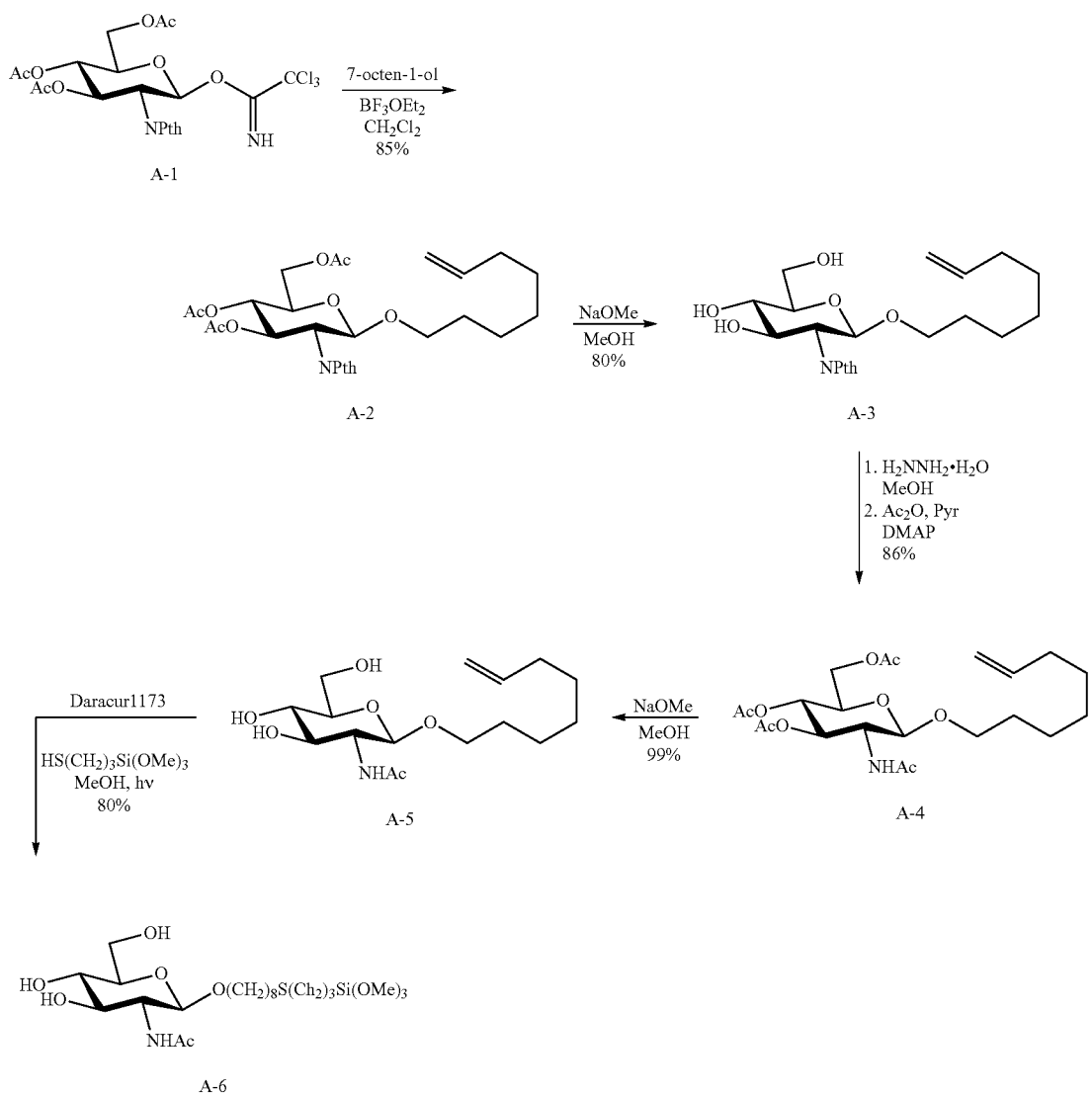

Synthesis of 3,4,6-Tri-O-acetyl-2-deoxy-2-pthalimido-β-D-glucopyranosyl Trichloroacetimidate (A-1)

Prepared by the method of Schmidt and co-workers with the $^1$H and $^{13}$C nmr spectra in good agreement with that reported. (Grundler, G., Schmidt, R. R. *Carbohydr. Res.,* 1985, 135:203-218).

Synthesis of 7-Octen-1-yl 3,4,6-tri-O-acetyl-2-deoxy-2-pthalimido-β-D-glucopyranoside (A-2)

A solution of the trichloroacetimidate A-1 (8.10 g, 14.0 mmol) and 7-octen-1-ol (2.24 g, 17.5 mmol) in dry $CH_2Cl_2$ (40 mL) was stirred with 4 Å molecular sieves (2.5 g, 30 min). The mixture was then cooled (−15° C.) and treated with $BF_3 \cdot OEt_2$ (200 μL) and allowed to warm slowly to 0° C. Treatment with $Et_3N$ (1 mL) followed by filtration, concentration and flash chromatography (EtOAc/Petrol, 1:1) gave the octenyl glycoside A-2 as a colourless oil (6.56 g, 85%).

[α]+17.7 (c=1.5, $CH_2Cl_2$); $R_f$ 0.48 (EtOAc/petrol, 7:3); $^1$H NMR (500 MHz): $\delta_H$ 7.87-7.81 (2H, m, Ar), 7.75-7.69 (2H, m, Ar), 5.79 (1H, dd, $J_{2,3}$ 10.8, $J_{3,4}$ 9.1, H3), 5.73-5.55 (1H, m, CH=$CH_2$), 5.34 (1H, d, $J_{1,2}$ 8.5, H1), 5.16 (1H, dd, $J_{4,5}$ 10.1, $J_{3,4}$ 9.1, H4), 4.94-4.84 (2H, m, CH=$CH_2$), 4.39-4.26 (2H, m, H2, H6), 4.23-4.01 (1H, m, 116), 3.95-3.79 (2H, m, H5, CH=$CH_2(CH_2)_5CH_2O$), 3.51-3.32 (1H, m, CH=$CH_2$ $(CH_2)_5CH_2O$), 2.12 (3H, s, $CH_3C$=O), 2.03 (3H, s, $CH_3C$=O), 1.88 (3H, s, $CH_3C$=O), 1.91-1.76 (m, 2H, CH=$CH_2(CH_2)_5CH_2O$), 1.51-1.25 (m, 2H, CH=$CH_2$ $(CH_2)_5CH_2O$), 1.17-0.93 (m, 6H, CH=$CH_2(CH_2)_5CH_2O$); $^{13}$C NMR (125 MHz): $\delta_C$ 170.7 (C=O), 170.2 (C=O), 169.5 (C=O), 138.9 (CH=$CH_2$), 134.3 (Ph), 131.4 (Ph), 123.6 (Ph), 114.1 (CH=$CH_2$), 98.2 (C1), 70.8 (CH=$CH_2$ $(CH_2)_5CH_2O$), 71.8, 70.1, 69.1 (C3, C4, C5), 62.1 (C6), 54.7 (C2), 33.5 (CH=$CH_2(CH_2)_5CH_2O$), 29.1 (CH=$CH_2(CH_2)_5$ $CH_2O$), 28.61 (CH=$CH_2(CH_2)_5CH_2O$), 28.58 (CH=$CH_2$ $(CH_2)_5CH_2O$), 25.6 (CH=$CH_2(CH_2)_5CH_2O$), 20.8 ($CH_3CO$), 20.6 ($CH_3CO$), 20.5 ($CH_3CO$). ESI MS: m/z calcd [$C_{28}H_{35}NO_{10}$]Na$^+$: 568.2153. Found 568.2155.

Synthesis of 7-Octen-1-yl 2-deoxy-2-pthalimido-β-D-glucopyranoside (A-3)

A solution of the triacetate A-2 (6.36 g, 11.7 mmol) in MeOH (80 mL) was treated with a catalytic amount of NaOMe in MeOH and the solution stirred (30 min). The NaOMe was then neutralized with Amberlite IR120 and the mixture filtered; concentration followed by flash chromatography (EtOAc/Petrol, 9:1) afforded the triol A-3 as a white solid (3.89 g, 80%). A small portion was recrystallized ($CH_2Cl_2$/hexane) for analysis. Mp 127-129° C. [α]–15.3 (c=1.0, $CH_2Cl_2$); $R_f$ 0.13 (EtOAc/petrol, 7:3); $^1$H NMR (500 MHz): $\delta_H$ 7.82-7.76 (2H, m, Ar), 7.72-7.65 (2H, m, Ar), 5.71-5.61 (1H, m, CH=$CH_2$), 5.16 (1H, d, $J_{1,2}$ 8.5, H1), 4.92-4.83 (2H, m, CH=$CH_2$), 4.57 (1H, d, J 4.65, OH), 4.32-4.23 (1H, m, H3), 4.21 (1H, d, J 6.3, OH), 4.06 (1H, dd, $J_{2,3}$ 10.8, $J_{1,2}$ 8.5, H2), 3.93-3.83 (2H, m, H6), 3.80-3.64 (2H, m, H4, CH=$CH_2(CH_2)_5CH_2O$), 3.50-3.33 (3H, m, H5, CH—$CH_2(CH_2)_5CH_2O$, OH), 1.87-1.73 (2H, m, CH=$CH_2$ $(CH_2)_5CH_2O$), 1.42-1.24 (2H, m, CH=$CH_2(CH_2)_5CH_2O$), 1.08-0.91 (6H, m, CH=$CH_2(CH_2)_5CH_2O$); $^{13}$C NMR (125 MHz): $\delta_C$ 168.4 (C=O), 139.0 (CH=$CH_2$), 134.0 (Ph), 131.7 (Ph), 123.4 (Ph), 114.1 (CH=$CH_2$), 98.4 (C1), 75.5 (C5), 71.6 (C3), 71.3 (C4), 69.9 (CH=$CH_2(CH_2)_5CH_2O$), 61.7 (C6), 56.8 (C2), 33.5 (CH=$CH_2(CH_2)_5CH_2O$), 29.2 (CH=$CH_2(CH_2)_5CH_2O$), 28.6 (2C, CH=$CH_2(CH_2)_5CH_2O$), 25.6 (CH=$CH_2(CH_2)_5CH_2O$). ESI MS: m/z calcd [$C_{22}H29NO_7$]Na$^+$: 442.1836. Found 442.1838.

Synthesis of 7-Octen-1-yl 3,4,6-tri-O-Acetyl-2-N-acetyl-2-deoxy-β-D-glucopyranoside (A-4)

A solution of the triol A-3 (129 mg, 0.31 mmol) in MeOH (0.5 mL) was treated with a solution of hydrazine hydrate (100 mg, 2 mmol) in MeOH (2 mL) and the solution refluxed (4 h). The solution was concentrated and the residue treated with pyridine (2 mL), $Ac_2O$ (1 mL) and DMAP (5 mg). After 1 hour the solution was treated with MeOH (2 mL), concentrated and the residue taken up in EtOAc; this was then washed with 1M HCl, $H_2O$, saturated $NaHCO_3$, and brine. The organic extract was then dried, concentrated and subjected to flash chromatography (EtOAc/Petrol, 3:1) to afford A-4 as a colourless oil (122 mg, 86%). [α]–17.6 (c=0.4, $CH_2Cl_2$); $R_f$ 0.45 (EtOAc/petrol, 3:1); $^1$H NMR (500 MHz): $\delta_H$ 5.84-5.74 (1H, m, CH=$CH_2$), 5.57 (1H, d, J 8.7, NH), 5.30 (1H, dd, $J_{2,3}$ 10.6, $J_{3,4}$ 9.6, H3), 5.05 (1H, dd, $J_{3,4}$ 9.6, $J_{4,5}$ 9.6, H4), 5.00-4.95 (1H, m, CH=$CH_2$), 4.94-4.90 (1H, m, CH=$CH_2$), 4.68 (1H, d, $J_{1,2}$ 8.3, H1), 4.34-4.20 (1H, m, H6), 4.18-4.04 (1H, m, H6), 3.94-3.75 (2H, m, H2, CH=$CH_2$ $(CH_2)_5CH_2O$,), 3.72-3.66 (1H, m, H5), 3.50-3.41 (1H, m, CH=$CH_2(CH_2)_5CH_2O$,), 2.07 (3H, s, $CH_3CO$), 2.02 (3H, s, $CH_3CO$), 2.01 (3H, s, $CH_3CO$), 1.93 (3H, s, $CH_3CO$), 2.02-1.97 (2H, m, CH=$CH_2(CH_2)_5CH_2O$), 1.63-1.48 (2H, m, CH=$CH_2(CH_2)_5CH_2O$), 1.40-1.20 (6H, m, CH=$CH_2$ $(CH_2)_5CH_2O$). $^{13}$C NMR (125 MHz): $\delta_C$ 170.8 (C=O), 170.7 (C=O), 170.1 (C=O), 169.4 (C=O), 139.0 (CH=$CH_2$), 114.3 (CH=$CH_2$), 100.7 (C1), 72.4, 71.8 (C3, C5), 69.9 (CH=$CH_2(CH_2)_5CH_2O$), 68.8 (C4), 62.2 (C6), 54.9 (C2), 33.7 (CH=$CH_2(CH_2)_5CH_2O$), 29.4 (CH=$CH_2$ $(CH_2)_5CH_2O$), 28.83 (CH=$CH_2(CH_2)_5CH_2O$), 28.77 (CH=$CH_2(CH_2)_5CH_2O$), 25.70 (CH=$CH_2(CH_2)_5CH_2O$), 23.3 ($CH_3CO$), 20.73 ($CH_3CO$), 20.69 ($CH_3CO$), 20.6 ($CH_3CO$). ESI MS: m/z calcd [$C_{22}H_{35}NO_9$]Na$^+$: 480.2204. Found 480.2208.

Synthesis of 7-Octen-1-yl 2-N-Acetyl-2-deoxy-β-D-glucopyranoside (A-5)

A solution of A-4 (105 mg, 23.0 mmol) in MeOH (1 mL) was treated with a catalytic amount of NaOMe in MeOH and the solution allowed to stand (1 h). The solution was neutralized with Amberlite IR 120 (H$^+$), filtered and the residue subjected to flash chromatography ($CH_2Cl_2$/MeOH, 4:1) to give the triol A-5 as a colourless glass (72 mg, 99%). [α]–23.7 (c=0.6, MeOH); $R_f$ 0.12 ($CH_2Cl_2$/MeOH, 9:1); $^1$H NMR (500 MHz, $CD_3OD$): $\delta_H$ 5.87-5.74 (1H, m, CH=$CH_2$), 5.01-4.86 (2H, m, CH=$CH_2$), 4.38 (1H, d, $J_{1,2}$ 8.4, H1), 3.90-3.83 (2H, m, H6, CH=$CH_2(CH_2)_5CH_2O$,), 3.67 (1H, dd, $J_{6,6}$ 11.9, $J_{5,6}$ 5.7, H6), 3.62 (dd, $J_{2,3}$ 10.3, $J_{1,2}$ 8.4, H2), 3.48-3.41 (2H, m, H3, CH=$CH_2(CH_2)_5CH_2O$,), 3.37-3.27 (1H, m, H4) 3.27-3.21 (1H, m, H5), 1.96 (3H, s, $CH_3CO$), 1.96 (3H, s, $CH_3CO$), 2.07-2.00 (2H, m, CH=$CH_2(CH_2)_5CH_2O$), 1.63-1.44 (2H, m, CH=$CH_2(CH_2)_5CH_2O$), 1.46-1.22 (6H, m, CH=$CH_2$ $(CH_2)_5CH_2O$). $^{13}$C NMR (125 MHz): $\delta_C$ 173.6 (C=O), 140.1 (CH=$CH_2$), 114.8 (CH=$CH_2$), 102.8 (C1), 78.0 (C5), 76.1 (C3), 72.2 (C4), 70.6 (CH=$CH_2(CH_2)_5CH_2O$), 62.8 (C6), 57.5 (C2), 34.8 (CH=$CH_2(CH_2)_5CH_2O$), 30.6 (CH=$CH_2(CH_2)_5CH_2O$), 30.1 (CH=$CH_2(CH_2)_5CH_2O$), 30.0 (CH=$CH_2(CH_2)_5CH_2O$), 27.0 (CH=$CH_2(CH_2)_5$ $CH_2O$), 23.1 ($CH_3CO$). ESI MS: m/z calcd [$C_{16}H_{29}NO_6$]Na$^+$: 354.1887. Found 354.1888.

Synthesis of 8-(3-(trimethoxysilyl)propylthio)octan-1-yl 2-N-Acetyl-2-deoxy-β-D-glucopyranoside (A-6)

A degassed solution of the alkene A-5 (32.0 mg, 0.097 mmol) in dry MeOH (0.4 mL) was treated with MPTMS (56.8 mg, 0.29 mmol), DAROCUR 1173 (5 µL) and the solution irradiated at 254 nm and 1200 W (16×75 W lamps) for 30 min. The solution was then diluted with dry MeOH (2 mL) and washed with hexanes (3×2 mL). The solution was then concentrated to afford A-6 (40 mg, 80%) as a somewhat unstable colourless oil. $^1$H NMR (500 MHz, $CD_3OD$): $\delta_H$ 4.38 (1H, d, $J_{1,2}$ 8.5, H1), 3.90-3.82 (2H, m, H6, $(CH_2)_7CH_2O$,), 3.67 (1H, dd, $J_{6,6}$ 11.8, $J_{5,6}$ 5.7, H6), 3.61 (1H, dd, $J_{1,2}$ 8.5, $J_{2,3}$ 8.5, H2), 3.55 (6H, s, $(CH_3O)_3Si$), 3.48-3.41 (2H, m, H3, $(CH_2)$ $7CH_2O$,), 3.34-3.28 (1H, m, H4), 3.27-3.22 (1H, m, H5), 2.54-2.46 (4H, m, $CH_2SCH_2(CH_2)_6CH_2O$), 1.97 (3H, s, $CH_3CO$), 1.81-1.63 (2H, m, $CH_2SCH_2(CH_2)_6CH_2O$), 1.61-1.50 (4H, m, $CH_2SCH_2(CH_2)_6CH_2O$, $(CH_3O)_3$ $SiCH_2CH_2CH_2SCH_2(CH_2)_6CH_2O$), 1.42-1.26 (8H, m, $CH_2SCH_2(CH_2)_6CH_2O$), 0.78-0.71 (2H, m, $(CH_3O)_3$ $SiCH_2CH_2CH_2SCH_2(CH_2)_6CH_2O$) $^{13}$C NMR (125 MHz, $CD_3OD$): $\delta_C$ 170.9 (C=O), 100.0 (C1), 75.2, 73.4 (C3, C4), 69.5 (C5), 67.8 ($(CH_2)_7CH_2O$), 60.1 (C6), 64.7 (C2), 46.1 (($CH_3O)_3Si$), 33.0 ($CH_2$), 30.0 ($CH_2$), 28.1 ($CH_2$), 28.0 ($CH_2$), 27.9 ($CH_2$), 27.70 ($CH_2$), 27.66 ($CH_2$), 27.1 ($CH_2$), 24.4 ($CH_2$), 20.3 ($CH_3C0$), 6.5 (($CH_3O)_3SiCH_2$). ESI MS: m/z calcd [$C_{22}H_{45}NO_9SiS$]Na$^+$: 550.2476. Found 550.2473.

Example 7

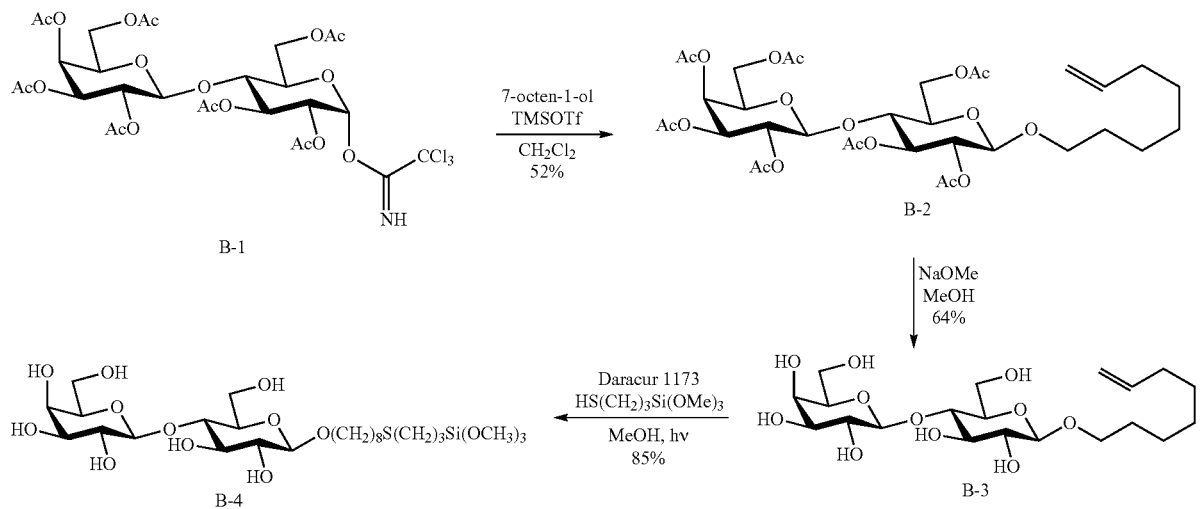

Synthesis of 7-octen-1-yl 4-O-(β-D-galactopyranose)-β-D-glucopyranoside (B-3)

A solution of the trichloroacetimidate (Amvam-Zollo, P. H., Sinaÿ, P. *Carbohydr. Res.*, 1986, 150:199-212) (B-1) (11.0 g, 14.1 mmol) in dry $CH_2Cl_2$ (200 mL) was treated with 7-octen-1-ol (2.53 mL, 16.9 mmol) and 4 Å molecular sieves (4.0 g) and the mixture stirred (rt, 1 h). The mixture was then cooled (−40° C.), treated with TMSOTf (200 μL) and allowed to stand (30 min). The mixture was treated with $Et_3N$ (3 mL), filtered, concentrated and the residue subjected to flash chromatography (EtOAc/Petrol, 1:1) to afford the somewhat pure glycoside (B-2) as a colorless oil (5.5 g, 52%). The residue was taken up in MeOH (150 mL) and treated with a catalytic amount of NaOMe in MeOH (rt, 1 h). The solution was neutralized with Amberlite IR120, filtered, concentrated and the residue subjected to flash chromatography ($CH_2Cl_2$/MeOH, 4:1) to afford the octenyl glycoside (B-3) as a colourless oil (2.1 g, 64%). $[\alpha]$−9.0 (c=0.5, MeOH); $R_f$ 0.15 ($CH_2Cl_2$/MeOH, 6:1); $^1H$ NMR (500 MHz, $CD_3OD$): $\delta_H$ 5.85-5.75 (1H, m, CH=$CH_2$), 5.00-4.94 (1H, m, CH=$CH_2$), 4.92-4.88 (1H, m, CH=$CH_2$), 4.35 (1H, d, $J_{1',2'}$ 7.6, H1''), 4.27 (1H, d, $J_{1,2}$ 7.6, H1), 3.91-3.74, 3.71-3.67, 3.59-3.46, 3.41-3.36 (13H, 4×m, H2', H3, H3', H4, H4'', H5, H5'', H6, H6', CH=$CH_2(CH_2)_5CH_2O$,), 3.23 (1H, dd, $J_{2,3}$ 9.0, $J_{1,2}$ 7.6, H²), 2.08-2.01 (2H, m, CH=$CH_2(CH_2)_5CH_2O$), 1.65-1.57 (2H, m, CH=$CH_2(CH_2)_5CH_2O$), 1.43-1.29 (6H, m, CH=$CH_2(CH_2)_5CH_2O$). $^{13}C$ NMR (125 MHz, $CD_3OD$): $\delta_C$ 140.1 (CH=$CH_2$), 114.7 (CH=$CH_2$), 105.1, 104.2 (C1, C1') 80.7, 77.1, 76.5, 76.4, 74.9, 74.8, 72.6, 70.3 (C2, C2', C3, C3', C4, C4', C5, C5'), 70.9 (CH=$CH_2(CH_2)_5CH_2O$), 62.5, 62.0 (C6, C6'), 34.8 (CH=$CH_2(CH_2)_5CH_2O$), 30.7 (CH=$CH_2(CH_2)_5CH_2O$), 30.08 (CH=$CH_2(CH_2)_5CH_2O$), 30.06 (CH=$CH_2(CH_2)_5CH_2O$), 26.9 (CH=$CH_2(CH_2)_5CH_2O$). ESI MS: m/z calcd $[C_{20}H_{36}O_{11}]Na^+$: 475.2150. Found 475.2142.

Synthesis of 8-(3-(trimethoxysilyl)propylthio)octan-1-yl 4-O-(β-D-galactopyranose)-β-D-glucopyranoside (B-4)

A degassed solution of the alkene (B-3) (19 mg, 0.042 mmol) in dry MeOH (0.4 mL) was treated with MPTMS (24 mg, 0.13 mmol), DAROCUR 1173 (5 μL) and the solution irradiated at 254 nm and 1200 W (16×75 W lamps) for 30 min. The solution was then diluted with dry MeOH (2 mL) and washed with hexanes (3×2 mL). The solution was then concentrated to afford B-4 (23 mg, 85%) as a somewhat unstable colourless oil. $^1H$ NMR (500 MHz, $CD_3OD$): $\delta_H$ 4.35 (1H, d, $J_{1',2'}$ 7.6, H1'), 4.27 (1H, d, $J_{1,2}$ 7.8, H1), 3.91-3.67, 3.61-3.45, 3.41-3.28 (22H, 3×m, H2', H3, H3', H4, H4', H5, H5', H6, H6', $(CH_2)_7CH_2O$, $(CH_3O)_3Si$), 3.23 (1H, dd, $J_{2,3}$ 8.4, $J_{1,2}$ 7.8, H2), 2.55-2.45 (4H, m, $CH_2SCH_2(CH_2)_6CH_2O$), 1.73-1.51 (6H, m, $CH_2SCH_2(CH_2)_6CH_2O$, $(CH_3O)_3SiCH_2CH_2CH_2SCH_2(CH_2)_6CH_2O$), 1.44-1.29 (8H, m, $CH_2SCH_2(CH_2)_6CH_2O$), 0.80-0.68 (2H, m, $(CH_3O)_3SiCH_2CH_2CH_2SCH_2(CH_2)_6CH_2O$) $^{13}C$ NMR (125 MHz, $CD_3OD$): $\delta_C$ 105.1, 104.2 (C1, C1'), 80.7, 77.1, 76.5, 76.4, 74.85, 74.78, 72.6, 70.3 (C2, C2', C3, C3', C4, C4', C5, C5'), 70.9 ($(CH_2)_7CH_2O$), 62.5, 62.0 (C6, C6'), 50.9 ($(CH_3O)_3Si$), 35.8 ($CH_2$), 32.7 ($CH_2$), 30.85 ($CH_2$), 30.77 ($CH_2$), 30.5 ($CH_2$), 30.3 ($CH_2$), 29.9 ($CH_2$), 27.1 ($CH_2$), 24.1 ($CH_2$), 9.2 ($(CH_3O)_3SiCH_2$).

Example 8

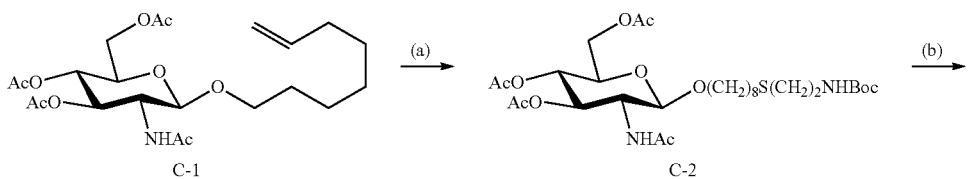

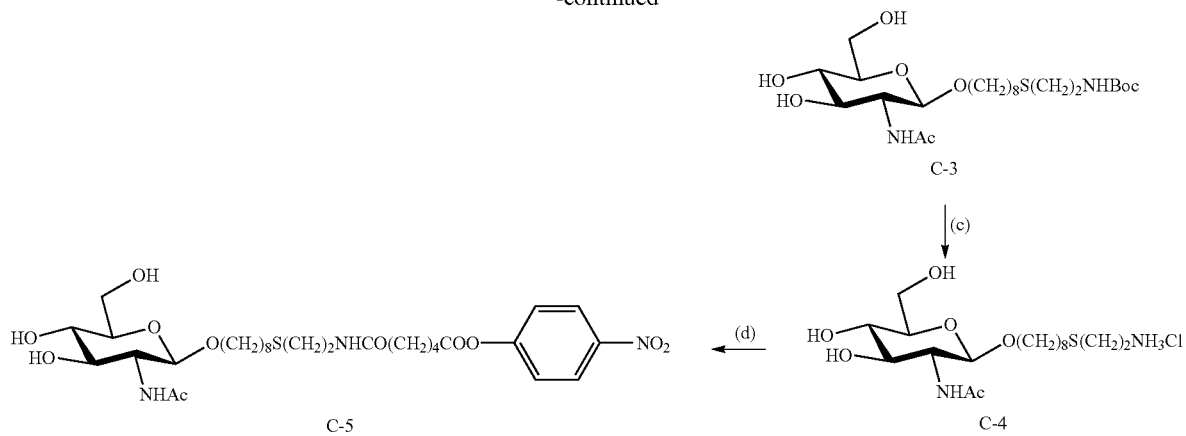

Synthesis of 8-(2-(tert-butylcarbamate)ethylthio) octan-1yl 3,4,6-tri-O-acetyl-2-N-acetyl-2-deoxy-β-D-glucopyranoside (C-2)

A solution of the alkene C-1 (1.11 g, 2.43 mmol) and cysteamine hydrochloride (1.37 g, 12.1 mmol) in degassed MeOH (3 mL) was irradiated at 254 nm (1 h). The solution was then concentrated and then taken up in $(CH_3)_2CO/H_2O$ (7/3, 70 mL) and then treated with $NaHCO_3$ (12.2 g, 0.145 mol) and $Boc_2O$ (9.50 g, 43.6 mmol) and the mixture stirred (r.t., 12 h). The mixture was then filtered, concentrated somewhat and then partitioned between EtOAc (250 mL) and saturated NaCl solution (200 mL). The organic layer was dried, concentrated and subjected to flash chromatography (EtOAc/Petrol, 3:1) to give the carbamate C-2 as a colourless oil (1.50 g, 97%). [α]–8.5 (c=0.9, $CH_2Cl_2$); $R_f$ 0.28 (EtOAc/petrol, 7:3); NMR (500 MHz): 5.90-5.78 (1H, m, NH), 5.28 (1H, dd, $J_{2,3}$ 10.3, $J_{3,4}$ 9.6, H3), 5.02 (1H, dd, $J_{3,4}$ 9.6, $J_{4,5}$ 9.6, H4), 4.67 (1H, d, $J_{1,2}$ 8.3, H1), 4.23 (1H, dd, $J_{6,6}$ 12.2, $J_{5,6}$ 4.8, H6), 4.10 (1H, dd, $J_{6,5}$ 12.2, $J_{5,6}$ 2.3, H6), 3.85-3.75 (2H, m, H2, $CH_2O$,), 3.68 (1H, ddd, $J_{4,5}$ 9.6, $J_{5,6}$ 4.8, 2.3, H5), 3.49-3.40 (m, 1H, $CH_2O$,), 3.30-3.23 (2H, m, $CH_2N$), 2.62-2.57 (2H, m, $CH_2S$), 2.50-2.45 (2H, m, $CH_2S$), 2.05 (3H, s, $CH_3C=O$), 2.00 (3H, s, $CH_3C=O$), 1.99 (3H, s, $CH_3C=O$), 1.91 (3H, s, $CH_3C=O$), 1.59-1.18 (21H, m, $(CH_2)_6CH_2O$, $(CH_3)_3C$)). $^{13}C$ NMR (125 MHz): $δ_C$ 170.8 (C=O), 170.7 (C=O), 170.1 (C=O), 169.4 (C=O), 155.8 (C=O), 100.7 (C1), 72.4 (C3), 71.7 (C5), 69.8 ($CH_2O$), 68.8 (C4), 62.2 (C6), 54.8 (C2), 39.7 ($CH_2N$), 32.2 ($CH_2S$), 31.8 ($CH_2S$), 29.6 (($CH_2)_6CH_2O$), 29.4 (($CH_2)_6CH_2O$), 29.2 (($CH_2)_6CH_2O$), 29.12 (($CH_2)_6CH_2O$), 29.06 (($CH_2)_6CH_2O$), 28.7 (($CH_2)_6CH_2O$), 28.4 (($CH_3)_3C$), 25.7 (($CH_3)_3C$), 23.3 ($CH_3C=O$), 20.73 ($CH_3C=O$), 20.68 ($CH_3C=O$), 20.6 ($CH_3C=O$). ESI MS: m/z calcd $[C_{29}H_{50}N_2O_{11}S]Na^+$: 657.3027. Found 657.3021.

Synthesis of 8-(2-(tert-butylcarbamate)ethylthio) octan-1yl 2-N-acetyl-2-deoxy-β-D-glucopyranoside (C-3)

A solution of the carbamate C-2 (1.44 g, 1.56 mmol) in MeOH (1 mL) was treated with a catalytic amount of NaOMe in MeOH and the solution allowed to stand (1 h). The solution was neutralized with Amberlite IR 120 ($H^+$), filtered and the residue subjected to flash chromatography ($CH_2Cl_2$/MeOH, 4:1) to give the triol C-3 as a colourless glass (917 mg, 80%). [α]–13.8 (c=0.3, MeOH); $R_f$ 0.12 ($CH_2Cl_2$/MeOH, 9:1); $^1H$ NMR (500 MHz, $CD_3OD$): 4.38 (1H, d, $J_{1,2}$ 8.4, H1), 3.90-3.84 (2H, m, H6, $CH_2O$), 3.67 (1H, dd, $J_{6,6}$ 10.3, $J_{5,6}$ 5.7, H6), 3.61 (1H, dd, $J_{2,3}$ 10.3, $J_{1,2}$ 8.4, H2), 3.48-3.41 (2H, m, H3, $CH_2O$), 3.36-3.15 (4H, m, H4, H5, $CH_2N$), 2.60-2.47 (4H, m, $CH_2S$), 1.96 (3H, s, $CH_3C=O$), 1.62-1.25 (21H, m, $(CH_2)_6CH_2O$, $(CH_3)_3C$). $^{13}C$ NMR (125 MHz): $δ_C$ 170.6 (C=O), 155.9 (C=O), 102.1 (C1), 77.4 (C5), 75.5 ($C^3$), 71.6 (C4), 70.0 ($CH_2O$), 62.3 (C6), 56.9 (C2), 32.2 ($CH_2S$), 32.1 ($CH_2S$), 30.3 (($CH_2)_6CH_2O$), 30.1 (($CH_2)_6CH_2O$), 29.9 (($CH_2)_6CH_2O$), 29.80 (($CH_2)_6CH_2O$), 29.77 (($CH_2)_6CH_2O$), 29.3 (($CH_2)_6CH_2O$), 28.2 (($CH_3)_3C$), 26.5 (($CH_3)_3C$), 22.5 ($CH_3C=O$). ESI MS: m/z calcd $[C_{23}H_4N_2O_8S]Na^+$: 531.2711. Found 531.271.

Synthesis of Half Ester (C-5)

A solution of the carbamate C-3 (170 mg, 0.33 mmol) in MeOH (3 mL) was treated with HCl (1M, 1 mL) and the solution stirred (rt, 60 min). The solution was concentrated to give a white solid that was taken up in DMF (15 mL) and treated with p-nitro phenyl ester linker (Wu, X., Ling, C. C., Bundle, D. R. *Org. Lett.*, 2004, 6:4407-4410) C-6 (580 mg, 1.50 mmol) and stirred (rt, 12 h). The solution was concentrated and subjected to flash chromatography ($CH_2Cl_2$/MeOH, 4:1) to give the somewhat unstable ester C-5 as a pale yellow solid (145 mg, 65%). $R_f$ 0.85 ($CH_2Cl_2$/MeOH, 9:1); $^1H$ NMR (500 MHz, $CD_3OD$): $δ_H$ 8.31-8.24 (2H, m, Ph), 7.38-7.34 (2H, m, Ph), 4.40 (1H, d, $J_{1,2}$ 8.4, H1), 3.90-3.83 (2H, m, H6, $CH_2O$), 3.71-3.59 (2H, m, H2, H6), 3.48-3.40 (m, 2H, H3, $CH_2O$), 3.38-3.22 (4H, m, $CH_2N$, H4, H5), 2.69-2.59, 2.55-2.50, 2.31-2.22 (8H, 3×m, $CH_2S$, $CH_2C=O$), 1.97 (3H, s, $CH_3C=O$), 1.80-1.23 (16H, m, $CH_2$). $^{13}C$ NMR (125 MHz): $δ_C$ 176.6 (C=O), 174.5 (C=O), 173.5 (C=O), 158.0 (Ph), 147.6 (Ph), 127.0 (Ph), 124.9 (Ph), 103.6 (C1), 78.8, 77.0, 73.1 (C3, C4, C5), 71.5 ($CH_2O$), 63.7 (C6), 53.3 (C2), 41.1 ($CH_2$), 37.5 ($CH_2$), 35.5 ($CH_2$), 33.6 ($CH_2$), 33.1 ($CH_2$), 31.6 ($CH_2$), 31.5 ($CH_2$), 31.3 ($CH_2$), 31.2 ($CH_2$), 30.7 ($CH_2$), 28.0 ($CH_2$), 27.1 ($CH_2$), 26.2 ($CH_2$), 24.0 ($CH_3C=O$). ESI MS: m/z calcd $[C23H47N_3O_{11}S]Na^+$: 680.2823. Found 680.2825.

Example 9

Preparation of Silica and Alumina Coated Stainless Steel Surfaces

Preparation of Silica Coated Stainless Steel Surfaces Using TEOS Dip

Stainless Steel Stent Surface Preparation $SiO_2$-coated stainless steel stents were prepared according to a variation of prior art procedures (Meth, S., Sukenik, C. N. *Thin Solid Films*, 2003, 425(1-2):49-58; Shapiro, L., Marx, S., Mandler, D. *Thin Solid Films*, 2007, 515:4624-4628). The stainless steel stent was sonicated for 10 minutes each in four solvents (18 M$\Omega$ $H_2O$, $CH_2Cl_2$, $(CH_3)_2CO$, EtOH). Subsequently, the stainless steel stent was treated with air plasma for 90 minutes (~800 mTorr). Upon removal from the plasma cleaner, the stainless steel stent was immediately submerged in neat tetraethoxysilane (TEOS). After 15-30 seconds, the stent was removed, and submerged in 18 M$\Omega$ $H_2O$ for 2 minutes. The stent was dried under a stream of nitrogen before being resubmerged in neat TEOS or in an ethanol solution of TEOS with varying pH. In between dip cycles, a curing step consisting of 15 minutes at 110° C. was sometimes applied. This cycle was typically repeated 5-10 times. Upon completion of the cycles, the stainless steel foil was left sitting in 18 M$\Omega$ $H_2O$ for 1 hour. Upon removal from water, the $SiO_2$-coated stent was immediately functionalized. The electroactive area of the stainless steel surface was obtained and is shown in Table 2. The infrared stretching frequencies of the stainless steel surface were also calculated and are shown in Table 3. The surfaces were further characterized using SEM and AES and the results shown in FIG. 10A, FIG. 10B, FIG. 11A and FIG. 11B.

TABLE 2

The average electroactive area (Ea A) obtained by cyclic voltammetry and the composition of metals derived from the stainless steel (Fe, Cr, Ni, and Mo) obtained by XPS of silica coated stainless steel

| Sample | Average % Ea A | % Metals |
|---|---|---|
| Clean SS | 61.6 (3.4) | 12 |
| TEOS dip | 64.9 (3.0) | 7 |
| Heat Cure 100% TEOS | 72.3 (5.4) | 7 |
| Heat Cure 50% TEOS, 50% EtOH | 41.9 (1.5) | 5 |
| Heat Cure 50% TEOS, 50% EtOH (95%) | 44.5 (3.4) | 7 |
| Heat Cure 50% TEOS, 50% Acidic EtOH | 49.0 (3.9) | 6 |
| Sol gel | 45.2 (1.1) | 0.2 |

TABLE 3

Infrared Stretching Frequencies found in stainless steel 316L coated with silica

| Frequency (cm$^{-1}$) | Assignment |
|---|---|
| ~3750 | SiO—H stretch |
| 1190 | Si—O asymmetric stretch |
| 1140 | Si—O—Si asymmetric stretch |
| 1090 | Si—O—Si asymmetric stretch |

Preparation of Silica-Coated Stainless Steel Surfaces Using ALD

Figure 13:
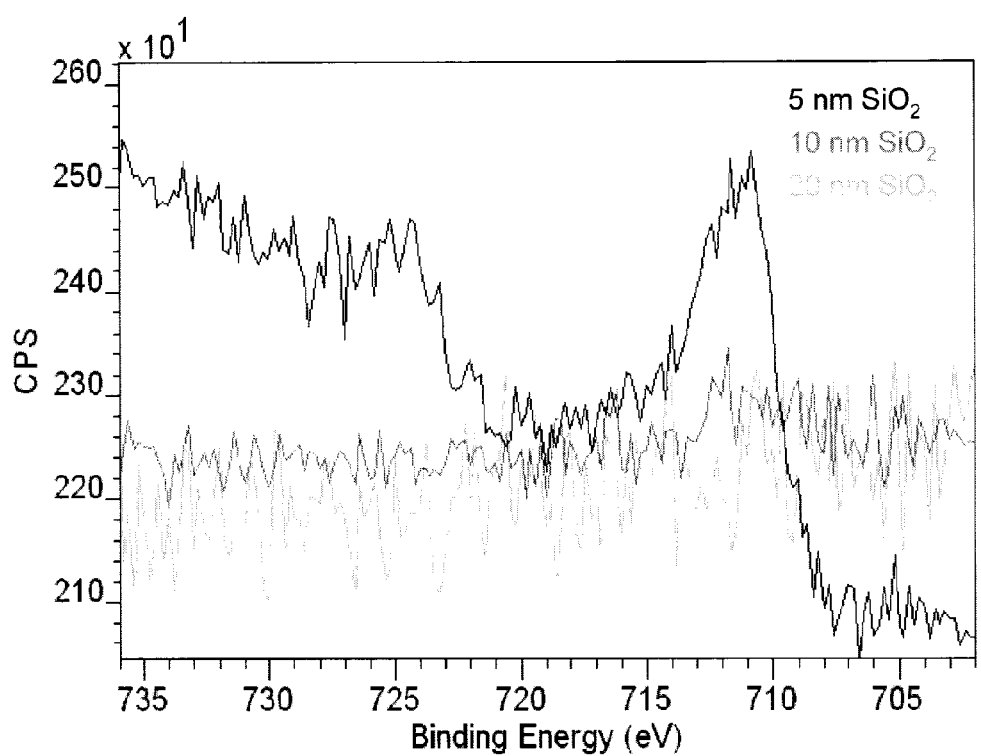
FIG. 13 is a high resolution X-ray photoelectron spectra of the Fe 2p peak from three atomic layer deposited (ALD) silica coated 316L stainless steel plates that can be used in one embodiment of the present invention. Each sample has a silica coating that was deposited via atomic layer deposition (ALD). As the thickness of the silica layer grows, the Fe 2p orbital peak signal disappears in the ~10 nm $SiO_2$ coating sample, illustrating that the surface is uniformly coated in $SiO_2$, and the layer is as thick as the penetration depth of the X-ray beam of the instrument.

Freshly cleaned stainless steel was placed in an Oxford Industries FlexAL for Atomic Layer Deposition (ALD). First, the chamber was evacuated to <5×10$^{-6}$ ton. The chamber was subsequently dosed for 0.6 seconds with argon bubbled through bis(t-butylamino)silane, followed by purging of the chamber for 5.5 seconds, followed by a plasma pulse of 300 W for 5 seconds and an additional purge for 2 seconds, during which the pressure was maintained at 15 mTorr. This cycle of silica precursor addition, and plasma pulsing was repeated, throughout which oxygen was continually flowing at 60 sccm. Flat samples and stents were exposed to the same number of cycles on two sides. Each cycle makes a layer of approximately 1.25 Å in thickness. The samples were then characterized using XPS and the results shown in FIG. 13.

Preparation of Alumina-Coated Stainless Steel Surfaces Using ALD

Figure 12A:
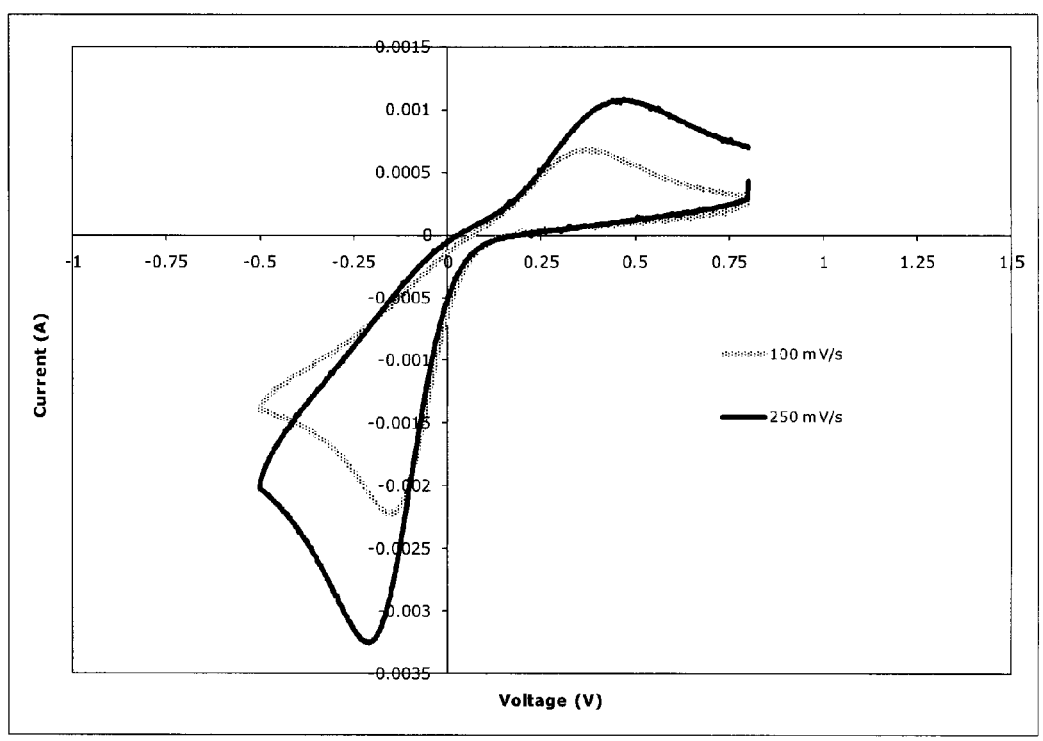
FIG. 12A is a cyclic voltammogram of clean stainless steel, that can be used in one embodiment of the present invention.
Figure 12B:
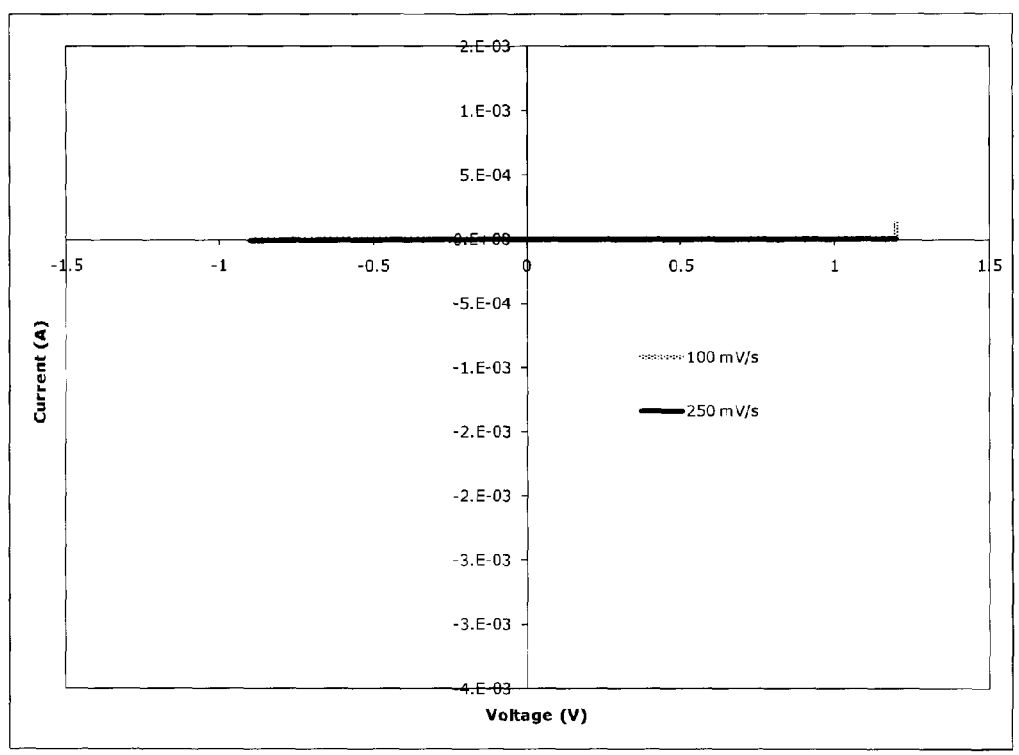
FIG. 12B is a cyclic voltammogram of stainless steel coated with 5 nm alumina by atomic layer deposition, that can be used in one embodiment of the present invention.

Freshly cleaned stainless steel was placed in an Oxford Industries FlexAL for Atomic Layer Deposition (ALD). First, the chamber was evacuated to <5×10$^{-6}$ torr. The chamber was subsequently dosed for 30 milliseconds with trimethylaluminium, followed by purging of the chamber for 4 seconds, followed by a plasma pulse of 300 W for 3 seconds and an additional purge for 800 milliseconds, during which the pressure was maintained at 15 mTorr. This cycle of silica precursor addition, and plasma pulsing was repeated, throughout which oxygen was continually flowing at 60 seem. Flat samples and stents were exposed to the same number of cycles on each side. Each cycle makes a layer of approximately 1.05 Å in thickness. The samples were characterized using cyclic voltammetry and the results shown in FIG. 12A and FIG. 12B.

Example 10

Conjugation of Carbohydrate to Silica or Alumina Coated Stainless Steel Surface

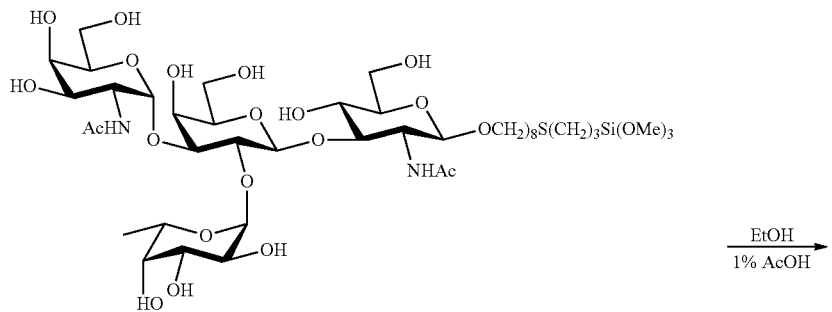

I-14

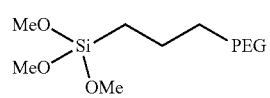

-continued

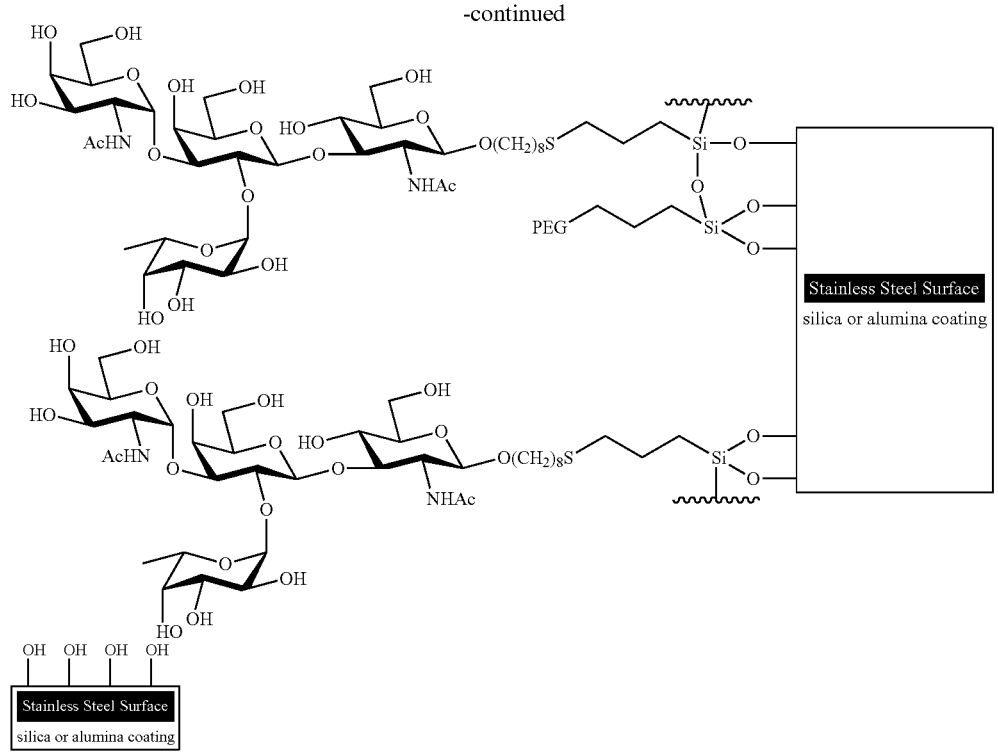

Figure 14:
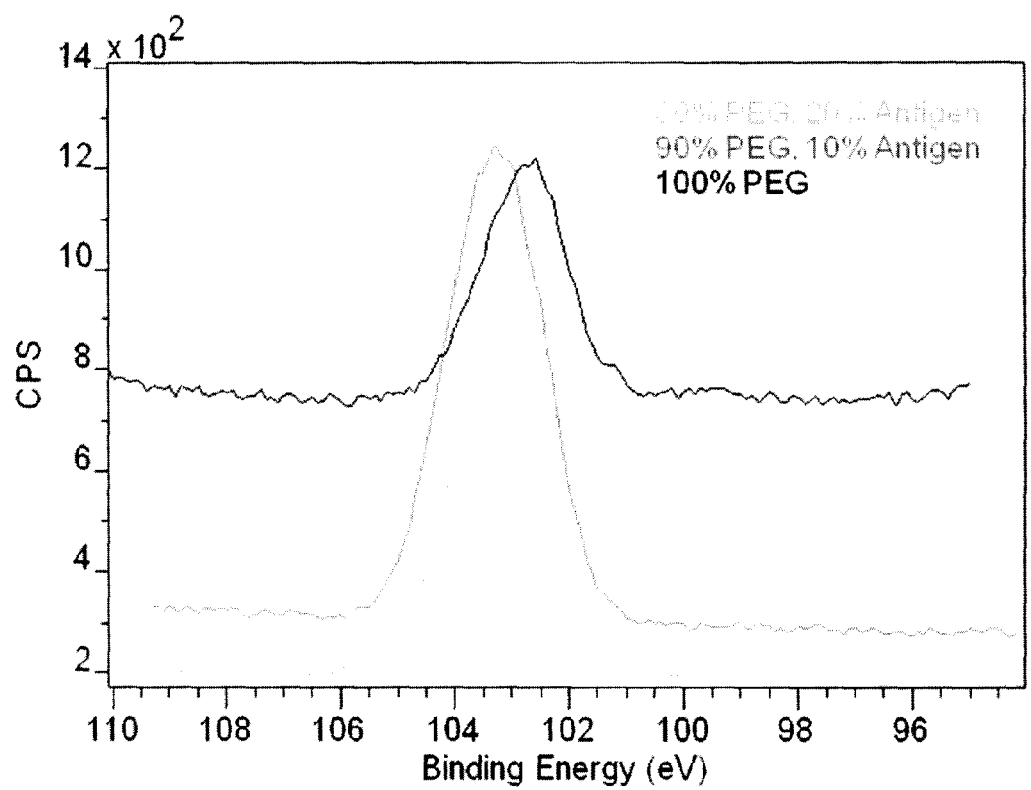
FIG. 14 are high resolution X-ray photoelectron spectra of the Si 2p orbital from silica coated 4 mm×2 mm 316L stainless steel plates coated with A type I antigen covalently bound in approximately 0%, 10%, and 20% of the surface functionalization, according to one embodiment of the present invention.
Figure 15:
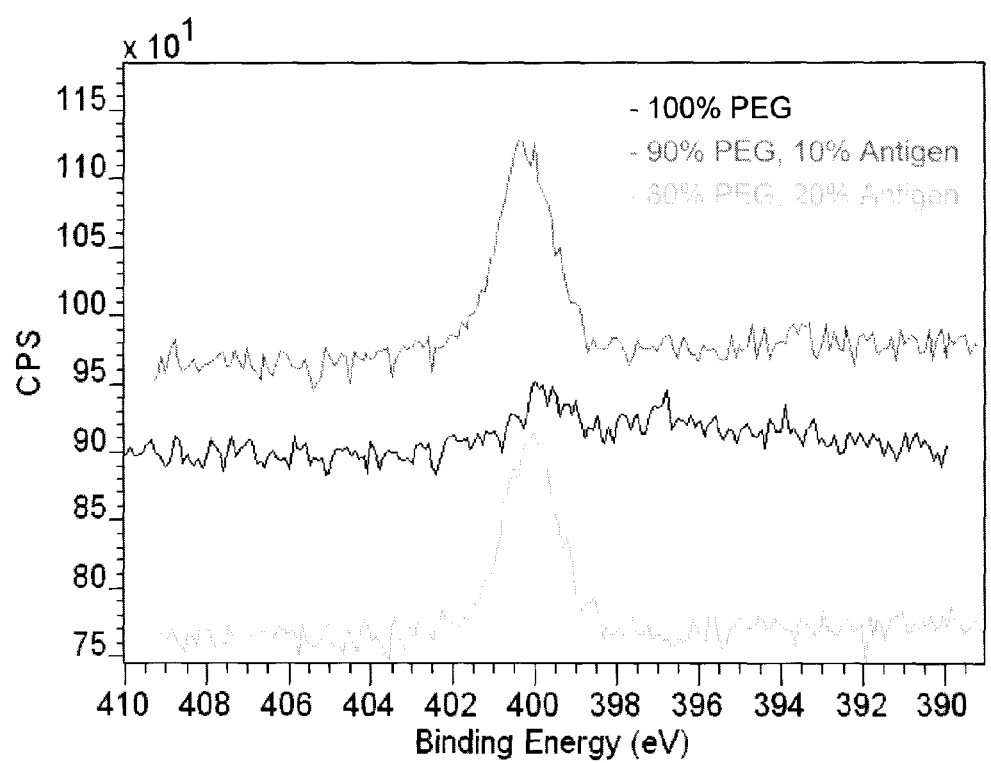
FIG. 15 are high resolution X-ray photoelectron spectra of the N 1s orbital from silica coated 4 mm×2 mm 316L stainless steel plates coated with A type I antigen covalently bound in approximately 0%, 10%, and 20% of the surface functionalization, according to one embodiment of the present invention. The type A I tetrasaccharide has several amide groups, so nitrogen is present on the surface of the 10% and 20% antigen samples. Nitrogen above the background level was not detected on the 100% PEG silane sample.
Figure 16:
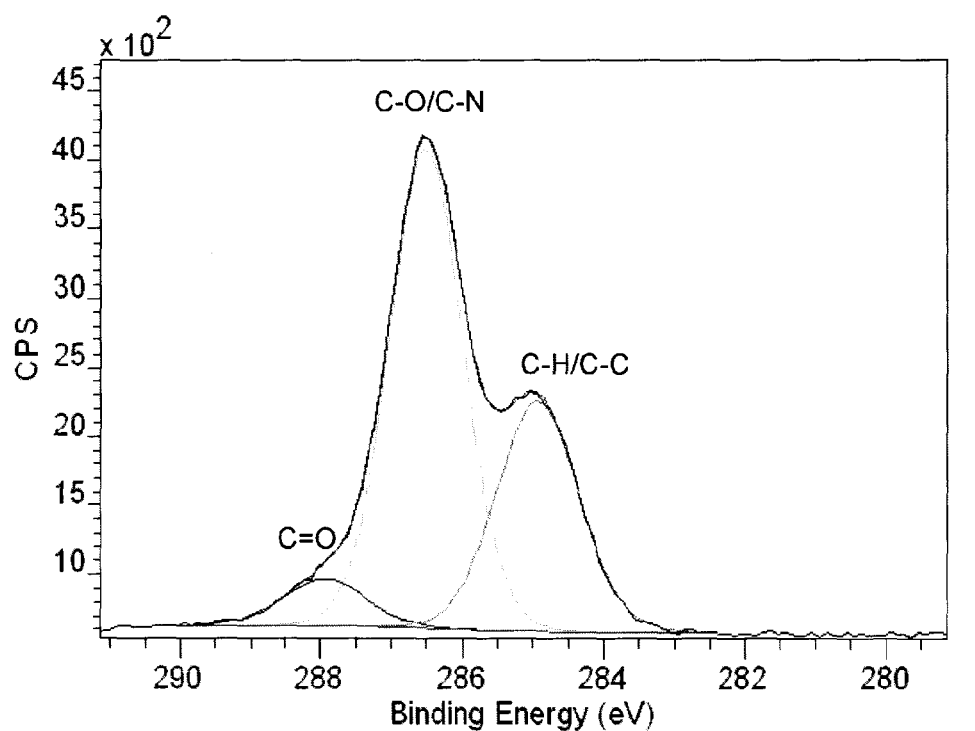
FIG. 16 is a deconvoluted high resolution X-ray photoelectron spectrum of the C 1s orbital from a silica coated 4 mm×2 mm 316L stainless steel plate with 20% A type I antigen, 80% PEG silane surface functionalization, according to one embodiment of the present invention. The deconvoluted C 1s orbital reveals the contributions made from the different types of carbon detected on the sample surface. Peaks that can be assigned to the C=O, C—O/C—N, and C—C/C—H are observed. These functional groups are expected for an antigen/PEG surface.

20% Carbohydrate, 80% PEG Surface Functionalization of Silica or Alumina Coated Stainless Steel In a typical experiment, the carbohydrate I-14 ($4.82 \times 10^{-6}$ mol), was dissolved in 0.25 mL of 95% EtOH with 1% AcOH. To this solution was added 0.47 mL of a solution comprised of 9.4 µL of 2-[methoxy(polyethyleneoxy)propyl]-trimethoxysilane (10 mg, average MW=552 g/mol, $1.93 \times 10^{-5}$ mol), 95% EtOH with 1% AcOH. This solution of silanes was allowed to stand for 5 minutes prior to use to allow for the hydrolysis of the trimethoxysilane groups to silanols. The sample was agitated in the trimethoxysilanes solution for 2 minutes, prior to dip rinsing in 100% EtOH, and curing for 15 minutes in an oven heated to 110° C. The same procedure can be used for carbohydrates A-6 and B-4. The surfaces were then characterized using XPS and the results shown on FIG. 14, FIG. 15 and FIG. 16.

10% Carbohydrate, 90% PEG Surface Functionalization of Silica or Alumina Coated Stainless Steel In a typical experiment, the carbohydrate I-14 ($4.82 \times 10^{-6}$ mol), was dissolved in 0.25 mL of 95% EtOH with 1% AcOH. To this solution was added 1.06 mL of a solution comprised of 21 µL of 2-[methoxy(polyethyleneoxy)propyl]-trimethoxysilane (23 mg, average MW=552 g/mol, $4.34 \times 10^{-5}$ mol), 95% EtOH with 1% AcOH. This solution of silanes was allowed to stand for 5 minutes prior to use to allow for the hydrolysis of the trimethoxysilane groups to silanols. The sample was agitated in the trimethoxysilanes solution for 2 minutes, prior to dip rinsing in 100% EtOH, and curing for 15 minutes in an oven heated to 110° C. The same procedure can be used for carbohydrates A-6 and B-4. The surfaces were then characterized using XPS and the results shown on FIG. 14 and FIG. 15.

100% PEG Surface Functionalization of Silica or Alumina Coated Stainless Steel

In a typical experiment, 22 µL of 2-[methoxy(polyethyleneoxy)propyl]-trimethoxysilane (24 mg; $4.33 \times 10^{-5}$ mol) was dissolved in 1.0 mL of 95% EtOH with 1% AcOH. This silane solution was allowed to stand for 5 minutes prior to use to allow for the hydrolysis of the trimethoxysilane groups to silanols. The sample was agitated in the trimethoxysilane solution for 2 minutes, prior to dip rinsing in 100% EtOH, and curing for 15 minutes in an oven heated to 110° C.

Example 11

Figure 17:
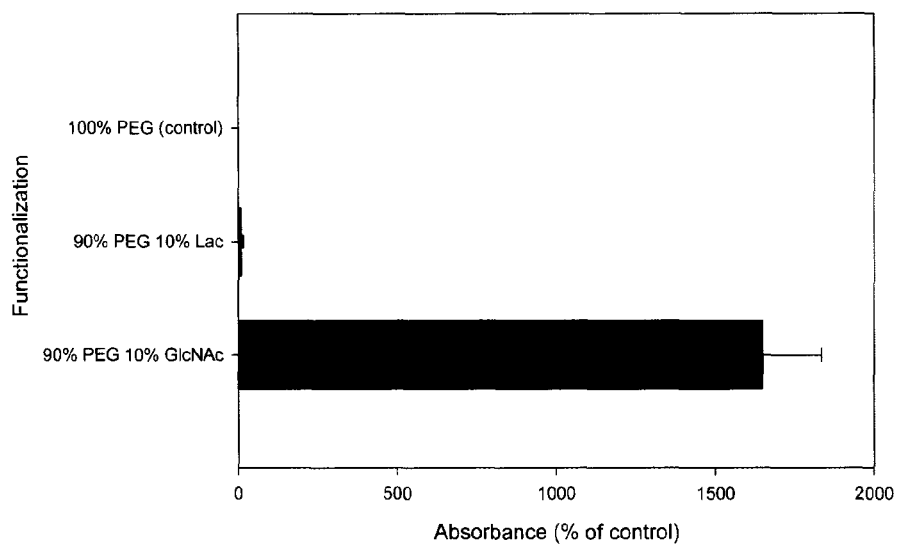
FIG. 17 is a bar graph of results from a modified ELISA assay confirming the attachment of A-6 to silica-coated stainless steel, according to one embodiment of the present invention.
Figure 18:
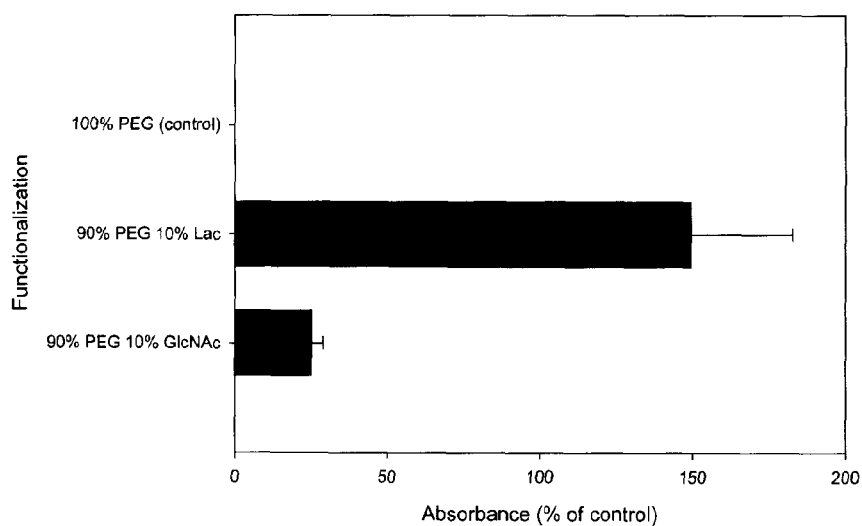
FIG. 18 is a bar graph of results from a modified ELISA assay confirming the attachment of B-4 to silica-coated stainless steel, according to one embodiment of the present invention.

Confirmation of Attachment of Carbohydrate to Silica or Alumina Coated Stainless Steel Using a Modified ELISA Assay Confirmation of Attachment of A-6 and B-4 to Silica-Coated Stainless Steel Each silica stainless steel surface was treated with a solution of 2% BSA in PBST (100 µL) and shaken (14 h, 5° C.). The surface was then removed and then incubated at room temperature with a solution of the peroxidase conjugated lectin (WGA or PNA) (0.1 mg/mL, 100 µL) in 2% BSA PBST for 2 hours with shaking. The surface was thoroughly washed with PBST to remove unbound lectin and then treated with a solution of SigmaFast OPD (400 µL, 1 h). An aliquot of this solution (100 µL) was then taken and the absorbance measured at 450 nm. The results were collated and presented on a bar graph and are shown on FIG. 17 and FIG. 18.

Confirmation of Attachment of A-6 and to Alumina-Coated Stainless Steel

Figure 19:
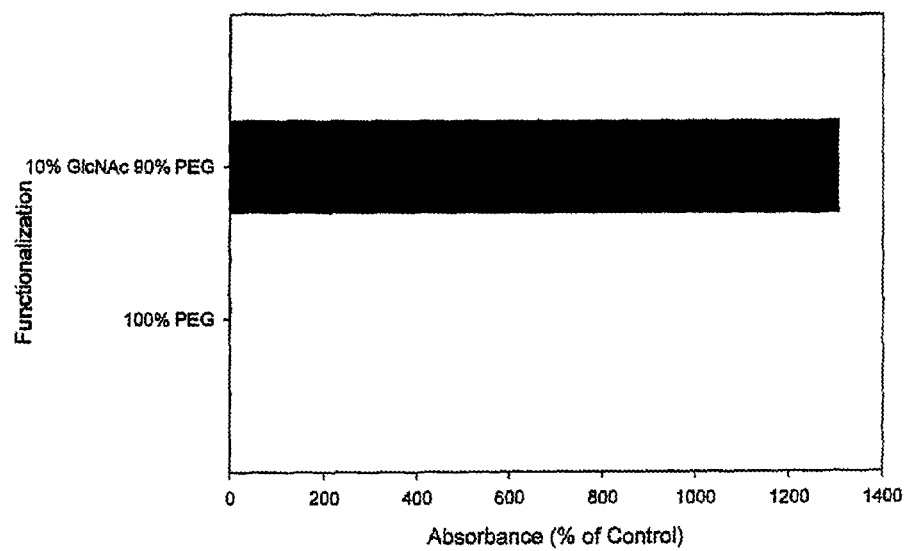
FIG. 19 is a bar graph of results from a modified ELISA assay confirming the attachment of A-6 to alumina-coated stainless steel, according to one embodiment of the present invention.

Each alumina-coated stainless steel surface was treated with a solution of 2% BSA in PBST (100 µL) and shaken (14 h, 5° C.). The surface was then removed and then incubated at room temperature with a solution of peroxidase conjugated WGA (0.01 mg/mL, 100 µL) in 2% BSA PBST for 2 hours with shaking. The surface was thoroughly washed with PBST to remove unbound lectin and then treated with a solution of SigmaFast OPD (400 µL, 1 h). An aliquot of this solution (100

μL) was then taken and the absorbance measured at 450 nm. The results were collated and presented on a bar graph (FIG. 19).

Confirmation of Attachment of I-14 and to Silica-Coated Stainless Steel Stent

Figure 20:
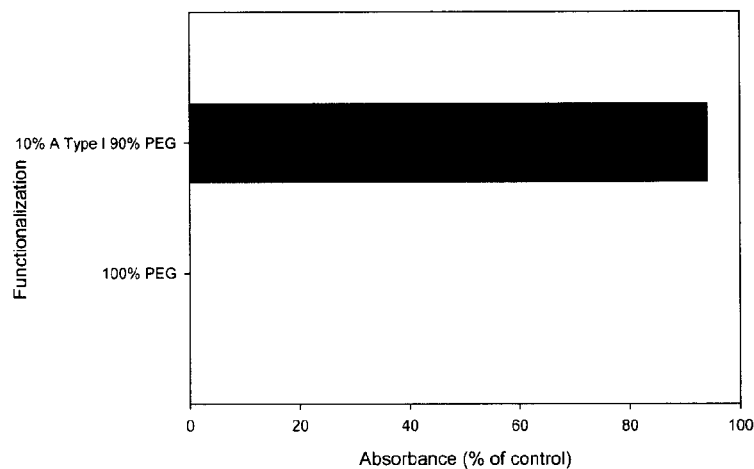
FIG. 20 is a bar graph of results from a modified ELISA assay confirming the attachment of I-14 to silica-coated stainless steel, according to one embodiment of the present invention.

Each silica-coated stainless steel stent surface was treated with a solution of 2% BSA in PBST (200 μL) and shaken (14 h, 5° C.). The surface was then removed and then incubated with mouse anti-A IgM antibodies (5° C., 14 h, 0.023 mg/mL, 50 μL). The surface was then removed, thoroughly washed with PBST and then treated with a secondary HRP conjugated goat anti-mouse IgM antibody (21° C., 3 h, 0.013 mg/mL, 50 μL). The surface was thoroughly washed with PBST to remove unbound antibody and then treated with a solution of SigmaFast OPD (200 μL, 1 h). An aliquot of this solution (100 μL) was then taken and the absorbance measured at 450 nm. The results were collated and presented on a bar graph (FIG. 20).

Blood Plasma Stability Studies of A Type I Antigen Functionalized Stainless Steel Surfaces Several silica-coated stainless steel samples bearing the A type I antigen were prepared, according to the general procedure defined above. Each of the samples was placed in three different types of pig blood plasma (blood group O, blood group A and commercial pooled blood group O plasma). The samples were agitated on a shaker table for 12 days. After 12 days, the samples were removed from the pig blood plasma and placed in ethanol.

Figure 21:
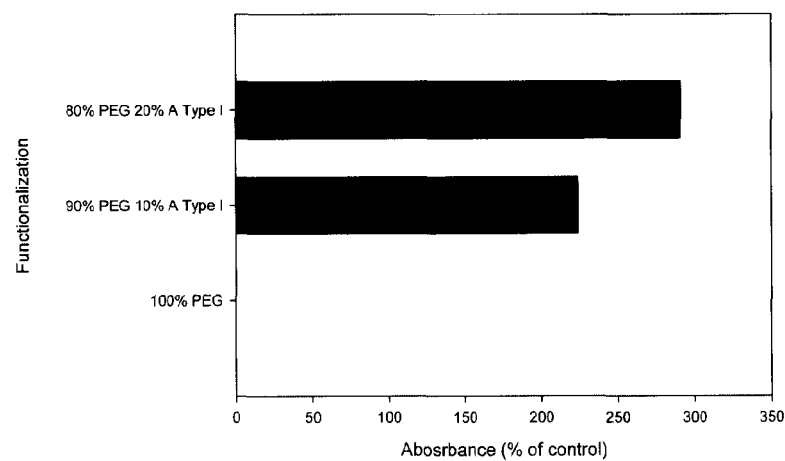
FIG. 21 is a bar graph of results from a modified ELISA assay confirming the attachment of I-14 to silica-coated stainless steel after incubation with pig-pooled O blood plasma, according to one embodiment of the present invention.
Figure 22:
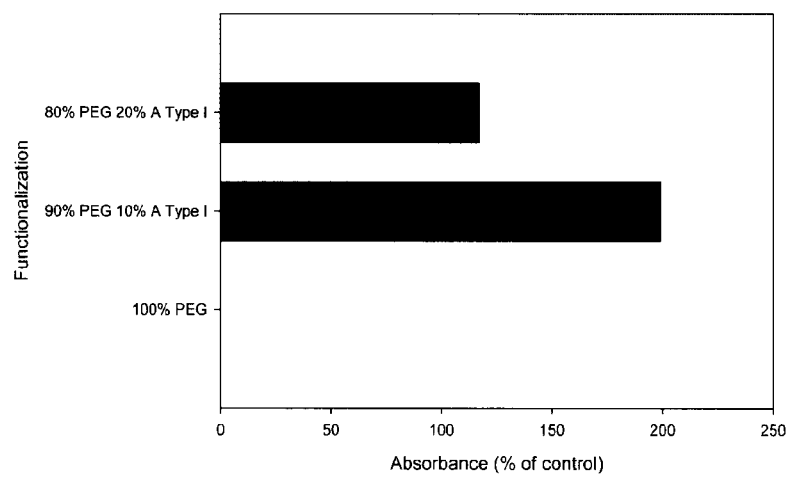
FIG. 22 is a bar graph of results from a modified ELISA assay confirming the attachment of I-14 to silica-coated stainless steel after incubation with pig O blood plasma, according to one embodiment of the present invention.
Figure 23:
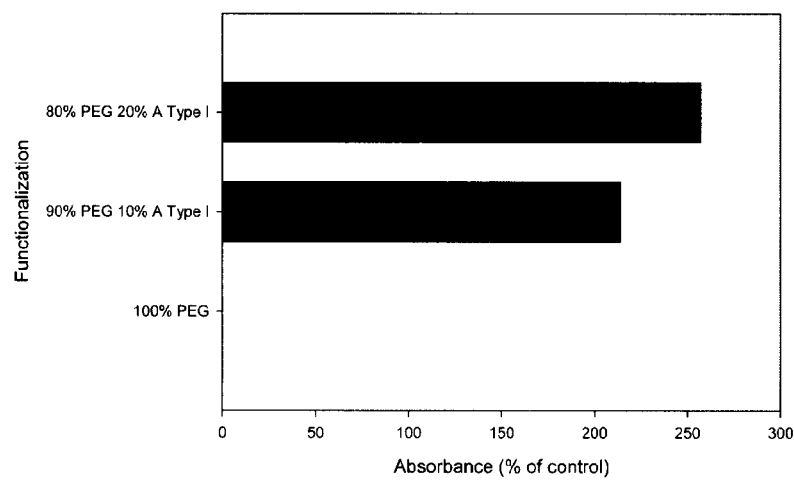
FIG. 23 is a bar graph of results from a modified ELISA assay confirming the attachment of I-14 to silica-coated stainless steel after incubation with pig A blood plasma, according to one embodiment of the present invention.

Each silica-coated stainless steel stent surface was treated with a solution of 2% BSA in PBST (200 μL) and shaken (14 h, 5° C.). The surface was then removed and then incubated with mouse anti-A IgM antibodies (5° C., 14 h, 0.023 mg/mL, 50 μL). The surface was then removed, thoroughly washed with PBST and then treated with a secondary HRP conjugated goat anti-mouse IgM antibody (21° C., 3 h, 0.013 mg/mL, 50 μL). The surface was thoroughly washed with PBST to remove unbound antibody and then treated with a solution of SigmaFast OPD (200 μL, 1 h). An aliquot of this solution (100 μL) was then taken and the absorbance measured at 450 nm. These results were then collated and presented as a series of bar graphs (FIG. 21, FIG. 22 and FIG. 23).

Example 12

Preparation of Silica Nanoparticles

Preparation of Silica-Coated $Fe_3O_4$ Nanoparticles

In a typical experiment, the $Fe_3O_4$ nanoparticles are prepared via a base catalyzed co-crystallization of Fe(II) and Fe(III) salts in a xylene:water reverse micelle solution with sodium dodecylbenzenesulphonate as the surfactant. The $Fe_3O_4$ nanoparticle solution is aged for several hours at an elevated temperature to ensure the formation of the nanoparticles. Upon lowering the temperature, a small amount of TEOS was added to the reaction mixture to initiate the formation of a $SiO_2$ outer shell on the nanoparticles. The volume of TEOS added directly affects the thickness of the resulting $SiO_2$ shell, however the size of the resulting nanoparticles showed great variation in the preparation of larger particles. These core shell nanoparticles were isolated and cleaned via a centrifugation-dispersion cycle that was repeated three times. Once clean, the silica-coated $Fe_3O_4$ nanoparticles were left suspended in ethanol. A measured volume of known concentration of the nanoparticle suspension was then used as seeds in a Stöber $SiO_2$ nanoparticle preparation to increase the size of the $SiO_2$ shell in a more controlled fashion. Upon increasing the thickness of the $SiO_2$ shell to the desired diameter (30-2000 nm), the surface of the nanoparticles were subsequently functionalized via the addition of appropriate silanes to the reaction mixture. The addition of PEG, saccharide, and fluorophore coupled silanes resulted in similarly functionalized nanoparticles, with the surface functionalization reflecting the initial silane ratios. In some preparations, only PEG-silane and MPTMS (3-mercaptopropyltrimethoxysilane) in a 4:1 ratio were used. Saccharide and fluorophore molecules were subsequently coupled to the thiol groups comprising 20% of the nanoparticle surface. The resulting functionalized silica-coated $Fe_3O_4$ nanoparticles were cleaned and isolated by three centrifugation-dispersion cycles, and finally dispersed into an appropriate solvent such as an aqueous PBS solution. Nanoparticle solutions were stored at 4° C. until used. The nanoparticles were characterized via FTIR spectroscopy, XPS, EA, and a saccharide specific assay.

Preparation of Fluorescent (Dye-Incorporated) Silica Nanoparticles

Figure 9:
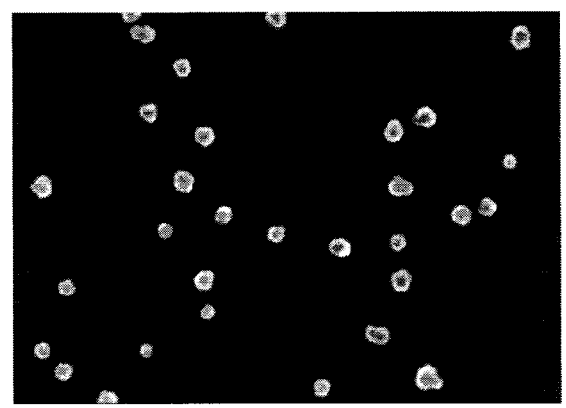
FIG. 9 is a scanning electron microscopy image of dye-core fluorescent $SiO_2$ nanoparticles, according to one embodiment of the present invention.
Figure 10A:
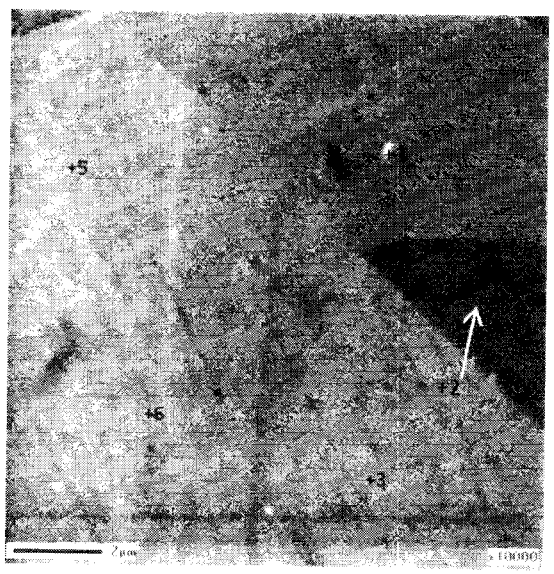
FIG. 10A is a scanning electron micrograph of an untreated 316L stainless steel stent that can be used in one embodiment of the present invention. The black crosses indicate sample points at which Auger electron spectroscopy was performed, the spectra of which are shown in FIG. 10B. The grey scale bar is 2 µm.
Figure 10B:
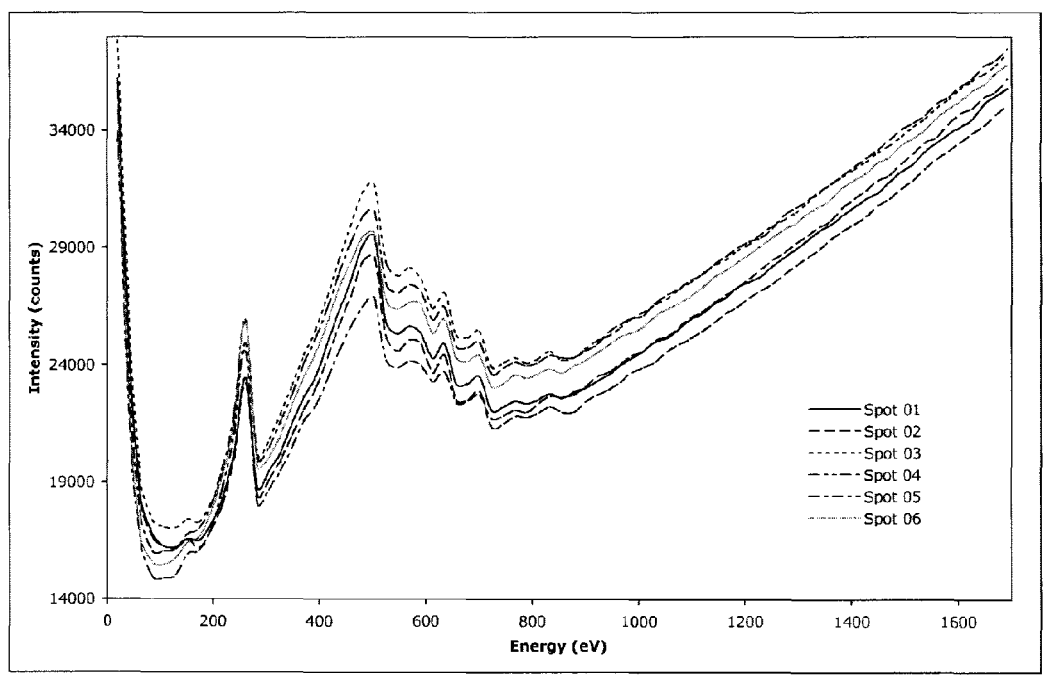
FIG. 10B is an Auger electron spectra of an untreated 316L stainless steel stent that can be used in one embodiment of the present invention. The spots refer to the sampling points noted in FIG. 10A. The Auger electron spectra reveal signals for Fe, Cr, Ni, C, and O, but not silicon. The signal for silicon is expected at a binding energy of approximately 1615 eV, and is not observed.
Figure 11A:
FIG. 11A is a scanning electron micrograph of a 316L stainless steel stent covered with an $SiO_2$ layer, prepared using a TEOS dip that can be used in one embodiment of the present invention. The crosses and numbers denote the seven sampling points for Auger Electron Spectroscopy, the spectra of which are shown in FIG. 11B. The scale bar is 2 µm.
Figure 11B:
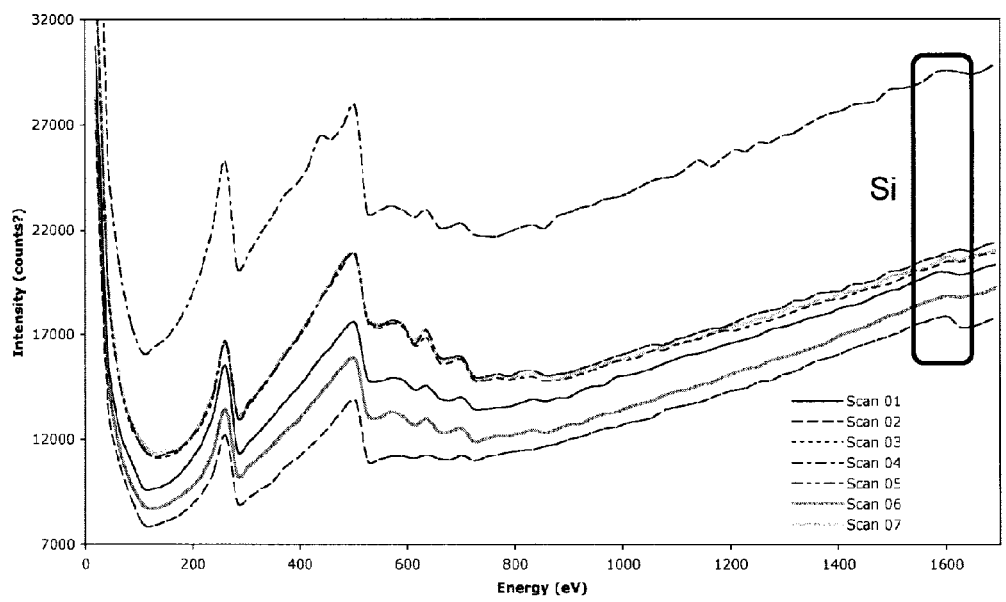
FIG. 11B is an Auger electron spectra of a $SiO_2$-coated 316L stainless steel stent that can be used in one embodiment of the present invention. The spots refer to the sampling points noted in FIG. 11A. The Auger electron spectra reveal signals for Fe, Cr, Ni, C, and O, as well as Si. The signal for silicon is expected at a binding energy of approximately 1615 eV, and has been highlighted by outlining with a black rectangle in the figure.

In a typical experiment, the selected organic dye with an appropriate amine reactive substituent is weighed out into a vial in a glove box. 1-5 mg are typically used depending on the amount and size of particles required. The organic dye is then dissolved in 1-5 mL of anhydrous ethanol. 2-50 equivalents of aminopropyltrimethoxysilane (APTMS), or 2-20 μL of the neat silane is added to the vial while the dye solution is vigorously stirred. The vial is then encased in aluminum foil, and left to stir for 12-16 hours in the dark, at room temperature. The APTMS coupled organic dye solution can then be added to an ethanolic solution containing appropriate amounts of water and ammonia, and tetraethoxy orthosilicate (TEOS). Varying the concentrations of water, ammonia and TEOS in the reaction mixture can control the size of the nanoparticles. The organic dye distribution in the nanoparticle can be controlled via the order of addition of reagents, namely TEOS. In some reactions, several aliquots of TEOS were added to grow the nanoparticles to a larger size. Once the reaction producing the nanoparticles is complete, the surface of the nanoparticles may be functionalized via established silane coupling chemistry in the same reaction vessel. Once functionalized, the resulting nanoparticles were cleaned and isolated by three centrifugation-dispersion cycles, and finally dispersed into an appropriate solvent. The nanoparticles were characterized via SEM (FIG. 9), DLS, and UV/Vis spectroscopy.

Preparation of Silica Nanoparticles

In a typical experiment, 100 mL of 100% ethanol was stirred with 6.2 mL 28% ammonia and 0.42 mL Millipore water for 30 minutes. Then 3.56 mL TEOS was added and the reaction was allowed to stir overnight. For the described conditions the nanoparticles have a diameter of approximately 100 nm. In most instances, the nanoparticles were functionalized in the same reaction vessel using silane coupling chemistry using a variety of silanes depending on the intended application. In some instances the nanoparticles were cleaned through three cycles of centrifugation and redispersion in fresh ethanol. The nanoparticles were characterized by SEM and DLS.

Example 13

Preparation of Carbohydrate Functionalized Nanoparticles Utilizing an Alkoxy Silane Linker

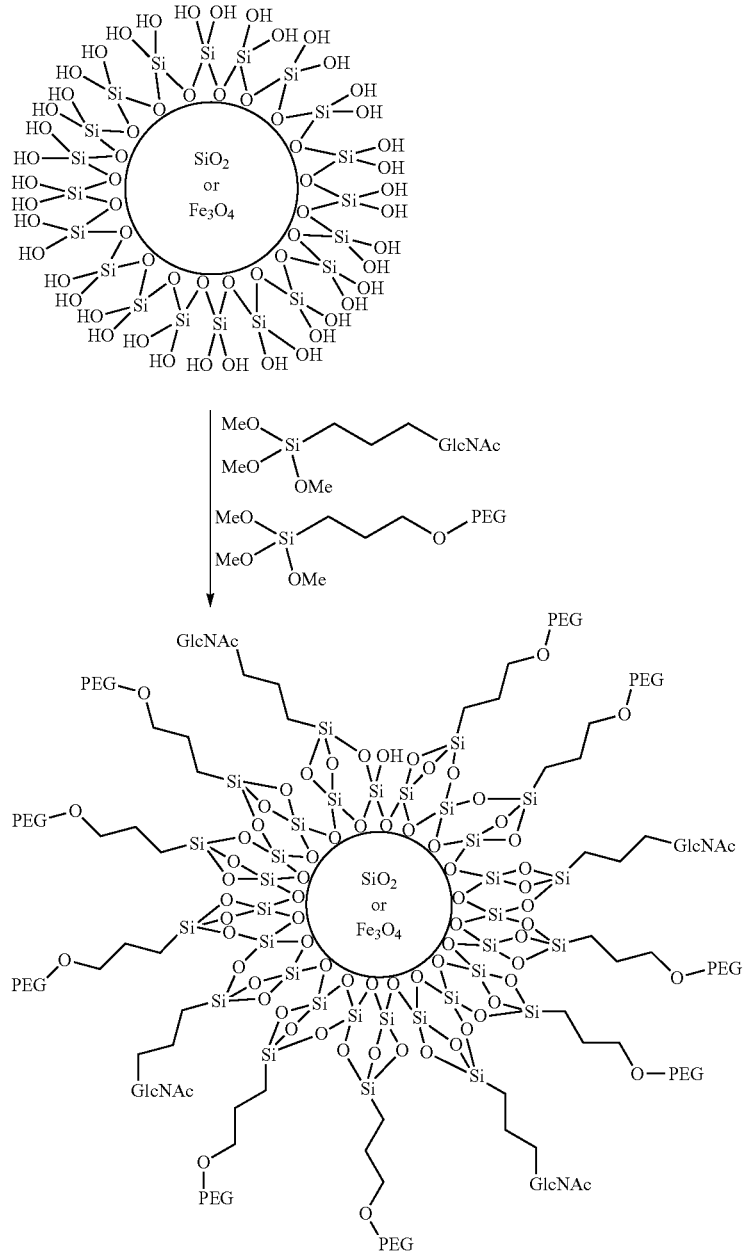

Preparation of 100% PEG Nanoparticles

Figure 24:
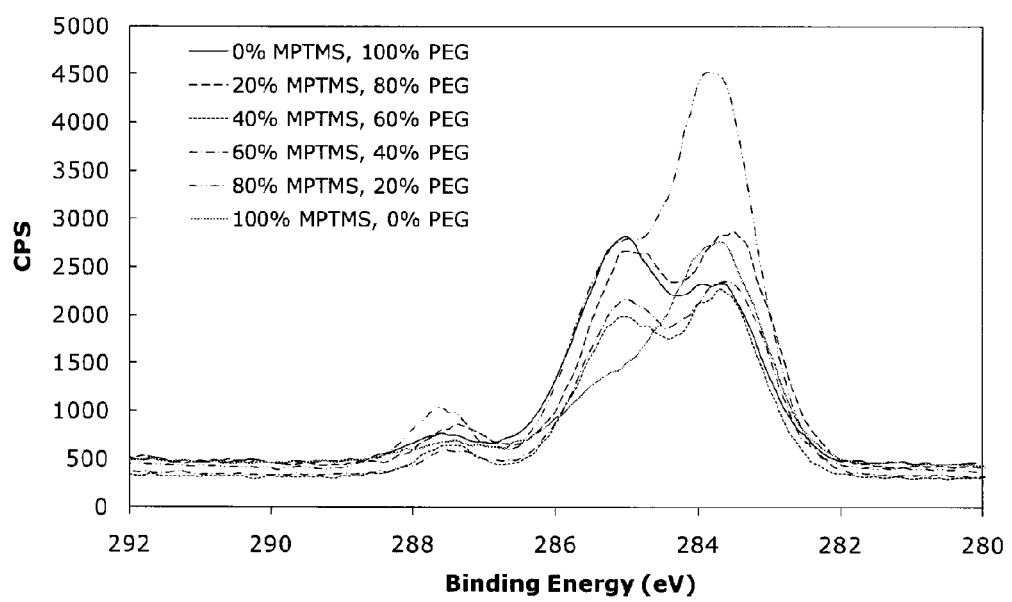
FIG. 24 is high resolution X-ray photoelectron spectra of the C 1s orbital of $SiO_2$ nanoparticles with different ratios of MPTMS and PEG silane surface functionalization, according to one embodiment of the present invention. X-Ray photoelectron spectroscopy is a surface sensitive technique and it samples from the top several nanometers of a surface. Each element has a characteristic energy for the core electrons, which is measured when the electron is knocked from its orbital by an X-ray. This characteristic binding energy is also sensitive to the oxidation state of the atom from which the electron came, as well as substituents. A carbon atom surrounded by other carbon atoms (C—C), or hydrogen atoms (C—H) typically has a binding energy of 285.0 eV, and this signal is used as a reference. C—O and C—N bonds have a slightly higher binding energy, approximately 286.5 eV, and C=O bonds slightly higher yet at approximately 288.5 eV. In this figure, the C—O peak can be seen to decrease as the percentage of PEG silane in the surface functionalization decreases. For a 100% PEG silane surface, the C—O peak is the most intense, in contrast to 100% MPTMS in which the C—H signal is the strongest. These results illustrate that it can be straightforward to control the incorporation of different silanes onto the silica nanoparticle surface.
Figure 25:
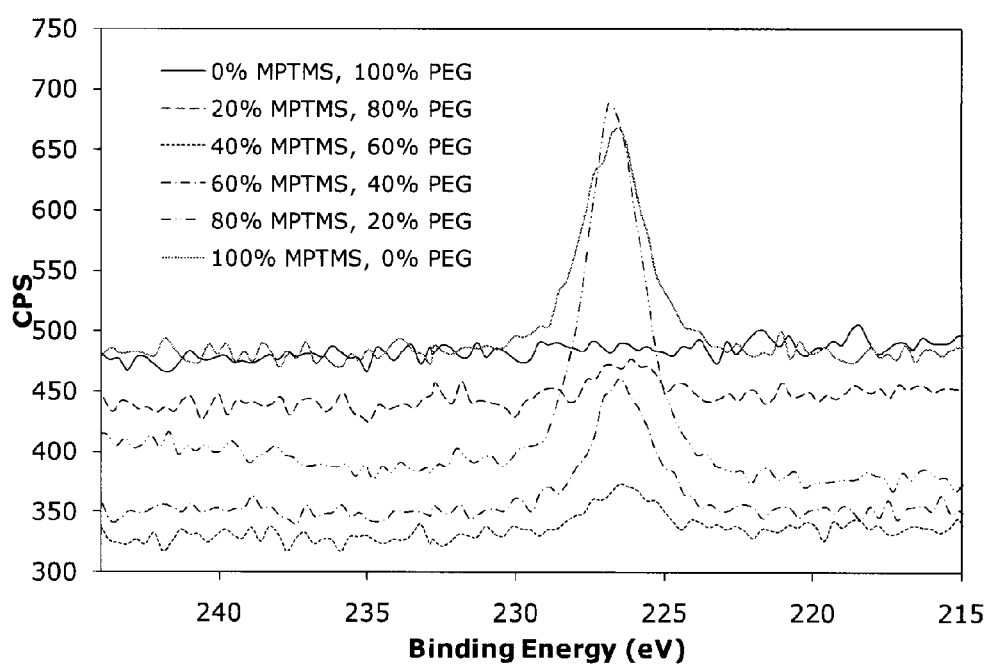
FIG. 25 is high resolution X-ray photoelectron spectra of the S 2p orbital of $SiO_2$ nanoparticles with different ratios of MPTMS and PEG silane surface functionalization, according to one embodiment of the present invention. As the percentage of mercaptopropyltrimethoxysiilane (MPTMS) of the surface functionalization increases, the strength of the S 2p signal also increases. The peak should be the most intense for the 100% MPTMS, but instead appears to be seen for the 80% MPTMS, 20% PEG spectrum. This can be rationalized by difficulty in obtaining repeatable sample thickness when dealing with a powder, and not a solid substrate sample. Also, without any PEG silane on the surface, the coating is thinner, and thus more of the sample consists of the silicon and oxygen atoms from the nanoparticle, and not of the organic surface functionalization.

A batch of silica nanoparticles are prepared as described above. Once the condensation reaction that produces the nanoparticles from the TEOS precursor has reached completion, the basic ethanolic solution can be used to catalyze further silane coupling chemistry. In a typical experiment, 4-5 μL of PEG silane is added to 35 mL of the 100 nm diameter silica nanoparticle reaction mixture. The reaction was allowed to stir at room temperature for 6-12 hours before isolating the PEG functionalized nanoparticles via centrifugation. The nanoparticles were cleaned through five cycles of centrifugation and redispersion, the penultimate and final dispersions being in water. The nanoparticles were characterized via SEM (FIG. 24 and FIG. 25), DLS, and FTIR spectroscopy.

Preparation of 90% PEG 10% GlcNAc Nanoparticles

Figure 26:
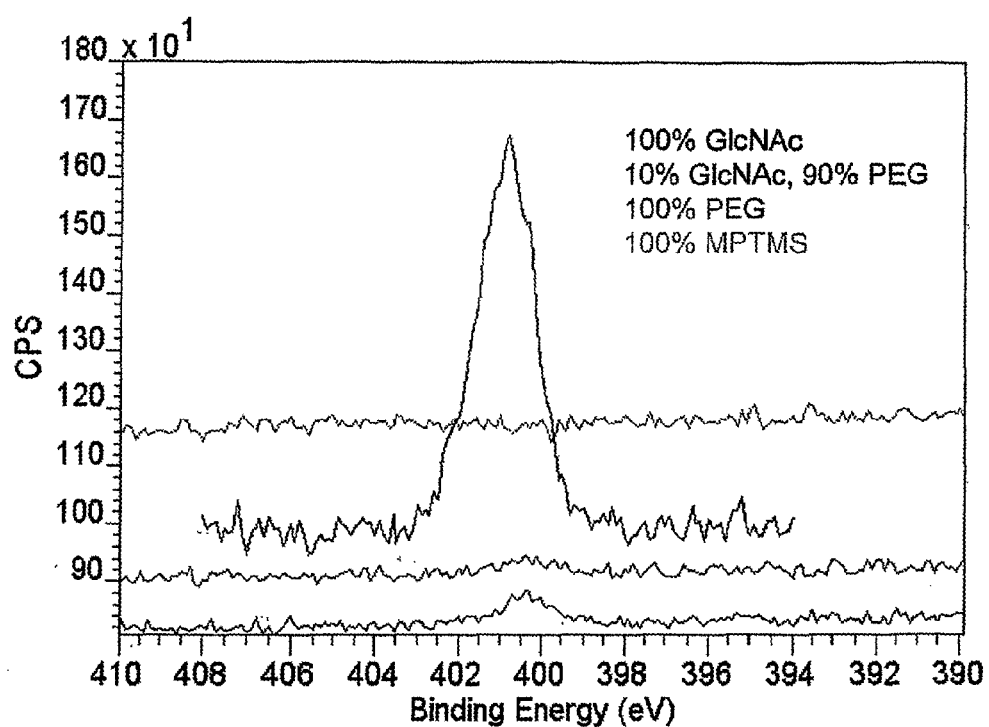
FIG. 26 is high resolution X-ray photoelectron spectra of the N 1 s orbital from four samples of silica nanoparticles with different surface functionalizations, according to one embodiment of the present invention. Nitrogen is detected in significant amounts in the 100% monosaccharide (GlcNAc) functionalized sample, and in moderate amounts in the 10% GlcNAc, 90% PEG sample. The nitrogen is present due to the amide functionalities of the monosaccharide, and is not detected in the 100% PEG or 100% MPTMS functionalized silica nanoparticle samples.
Figure 27:
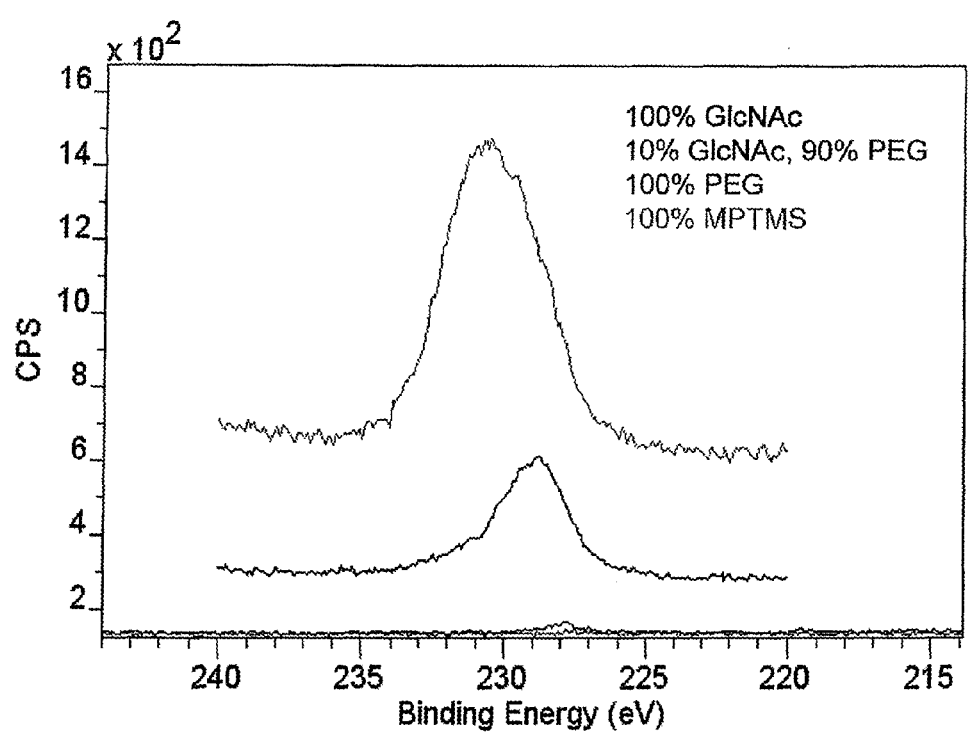
FIG. 27 is high resolution X-ray photoelectron spectra of the S 2 s orbital from 4 samples of silica nanoparticles with different surface functionalizations, according to one embodiment of the present invention. Sulphur is detected in significant quantities for the 100% MPTMS and the 100% monosaccharide (GlcNAc) samples. The MPTMS molecule undergoes a thiol-ene reaction to covalently attach a tri-methoxysilane moiety to the monosaccharide. Thus, the presence of sulphur indicates that the monosaccharide is covalently bound to the silica nanoparticle surface. A very small amount of sulphur is detected in the 10% GlcNAc, 90% PEG sample, but the quantity is not significantly greater than for the 100% PEG sample.

In a typical experiment, 0.28 mg of MS and 3.7 μL of PEG silane are dissolved in 1 mL of ethanol. This solution is added to 35 mL of the 100 nm diameter silica nanoparticle reaction mixture. The reaction was allowed to stir at room temperature for 12 hours before isolating the 90% PEG 10% GlcNAc functionalized silica nanoparticles via centrifugation. The nanoparticles were cleaned through five cycles of centrifugation and redispersion, the penultimate and final dispersions being in water. The nanoparticles were characterized via SEM (FIG. 26 and FIG. 27), DLS, and a fluorescence bioassay described below.

Example 14
Preparation of Carbohydrate Functionalized Nanoparticles Utilizing an Activated Ester (PNP) Linker
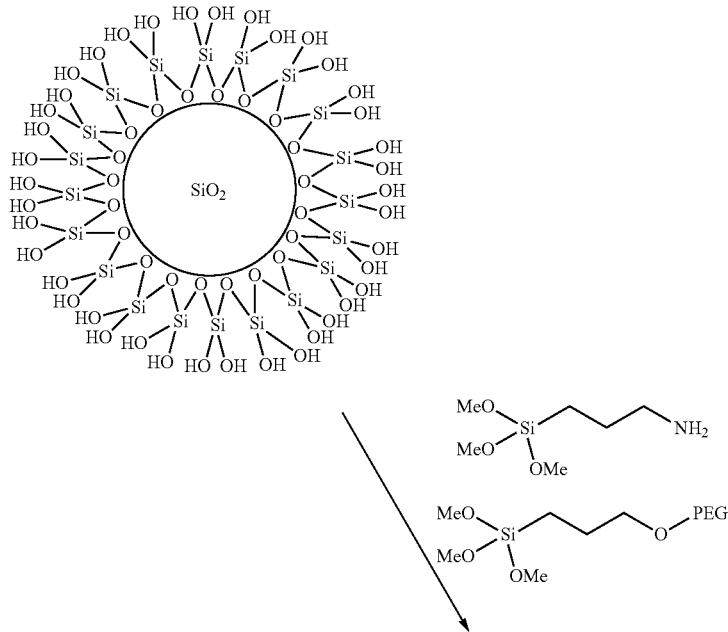
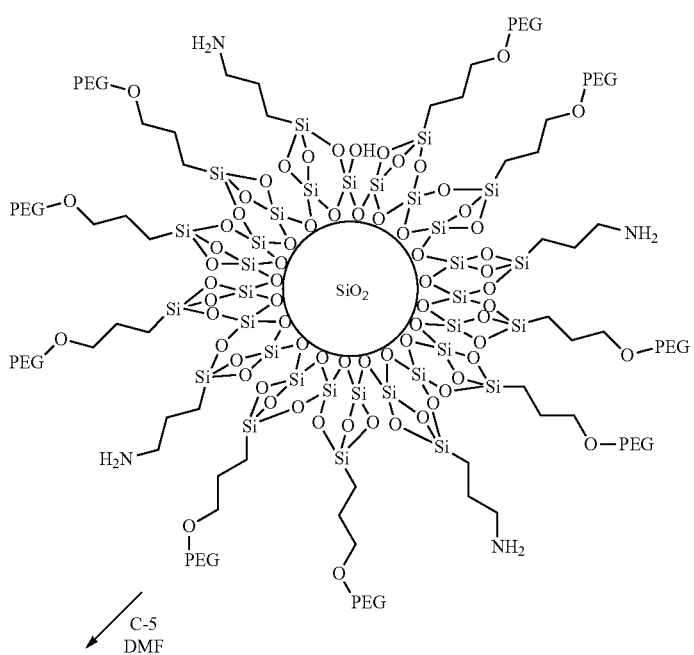

-continued

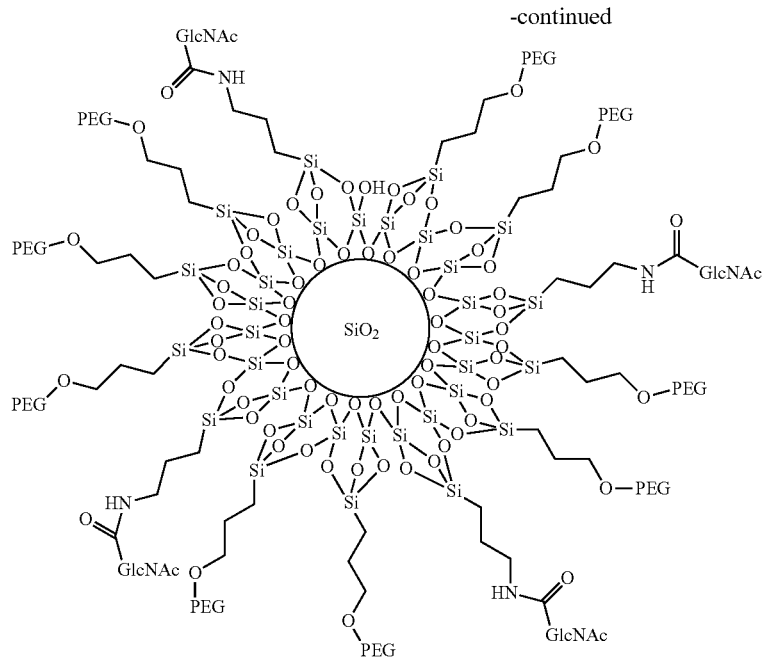

Preparation of Aminated Nanoparticles

In a typical experiment, 1.5 µL of aminopropyltrimethoxysilane (APTMS) is added to 35 mL of the 100 nm diameter silica nanoparticle reaction mixture. The reaction was allowed to stir at room temperature for 6-12 hours before isolating the amine functionalized nanoparticles via centrifugation. The nanoparticles were cleaned through three cycles of centrifugation and redispersion. From the final centrifugation step, the nanoparticle pellet was placed into a round bottom flask. The nanoparticles were placed under vacuum (~0.2 Torr) overnight, while heated to 100° C. in an oil-bath. Subsequently, the nanoparticles were redispersed into dry DMF. The nanoparticles were characterized via SEM, DLS, and FTIR spectroscopy.

Preparation of 90% PEG 10% Amine Nanoparticles

In a typical experiment, 0.4 µL of aminopropyltrimethoxysilane (APTMS) and 3.4 µL of PEG silane is added to 100 mL of the 100 nm diameter silica nanoparticle reaction mixture. The reaction was allowed to stir at room temperature for 6-12 hours before isolating the 90% PEG 10% amine functionalized nanoparticles via centrifugation. The nanoparticles were cleaned through three cycles of centrifugation and redispersion. From the final centrifugation step, the nanoparticle pellet was placed into a round bottom flask. The nanoparticles were placed under vacuum (~0.2 Torr) overnight, while heated to 100° C. in an oil-bath. Subsequently, the nanoparticles were redispersed into dry DMF prior to the addition of the carbohydrate ester. The nanoparticles were characterized via SEM, DLS, and FTIR spectroscopy.

Preparation of 90% PEG 10% GlcNAc Nanoparticles (PNP)

A mixture of aminated nanoparticles (100 mg, 90% PEG, 10% Amine) in dry DMF (0.5 mL) was treated with the half ester C-5 (5 mg) and stirred (rt, o/night). The nanoparticles were purified via three cycles of centrifugation and redispersion into 100% ethanol. Two more cycles of centrifugation and redispersion into either Millipore water or PBS were performed before the nanoparticles were characterized via a biological assay, SEM, and DLS.

Example 15

Confirmation of Attachment of Carbohydrate to Silica Nanoparticles

Figure 28:
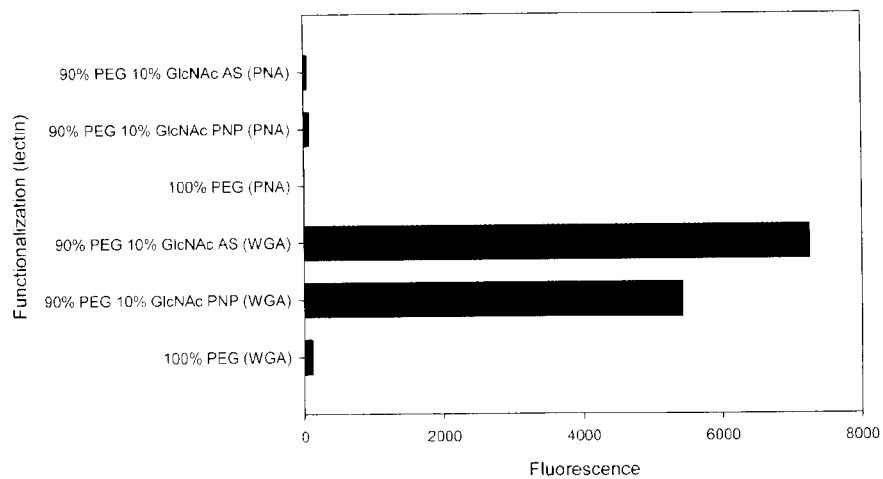
FIG. 28 is a bar graph of results from a microwell fluorescence assay confirming the attachment of A-6 and C-5 to silica nanoparticles, according to one embodiment of the present invention.

Each set of nanoparticles (100% PEG, 90% PEG, 10% GlcNAc AS and 90% PEG 10% GlcNAc PNP) taken up in PBST (100 mg/mL). An aliquot of each solution (90 µL was treated with a solution of 2% BSA in PBST (200 µL) and the mixture gently rocked (5° C., 14 h). The mixture was then centrifuged, treated with a FITC conjugated lectin (WGA or PNA, 1 mg/mL) and the mixture gently rocked (21° C., 2 h). The mixture was centrifuged, the supernatant was discarded and the resulting pellet was suspended in PBS (100 µL); this procedure was repeated twice to remove any unbound lectin. The resulting pellet was placed in a microwell fluorescence plate reader and the fluorescence measured (excitation 444 nm, emission 538 nm, FIG. 28).

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

What is claimed is:

1. An immunologic induction system comprising a tolerogen, the tolerogen comprising at least one non-self blood group antigen coupled to a stent, wherein the tolerogen induces immunologic tolerance.

2. The system of claim 1, wherein the blood group antigen is selected from the group consisting of the A blood group antigen, the B blood group antigen, the O blood group antigen, and fragments and combinations thereof.

3. The system of claim 2, wherein the A blood group antigen, the B blood group antigen and the O blood group antigen are selected from the group consisting of Type I, Type II, Type III, Type IV, Type V, and Type VI blood group antigens.

4. The system of claim 1, wherein a plurality of different blood group antigens are coupled to the stent.

5. The system of claim 1, wherein the blood group antigen is coupled to the stent through a linker.

6. The system of claim 5, wherein the linker is an aglycone that has an anchoring group.

7. The system of claim 6, wherein the anchoring group is selected from the group consisting of a monoalkoxysilyl, a dialkoxysilyl, a trialkoxysilyl, a monohalosilyl, a dihalosilyl, and a trihalosilyl.

8. The system of claim 7, wherein the anchoring group is trimethoxysilyl.

9. The system of claim 7, wherein the anchoring group is trichlorosilyl.

10. The system of claim 1, wherein the stent is made from silica-coated 316L stainless steel.

11. The system of claim 1, wherein the stent is made from $Al_2O_3$-coated 316L stainless steel.

12. The system of claim 1, wherein the tolerogen further comprises a polyethylene glycol (PEG)-containing molecule coupled to the stent.

13. The system of claim 12, wherein the polyethylene glycol-containing molecule comprises a surface binding group selected from the group comprising a monoalkoxysilyl, a dialkoxysilyl, a trialkoxysilyl, a monohalosilyl, a dihalosilyl, and a trihalosilyl.

14. The system of claim 13, wherein the surface binding group is trimethoxysilyl.

15. The system of claim 13, wherein the surface binding group is trichlorosilyl.

16. The system of claim 1, wherein the is administered intravenously.

17. The system of claim 1, wherein the stent is administered through surgical implantation.

18. The system of claim 1, wherein the stent is administered to a neonate.

19. The system of claim 1, wherein the stent is administered to a patient who is growing past the age of infancy.

20. The system of claim 1, wherein the stent is administered to extend the window of safety for immunologically-incompatible transplantations.

21. A tolerogen which induces immunologic tolerance to non-self antigens, the tolerogen comprising at least one non-self blood group antigen coupled to a stent.

22. The tolerogen of claim 21, wherein the blood group antigen is selected from the group consisting of the A blood group antigen, the B blood group antigen, the O blood group antigen, and fragments and combinations thereof.

23. The tolerogen of claim 22, wherein the A blood group antigen, the B blood group antigen and the O blood group antigen are selected from the group consisting of Type I, Type II, Type III, Type IV, Type V, and Type VI blood group antigens.

24. The tolerogen of claim 21, wherein a plurality of different non-self blood group antigens are coupled to the stent.

25. The tolerogen of claim 21, wherein the blood group antigen is coupled to the stent through a linker.

26. The tolerogen of claim 25, wherein the linker is an aglycone that has an anchoring group.

27. The tolerogen of claim 26, wherein the anchoring group is selected from the group consisting of a monoalkoxysilyl, a dialkoxysilyl, a tnalkoxysilyl, a monohalosilyl, a dihalosilyl, and a trihalosilyl.

28. The tolerogen of claim 27, wherein the anchoring group is trimethoxysilyl.

29. The tolerogen of claim 21, wherein the stent is made from silica-coated 316L stainless steel.

30. The tolerogen of claim 21, wherein the stent is made from $Al_2O_3$-coated 316L stainless steel.

31. The tolerogen of claim 21, wherein the tolerogen further comprises a polyethylene glycol (PEG)-containing molecule coupled to the stent.

32. The tolerogen of claim 31, wherein the polyethylene glycol-containing molecule comprises a surface binding group selected from the group consisting of a monoalkoxysilyl, a dialkoxysilyl, a tnalkoxysilyl, a monohalosilyl, a dihalosilyl, and a trihalosilyl.

33. The tolerogen of claim 32, wherein the surface binding group is trimethoxysilyl.

34. The tolerogen of claim 32, wherein the surface binding group is trihalosilyl.

35. The tolerogen of claim 21, wherein the stent is administered using angioplasty.

36. The tolerogen of claim 21, wherein the stent is administered through surgical implantation.

37. The tolerogen of claim 21, wherein the stent is administered to a neonate.

38. The tolerogen of claim 21, wherein the stent is administered to a patient who is growing past the age of infancy.

39. A method of inducing immunologic tolerance to non-self antigens in a human subject receiving a stent, the method comprising implanting the stent of the immunologic induction system of claim 1 in the human subject.

40. The method of claim 39, wherein the blood group antigen is selected from the group consisting of the A blood group antigen, the B blood group antigen, the O blood group antigen, and fragments and combinations thereof.

41. The method of claim 40, wherein the A blood group antigen, the B blood group antigen and the O blood group antigen are selected from the group consisting of Type I, Type II, Type III, Type IV, Type V, and Type VI blood group antigens.

42. The method of claim 39, wherein a plurality of different blood group antigens are coupled to the carrier.

43. The method of claim 39, wherein the blood group antigen is coupled to the stent through a linker.

44. The method of claim 43, wherein the linker is an aglycone that has an anchoring group.

45. The method of claim 44, wherein the anchoring group is selected from the group consisting of a monoalkoxysilyl, a dialkoxysilyl, a trialkoxysilyl, a monohalosilyl, a dihalosilyl, and a trihalosilyl.

46. The method of claim 45, wherein the anchoring group is trimethoxysilyl.

47. The method of claim 45, wherein the anchoring group is trichlorosilyl.

48. The method of claim 39, wherein the stent is made from silica-coated 316L stainless steel.

49. The method of claim 39, wherein the stent is made from $Al_2O_3$-coated 316L stainless steel.

50. The method of claim 39, wherein the tolerogen further comprises a polyethylene glycol (PEG)-containing molecule coupled to the stent.

51. The method of claim 50, wherein the polyethylene glycol-containing molecule comprises a surface binding group selected from the group consisting of a monoalkoxysilyl, a dialkoxysilyl, a trialkoxysilyl, a monohalosilyl, a dihalosilyl, and a trihalosilyl.

52. The method of claim 51, wherein the surface binding group is trimethoxysilyl.

53. The method of claim 51, wherein the surface binding group is trichlorosilyl.

54. The method of claim 39, wherein the human subject is a neonate.

55. The method of claim 39, wherein the human subject is a patient who is growing past the age of infancy.

56. The method of claim 39, wherein the stent is implanted to extend the window of safety for immunologically-incompatible transplantations.

* * * * *

UNITED STATES PATENT AND TRADEMARK OFFICE
CERTIFICATE OF CORRECTION

| | | |
|---|---|---|
| PATENT NO. | : 8,974,793 B2 | Page 1 of 1 |
| APPLICATION NO. | : 13/139387 | |
| DATED | : March 10, 2015 | |
| INVENTOR(S) | : Lori Jeanne West et al. | |

It is certified that error appears in the above-identified patent and that said Letters Patent is hereby corrected as shown below:

In the Claims:

At column 69, line 31, add --"(tolerogen)"-- between "(the)" and "(is)" in claim 16
At column 69, line 62, replace "(tnalkoxysilyl)" with --"(trialkoxysilyl)"-- in claim 27
At column 70, line 9, replace "(tnalkoxysilyl)" with --"(trialkoxysilyl)"-- in claim 32

Signed and Sealed this
Twenty-fifth Day of August, 2015

Michelle K. Lee
*Director of the United States Patent and Trademark Office*